United States Patent
Lingappa et al.

(10) Patent No.: US 7,041,462 B2
(45) Date of Patent: May 9, 2006

(54) CONFORMATIONAL AND TOPOLOGICAL PROTEIN REGULATION

(75) Inventors: Vishwanath R. Lingappa, San Francisco, CA (US); D. Thomas Rutkowski, San Francisco, CA (US); Ramanujan S. Hegde, Rockville, MD (US)

(73) Assignee: Regents of the University of California, Oakland, CA (US)

( * ) Notice: Subject to any disclaimer, the term of this patent is extended or adjusted under 35 U.S.C. 154(b) by 0 days.

(21) Appl. No.: 10/911,446

(22) Filed: Aug. 3, 2004

(65) Prior Publication Data
US 2005/0003489 A1 Jan. 6, 2005

Related U.S. Application Data

(62) Division of application No. 09/739,179, filed on Dec. 15, 2000, now Pat. No. 6,821,742.
(60) Provisional application No. 60/172,350, filed on Dec. 16, 1999, and provisional application No. 60/171,012, filed on Dec. 15, 1999.

(51) Int. Cl.
*A61K 33/567* (2006.01)

(52) U.S. Cl. .......................... 435/7.2; 435/7.2; 435/328; 435/7.21; 435/326; 536/23.5; 530/387.3; 424/133.1

(58) Field of Classification Search ................. 435/7.2, 435/328, 7.21, 326; 536/23.5; 530/387.3; 424/133.1
See application file for complete search history.

(56) References Cited

FOREIGN PATENT DOCUMENTS

| EP | 0 861 900 | 9/1998 |
|----|-----------|--------|
| WO | WO 96/08561 | 3/1996 |

OTHER PUBLICATIONS

Song et al. *Cell* 100:333–343 (2000).
Wiertz et al. *Nature* 384:432–438 (1996).
Sidrauski et al. *Trends Cell Biol* 8:245–249 (1998).
Ellgard et al. *Science* 286:1882–1888 (1999).
Anfinsen *Science* 181:223–230 (1973).
Ellis et al. *Faseb J.* 10:20–26 (1996).
Dill et al. *Nature Struct Biol* 4:10 (1997).
Blobel *PNAS* 77:1496–1500 (1980).
Gorlich et al. *Cell* 75:615–630 (1993).
Jungnickel et al. *Cell* 82:261–270 (1996).
Skach et al. *J. Biol Chem* 268:23552–23561 (1993).
Borel et al. *Cell* 85:379–389 (1996).
Heinrich et al. *Cell* 102:233–244 (2000).
Moss et al. *Mol Biol Cell* 9:2681–2697 (1998).
Matlack et al. *J. Cell Biol* 270:6170–6180 (1999).
Lyko et al. *J Biol Chem* 270:19873–19878 (1995).
Rapoport et al. *J Biol Chem.* 380:1143–1150 (1999).
Liu et al. *PNAS* 86:9213–9217 (1986).
Chen et al. *Mol Biol Cell* 11:765–772 (2000).
Hedge et al. *Science* 279:827–834 (1988).
Voigt et al. *J Cell Biol* 134:25–35 (1996).
Lopez et al. *Science* 248:226–229 (1990).
Hedge et al. *Mol Cell* 2:85–91 (1998).
Wolin et al. *J Cell Biol* 109:2617–2622 (1989).
Hedge et al. *Cell* 85:217–228 (1996).
Wickner et al. *Science* 286:1888–1893 (1999).
Ibba et al. *Science* 286:1893–1897 (1999).
Hedge et al. "Transmissible and genetic prion diseases share a common pathway of neurodegeneration" *Nature* 402:822–826 (1999).
Hoelscher et al. "Prion protein contains a second endoplasmic reticulum targeting signal sequence located at its C terminus" *J Biol Chem* 276:13388–13394 (2001).
Eble et al. "Multiple topogenic sequences determine the transmembrane orientation of hepatitis B surface antigen" *Mol cell Biol* 7:3591–3601 (1987).
Bhagwat et al. *J Biol Chem* 274:24014–24022 (1999).
Skach et al. *J Biol Chem* 2681):6903–6908 (1993).

*Primary Examiner*—Christopher R. Tate
*Assistant Examiner*—B. Dell Chism
(74) *Attorney, Agent, or Firm*—Foley & Lardner LLP

(57) ABSTRACT

Methods and compositions are provided for identifying novel conformers of proteins not known to exist as different conformers. By using chimeric genes replacing a native signal sequence with a different signal sequence resulting in the production of a conformer, one can compare the native protein with the product of the chimeric gene. Where the conformations are different, the different protein may be used for production of antibodies, elucidation of mechanisms associated with the native and different conformer protein, assays for the presence of the different conformer in physiological samples, identification of compounds specifically binding to the conformer, particularly drugs, etc. Where the formation of the conformer is associated with a diseased state, the conformer may be used in screens to identify compounds as drug candidates.

2 Claims, 20 Drawing Sheets

A

MANLSYWLLALPVAMWTDVGLC KKRPK...  PrP

MRRLSYWLLALPVAMWTDVGLC KKRPK...  PrP(R2,3)

MDDLSYWLLALPVAMWTDVGLC KKRPK...  PrP(D2,3)

MANRRYWLLALPVAMWTDVGLC KKRPK...  PrP(R4,5)

MANDDYWLLALPVAMWTDVGLC KKRPK...  PrP(D4,5)

US 7,041,462 B2

CONFORMATIONAL AND TOPOLOGICAL PROTEIN REGULATION

CROSS REFERENCE TO RELATED APPLICATIONS

Figure 1:
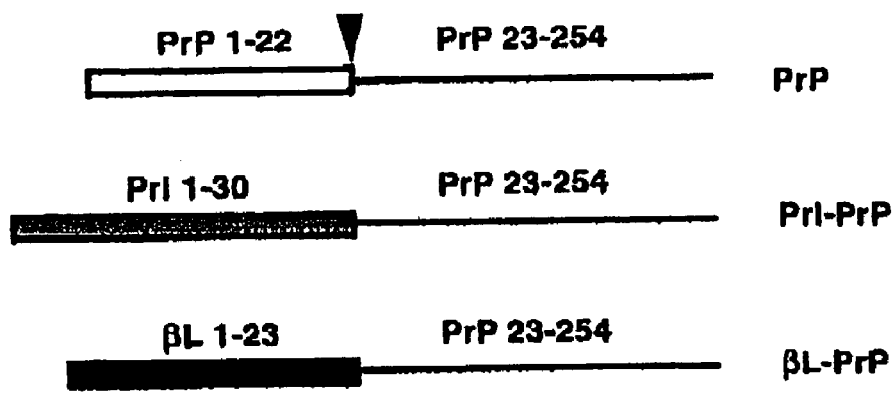
Figure 1:
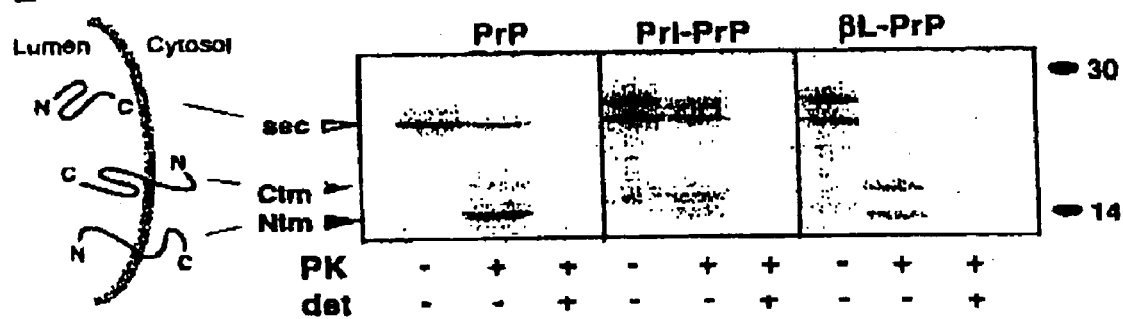
Figure 1:
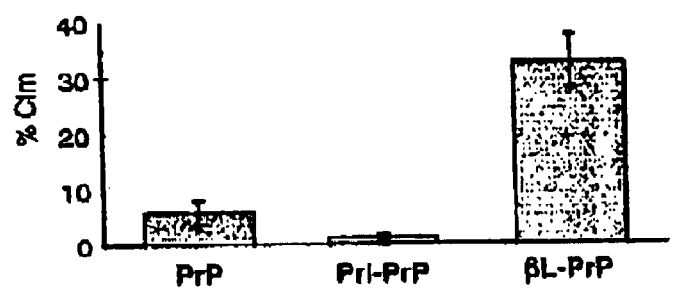

This application is a divisional of U.S. Ser. No. 09/739,179 filed Dec. 15, 2000, now U.S. Pat. No. 6,821,7842, which claims benefit of U.S. Ser. No. 60/171,012 filed Dec. 15, 1999 and U.S. Ser. No. 60/172,350 filed Dec. 16, 1999, which disclosures are incorporated herein by reference.

INTRODUCTION

1. Technical Field

The field of this invention is biological models and therapeutics.

2. Background

Conventionally, gene expression in higher eukaryotes is generally believed to involve the conversion of information encoded in the genome into proteins through the processes of transcription, RNA splicing and export, and translation. Localization of newly synthesized proteins to the correct intracellular compartment, and folding into the correct tertiary structure, are two additional processes at which gene expression could, in principle, be regulated. However, until now the former has been viewed as regulated only with respect to fidelity (Song et al, Cell (2000) 100:333–343), degradation (Wiertz et al, Nature (1996) 384:432–438), or signaling to other compartments (Sidrauski et al., Trends Cell Biol (1998) 8:245–249), and not with respect to the information content of the expressed gene. Likewise, folding has also not been viewed at a point of fundamental regulation of gene expression. In general, a dichotomy has been accepted between a protein being either properly folded or misfolded (Ellgaard, et al., Science (1999) 286:1882–1888). The possibility that proteins might have more than one properly folded state and that the cell might be able to select one versus another folded state under particular circumstances or conditions, has not been seriously considered. If either of these possibilities were true, the information content of the genome would be greatly increased. If an invention made it possible to select one conformation versus another, such an invention would be a platform for determining and accessing the information content of the genome in ways that have not been heretofore possible.

In regards to protein folding, a fundamental dogma of modern biology is that primary structure determines secondary structure, which, together with relevant post-translational modifications such as glycosylation, determines the tertiary structure of proteins (Anfinsen, Science (1973) 181:223–230). One revision of this view occurred with the realization that molecular chaperones play a crucial role in enhancing the fidelity of protein folding by preventing inappropriate interactions, thereby facilitating the process of achieving the proper final folded state (Ellis and Hartl, Faseb J (1996) 10:20–26). The recognition that folding is likely initiated in many parts of the molecule at the same time, allowing the chain to funnel towards a minimum energy state without sampling every possibility along the way, constituted a second revision in the generally accepted view of protein folding (Dill and Chan, Nature Struct Biol (1997) 4:10). Neither of these notions considers the possibility that folding might be regulated in the sense of proceeding down one versus another pathway contingent on one versus another set of protein-protein interactions. If this were the case, protein folding could be amenable to manipulation in ways that could confer diagnostic or therapeutic advantage.

Proteins destined to be secreted from the cell generally contain a signal sequence at the amino terminus that initiates a series of protein-protein interactions directing the growing chain to the endoplasmic reticulum (ER) membrane and through the translocation channel into the ER lumen (Blobel, PNAS (1980) 77:1496–1500). The roles of signal recognition particle and its receptor (Walter and Johnson, 1996) and of the heterotrimeric Sec 61 complex (Gorlich and Rapoport, Cell (1993) 75:615–630) and of other proteins (Jungnickel and Rapoport, Cell (1996) 82:261–270) in these processes has been elucidated.

Assembly of integral membrane proteins into the membrane of the ER appears to be a complex variation on this general theme, directed by internal signal sequences and stop transfer sequences and hybrid signal-anchor sequences whose interaction with various ER proteins directs the final transmembrane orientation of the polypeptide and often play a subsequent role in anchoring the protein in the bilayer after the chain is released from the translocation channel into the lipid bilayer (Skach and Lingappa, J Biol Chem (1993) 268:23552–23561; Borel and Simon, Cell (1996) 85:379–389; Heinrich et al, Cell (2000) 102:233–244; Moss et al., Mol Biol Cell (1998) 9:2681–2697).

In the case of secretory proteins, the signal sequence is usually cleaved from the growing chain by the ER membrane associated signal peptidase complex, trapping the nascent chain in the ER lumen (Matlack et al., J Cell Biol (1999) 270:6170–6180), with the cleaved signal peptide most likely returned to the cytosol and degraded (Lyko et al., J Biol Chem (1995) 270:19873–19878). In bacteria and primitive eukaryotes such as yeast, a substantial amount of translocation occurs after synthesis is completed (Rapoport et al., J Biol Chem (1999) 380:1143–1150). In such post-translational translocation, a role for the signal sequence as a molecular chaperone to maintain the unfolded state has been proposed (Liu et al., PNAS (1986) 86:9213–9217). However in higher eukaryotes, where most translocation across the ER membrane appears to occur co-translationally, that is, while the chain is still being made, it has generally been assumed that the nascent chain is transferred directly to the ER lumen where folding is initiated (Chen and Helenius, Mol Biol Cell (2000) 11:765–772).

Taken together, the studies presented here suggest the need for several revisions in the current paradigm of protein folding:

First, the simple dichotomy between properly folded and misfolded proteins must be abandoned. It needs to be recognized that protein folding can result in multiple properly folded states which may, potentially, subserve different functions. In most cases these are extremely difficult to detect not only because tools to easily distinguish conformational variants of proteins are limited and not easily applied, but also because the cell complicates the task by-degrading variants not wanted at a given point in time.

Second, it must be recognized that the cell has mechanisms by which one folded state (and therefore one function) is chosen (to survive degradative mechanism and be exported to the surface or out of the cell at one time while another folded state (and another function) may be chosen at another time.

Third, it is clear that the machinery and determinants involved in translocation across the ER membrane play an important role in selecting the folding funnel down which a newly synthesized protein proceeds, and that manipulation of either the signal sequence or the machinery with which the chain interacts in the cytosol, membrane or ER lumen are ways to change the folding funnel selected, and therefore, the final conformation or mix of conformations of the protein.

The major implication of the first two revisions of the protein folding paradigm is to increase the information content of the genome enormously. The major implication of the third is to reveal a means of accessing this increased information content of the genome for diagnostic and therapeutic advantage, giving rise to the subject invention.

Figure 3:
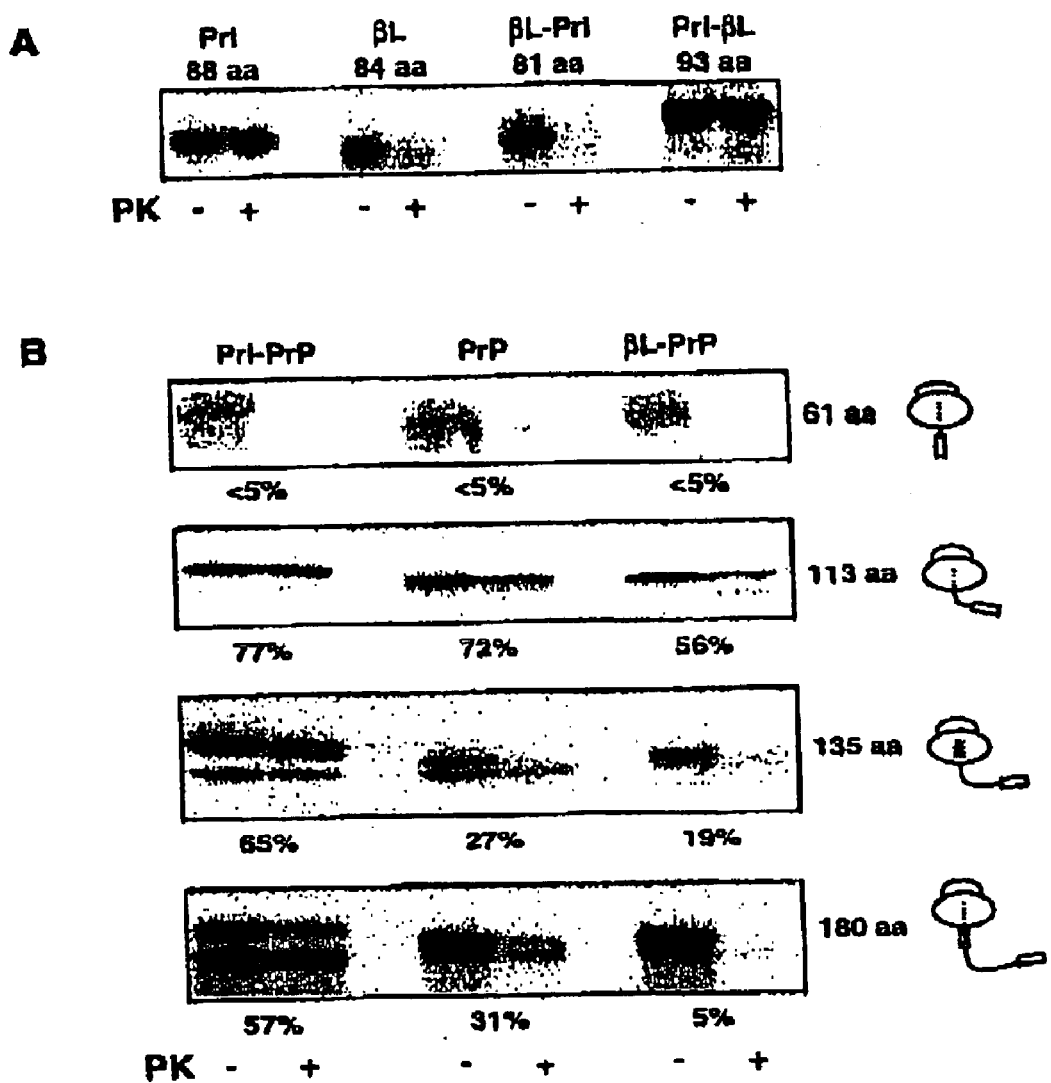

Besides elucidating these points of background, our studies demonstrate an invention by which the choice of folding funnel can be altered for any given protein in a way that does not change the proteins final primary structure, but which can result in dramatic changes in the protein's final folded conformation or shape. We demonstrate the signal sequence is able to influence the folding funnel utilized by the growing polypeptide chain, and thereby, to influence the final folded conformation of the resulting newly synthesized protein. Furthermore, cells are able to choose one versus another final conformation through signal sequence-mediated regulation. Because a linear polypeptide sequence folding in different ways could have substantially different shapes, physical properties and biological activities, this new level of regulation greatly increases the information content of the genome and the potential for regulation of gene expression available to the cell.

BRIEF DESCRIPTION OF THE DRAWINGS

FIG. 1 shows the effects on topology of replacing the PrP signal sequence. FIG. 1(A) shows schematic diagrams of wild-type PrP, Prl-PrP, and βL-PrP. Boxes represent signal sequences from PrP, preprolactin, and pre-beta-lactamase, fused to the PrP mature region. Cleavage site is indicated by arrowhead. FIG. 1(B) shows the topology of PrP, Prl-PrP, and βL-PrP. Microsomes from in vitro translation and translocation reactions of each construct were isolated by sedimentation and divided into equal aliquots for digestion with proteinase K (PK) in the presence or absence of 1% Triton X-100 (detergent) as indicated below the gel. One aliquot was left untreated. The three topological forms of PrP yield distinctively sized bands upon digestion with PK in the absence of detergent (Hedge et al. (1988a) Science 279, 827–834). The position of each band, along with a diagrammatic representation of the respective topology, is provided to the left of the gel. Cleavage of the signal sequence of Prl-PrP was inefficient, causing $^{sec}$PrP and $^{Ntm}$PrP to be represented by both a signal-cleaved species and a signal-uncleaved species. Molecular weight markers are at right. The percentage of translocated chains in the $^{Ctm}$PrP topology for each construct was quantitated from 3 such experiments and is shown in (C) (mean+/−SEM).

FIG. 2 shows that kinetics of targeting do not influence PrP topology. FIG. 2 (A) shows PrP translated in the presence of varying amounts of microsomes as indicated on the x-axis. Following proteolysis assays for topology, autoradiographs were quantitated to determine the percentage of total translation product that was signal cleaved (closed squares), and the percentage of translocated chains in the $^{Ctm}$PrP topology (open circles). FIG. 2(B) shows translation reactions of PrP synchronized by inhibition of initiation at 5 minutes with 75 mM ATA. At staggered intervals (as indicated on the x-axis), aliquots were removed, microsomes were added, and targeting and translocation were allowed to proceed for 30 minutes. Topology and signal cleavage were determined and plotted as in FIG. 2(A). FIG. 2(C) shows an StuI-truncated mRNA, encoding the 223-mer of PrP, translated in the presence (open bars) or absence (shaded bars) of microsomes. After 5 minutes, further initiation was inhibited with ATA, and at 30 minutes, microsomes were added to the sample lacking them and the incubation for both reactions was continued for an additional 30 minutes. Nascent chains were then released from the ribosomes with 10 mM EDTA. Signal cleavage and topology were assessed and quantitated as above.

FIG. 3 shows that the signal sequence influences the ribosome-membrane junction. FIG. 3(A): Truncated mRNAs for preprolactin (Prl), pre-beta-lactamase (βL), βL-Prl and Prl-βL were translated and translocated, and the microsomes from these reactions were isolated by sedimentation. One aliquot of each sample was left untreated and PK was added to the remainder. Prl and βL-Prl were truncated at PvuII. βL and Prl-βL were truncated at HpaII. The sizes of these constructs in amino acids are indicated. FIG. 3(B): Prl-PrP, wild-type PrP, and βL-PrP were truncated at BstXI (61 aa for wild-type PrP), NaeI (113 aa), XbaI (135 aa), or HincII (180 aa) and analyzed by proteolysis as in FIG. 3(A). The percentage of material protected from digestion by PK was measured by densitormetric quantitation of the autoradiographs shown, and is given below each sample. The drawings at right represent the position of both the signal sequence (open box) and transmembrane domain (gray box) with respect to the ribosome.

FIG. 4 shows dissociation of topology from TRAM dependence. FIG. 4(A): signal sequences of constructs PrP, $PrP_{(R2,3)}$, $PrP_{(D2,3)}$, $PrP_{(R4,5)}$, and $PrP_{(D4,5)}$. The amino acid changes in each construct are underlined, and the site of signal cleavage is indicated by an arrowhead. FIG. 4(B): the constructs shown in FIG. 4(A) were used to program translation and translocation reactions, and the resultant topology analyzed by proteolysis as in FIG. 1B. The percent of $^{Ctm}$PrP synthesis was quantitated by densitometry of the autoradiographs and is shown for each construct. The signal sequence of each construct is indicated on the x-axis. $^{Ctm}$PrP synthesis for Prl-PrP and βL-PrP is shown for comparison. FIG. 4(C): the PrP signal sequence mutations shown in FIG. 5A were fused to the prolactin mature region. The signal sequences of prepro-alpha factor (dependent) and preprolactin (independent), fused to the prolactin mature region, served as controls for TRAM-dependent and TRAM-independent signal sequences, respectively (see Voigt et al., (1996) J. Cell. Biol. 134, 25–35). Constructs were translated and translocated in ConA-depleted proteoliposomes containing or lacking purified TRAM (prepared as described in the Experimental Procedures). An aliquot from each reaction was set aside to verify that the efficiency of translation was identical in both types of proteoliposomes. The remainder of the material was treated with 0.5 mg/mr PK and immunoprecipitated with anti-protein antibodies. TRAM dependence, shown here, was measured as the percent diminishment of protease protected material in the proteoliposomes lacking TRAM relative to TRAM-containing membranes.

FIG. 5 shows relationship between the signal sequence and TM domain. FIG. 5(A): Constructs $PrP_{(AV3)}$, Prl-PrP $_{(AV3)}$, and βL-$PrP_{(AV3)}$were translated, translocated, and analyzed for topology by proteolysis exactly as in FIG. 1B. The migration of each topological form is indicated at right. FIG. 5(B): Constructs $PrP_{(G123P)}$, Prl-$PrP_{(G123P)}$, and βL-PrP (G123P) were translated, translocated, and analyzed for topology by PK exactly as in FIG. 1B. Only $^{sec}$PrP is observed, and its migration is indicated at right. FIG. 5(C): HincII-truncated mRNAs coding for ~180-mers of PrP, Prl-$PrP_{(AV3)}$. and βL-$PrP_{(G123P)}$ were translated in the presence of microsomes, which were then isolated by sedimentation. Proteolysis with PK to examine the state of the ribosome-membrane junction was performed exactly as in FIG. 3B.

Figure 6:
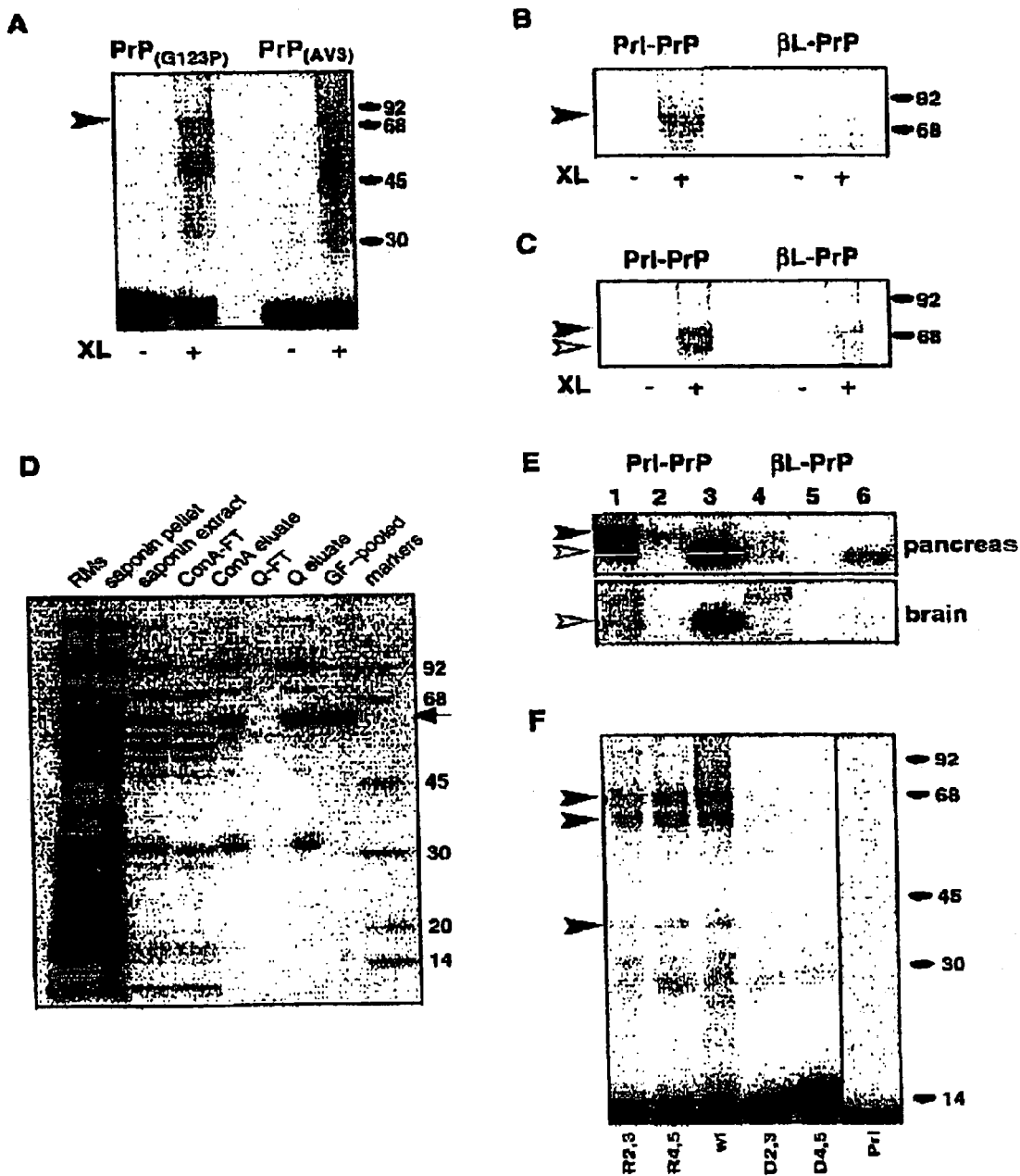

FIG. 6 shows the interaction of $^{SBC}$PrP with PDI. FIG. 6(A): HincII-truncated mRNAs coding for PrP$_{(G123P)}$ and PrP$_{(AV3)}$ (~180-mers) were translated, and the membranes were isolated by sedimentation. One aliquot was treated with 1 mM DSS (+XL) and the remainder was left untreated (−XL). Uncrosslinked material is shown at the bottom of the gel. The migrations of the molecular weight markers are shown at right. The arrowhead indicates a protein of approximately 65 kDa which cross-links preferentially to PrP$_{(G123P)}$. FIG. 6(B): Prl-PrP and βL-PrP were truncated at HincII and treated exactly as in FIG. 6(A). Equal amounts of total translation product were loaded in each lane. The 65 kDa cross-link seen in (A) is indicated by an arrowhead. FIG. 6(C): Prl-PrP and βL-PrP were truncated at NaeI (~113-mers) and analyzed by cross-linking exactly as in FIG.(A). The 65 kDa cross-link seen in FIG. 6(A) (closed arrowhead) and a 60 kDa cross-link which also preferentially forms with Prl-PrP (open arrowhead) are indicated. FIG. 6(D): Purification of PDIp. Shown is a Coomassie stain of starting rough microsomes (RMs); proteins not extracted (pellet) or extracted by saponin treatment; flow-through (FT) and eluate of the saponin extract from a ConA-sepharose column; flow-through and eluate of the ConA eluate from a Q-sepharose column, and the pooled peak fractions from a gel-filtration (GF) column, resulting in purification of p65 (arrow) to near-homogeneity. See Experimental Procedures for details of the purification. FIG. 6(E): Prl-PrP and β-PrP were translated in the presence of either pancreas (top panel) or brain (bottom panel) microsomes, and the membranes were isolated by sedimentation. Following cross-linking with 1 mM DSS, the nascent chains were released from the ribosomes with 10 mM EDTA, and 0.5% saponin was added to extract the lumenal proteins. One aliquot was set aside (lanes 1, 4), and antibodies against PDIp (lanes 2, 5) or PDI (lanes 3, 6) were added directly to the remaining material for immunoprecipitation. Prl-PrP translated in pancreatic microsomes cross-links preferentially to PDIp (closed arrowhead) and PDI (open arrowhead), while only a cross-link to PDI (open arrowhead) is observed in brain microsomes. FIG. 6(F): mRNAs encoding wild-type PrP and signal sequence point mutants from FIG. 4A, truncated at NaeI to yield ~113-mers, as well as wild-type preprolactin (Prl) truncated at MboII to yield a 100-mer, were translated and analyzed by cross-linking as in panel (A). Following cross-linking and nascent chain release with 10 mM EDTA, 0.5% saponin was added, the membranes were sedimented, and the supernatant, containing lumenal proteins, was recovered. Arrowheads designate $^{sec}$PrP-specific lumenal cross-links. The signal sequence of each construct is indicated below the gel.

Figure 7:
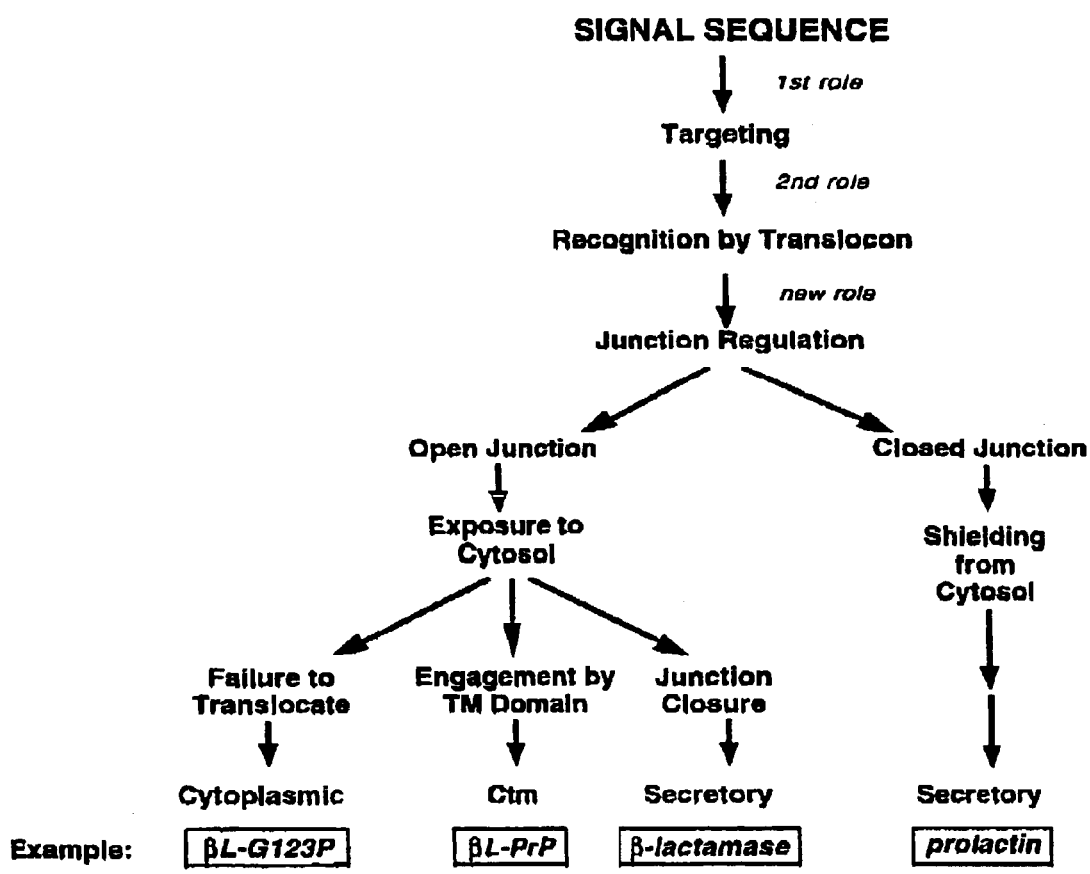

FIG. 7 shows a hypothetical model for signal sequence action. The signal sequence determines the state of the ribosome-membrane junction, which in turn influences final topological fate in the case of PrP, and perhaps more subtle aspects of translocational behavior or other substrates. An example of each translocational outcome is given.

Figure 8:
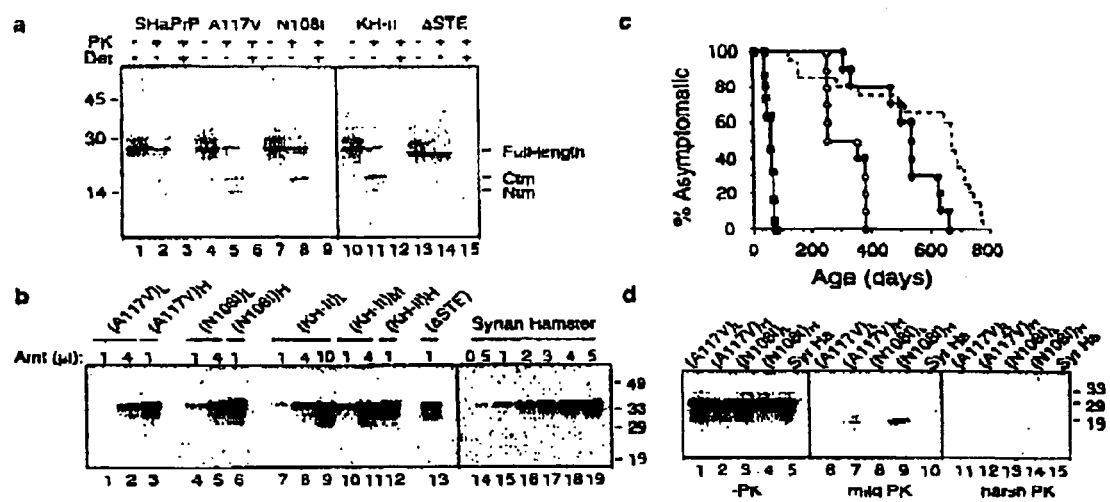

FIG. 8 shows a dose response of $^{Ctm}$PrP induced neurodegeneration. FIG. 8(A): Topology of wild type and mutant PrP molecules at the ER. In vitro synthesized transcript coding for each PrP construct (indicated above the gels) was used to program a rabbit reticulocyte lysate cell-free translation reaction containing ER derived microsomal membranes and a competitive peptide inhibitor of glycosylation. Following translation, samples were either left untreated or digested with PK in the absence or presence of 0.5% Triton X-100 ("Det") as indicated above the gel. The positions of the full-length PrP molecule, the NH$_2$-terminal fragment (indicative of $^{Ntm}$PrP) and the COOH-terminal fragment (indicative of $^{Ctm}$PrP) generated by PK digestion are marked at the right. FIG. 8(B): Level of expression of various transgenic mouse lines. Varying amounts in (μl, indicated above the lanes) of 10% brain homogenate from each transgenic mouse was immunoblotted for PrP with 13A5 monoclonal antibody and compared to a titration of syrian hamster brain homogenate. FIG. 8(C): Time course of development of symptoms in Tg[SHaPrP(A117V)$_H$] (closed circles) and Tg[SHaPrP(N108I)$_H$] (open circles). Non-transgenic control animals (dashed line) and Tg[SHaPrP (KH→II)$_H$] (closed squares; data from Manson, et al. (1994) *Neurology* 46:532-537) are shown for comparison. FIG. 8(D): Analysis of various transgenic mice and Syrian hamster (as indicated above the gel) for $^{Ctm}$PrP and PrP$^{Sc}$ as described in Methods. Tg[SHaPrP(A117V)$_H$] and Tg[SHaPrP(N108I)$_H$] samples were from clinically ill mice and Tg[SHaPrP(A117V)$_L$] and Tg[SHaPrP(N108I)$_L$] samples were from mice (which showed no signs of disease) at least 600 days of age. The fragment of PrP resistant to PK under the 'mild' conditions, indicative of $^{Ctm}$PrP is only seen in the Tg[SHaPrP(A117V)$_H$] and Tg[SHaPrP(N108I)$_H$] samples. No PK resistant PrP$^{Sc}$ was observed in any of the samples.

Figure 9:
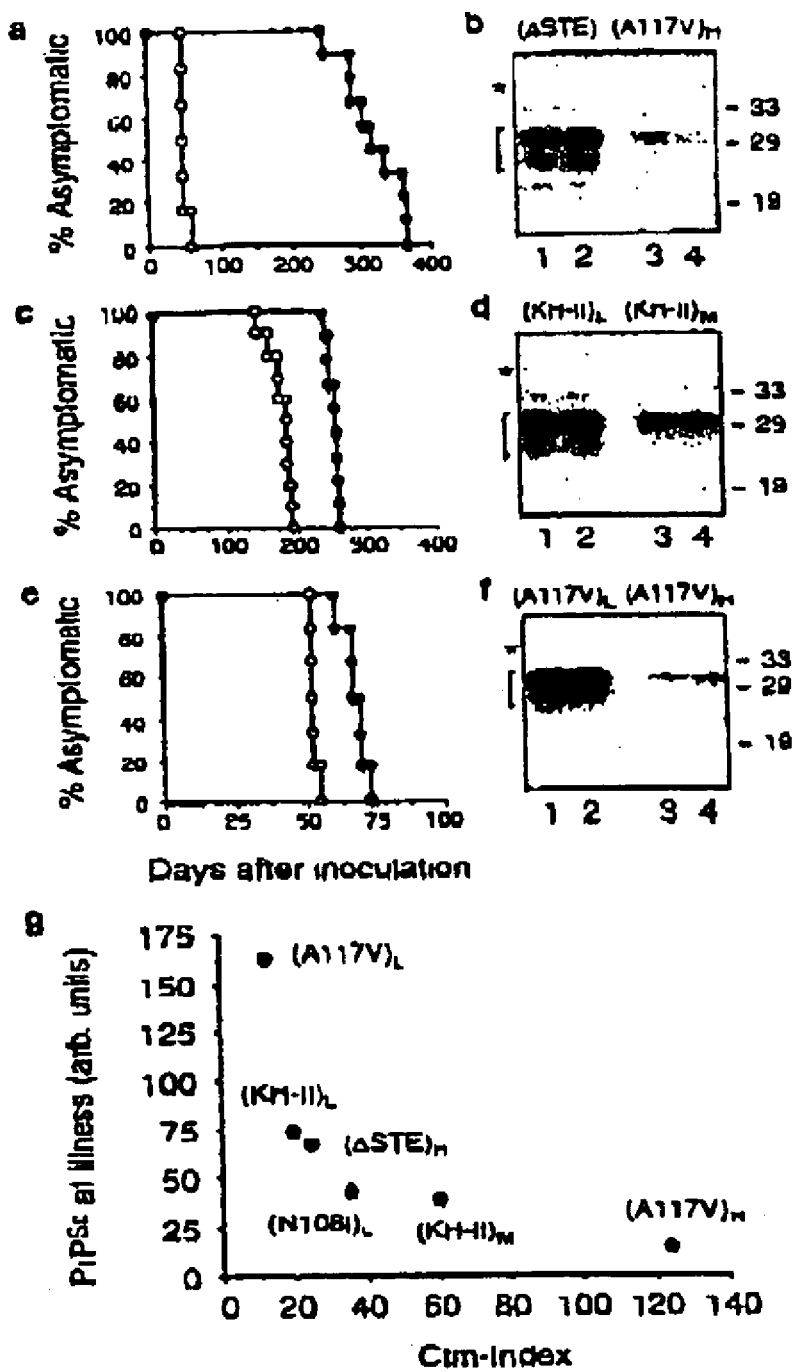

FIG. 9 shows a relationship between $^{Ctm}$PrP and PrP$^{Sc}$. FIG. 9(A), (C), (E): Time course of development of illness in various transgenic lines following inoculation with Sc237 hamster prions. FIG. 9(B), (D), (F): Relative levels of protease-resistant PrP$^{Sc}$ at time of illness in various transgenic lines. Duplicate samples of each line were digested using 'harsh PK' conditions as described in Methods and equivalent amounts of each sample separated by SDS-PAGE. The C-terminal PrP27-30 fragment characteristic of PrP$^{Sc}$ (indicated with a bracket) was detected by immunoblotting with the 13A5 monoclonal antibody. The position of undigested, full length PrP is indicated with an asterisk. FIG. 9(G): The Ctm-index for each transgenic line (see Table 1) was plotted against the amount of PrP$^{Sc}$ accumulated at the time of illness following inoculation with Sc237 prions.

Figure 10:
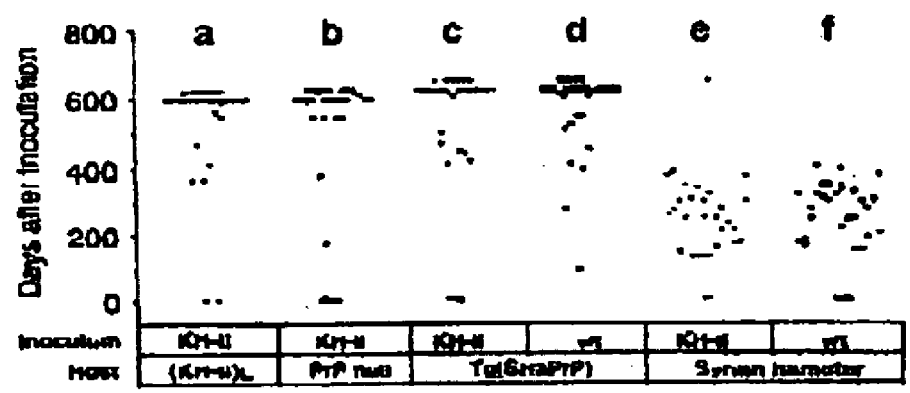

FIG. 10 shows a lack of transmission of CtmPrP induced neurodegenerative disease. Terminally ill Tg[SHaPrP (KH→II))$_H$] mice ('KH→II') and clinically normal Tg[SHaPrP] mice ('wt') were sacrificed and homogenates of the brain tissue inoculated intracerebrally into various hosts as indicated below the graph. The host animals used were Tg[SHaPrP(KH→II)$_L$] ['(KH→II)$_L$'], FVB/Prnp$^{0/0}$ ('PrP null'), Tg[SHaPrP], and Syrian hamsters. The time (in days) at which individual animals died following inoculation is plotted. Deaths by all causes, including those related to the inoculation itself, are plotted. The experiments were terminated after ~600 days with none of the remaining animals showing any signs or symptoms of neurologic disease. Each experiment represents three sets of 10 host animals injected with inoculi prepared from three separate animals to be tested. It should be noted that in our animal care facility, hamsters routinely live approximately 200 to 400 days, while mice last greater than 600 days (data not shown).

Figure 11:
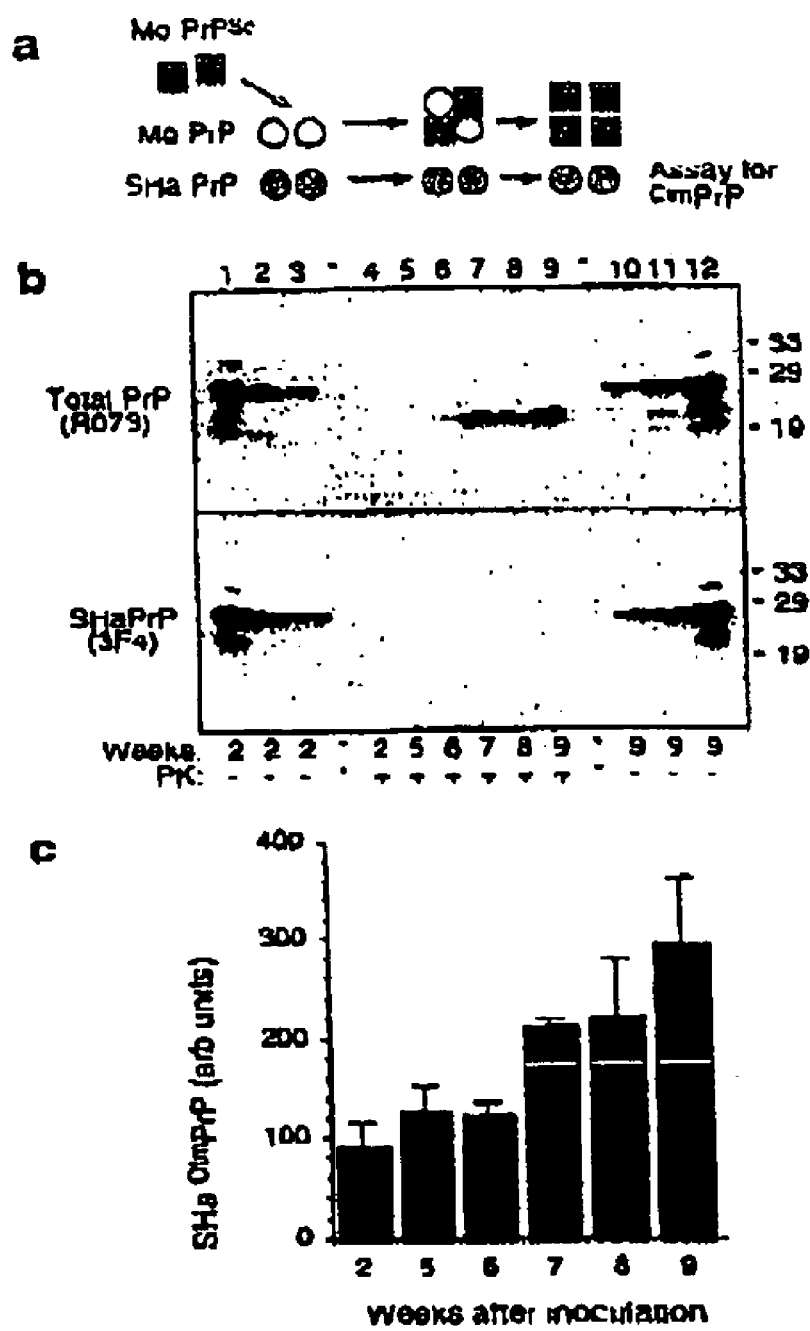

FIG. 11 shows $^{Ctm}$PrP generation during time course of PrP$^{Sc}$ accumulation. FIG. 11(A): Schematic of experimental design. Double transgenic mice expressing both SHaPrP and MoPrP (represented by the shaded and open circles, respectively) are inoculated with RML mouse prions (crosshatched squares). Over time, host MoPrP$^C$ is converted to MoPrP$^{Sc}$ and accumulates. During this time course, the HaPrP is not converted to HaPrP$^{Sc}$ owing to the species barrier and may therefore be assayed for $^{Ctm}$PrP. FIG. 11(B): Relative amounts of total PrP$^{Sc}$ and SHaPrP$^{Sc}$ in mice at various times (in weeks) after inoculation with RML. Homogenate was digested using the 'harsh PK' conditions, treated with PNGase, and analyzed by SDS-PAGE and immunoblotting with either R073 polyclonal antibody (to detect total PrP) or the 3F4 monoclonal antibody (to selectively probe for SHaPrP). An equivalent amount of homogenate is analyzed in each lane except lanes 2 and 11 (which contain one-fourth as much) and lanes 3 and 10 (which contain one-tenth as much). FIG. 11(C): Relative amounts of hamster $^{Ctm}$PrP (detected selectively using the 3F4 monoclonal antibody) at various times after inoculation with RML. Each bar represents the average ±SEM of three determinations.

Figure 12:
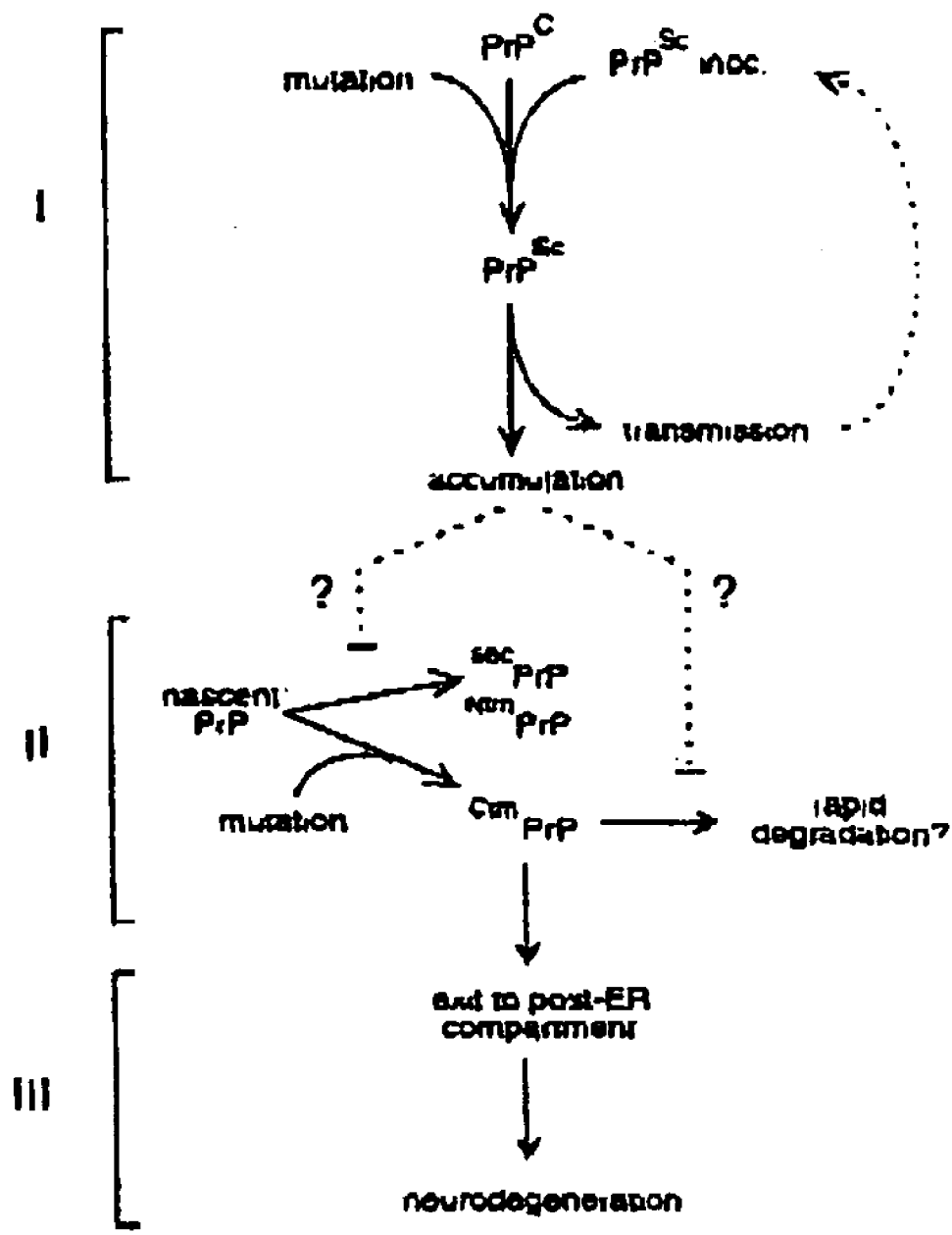

FIG. 12 shows a three stage model of prion disease pathogenesis. Stage I is the formation and accumulation of PrP$^{Sc}$. This could be initiated by either inoculation or spontaneous conversion of a mutated PrP$^C$ to PrP$^{Sc}$. Stage II comprises the events involved in generating $^{Ctm}$PrP. These events could be affected in trans at a presently unknown step (dashed lines with question marks) by accumulated PrP$^{Sc}$ or in cis by certain mutations within PrP. Stage III represents the events (currently unknown) involved in $^{Ctm}$PrP mediated neurodegeneration. This likely involves exit of $^{Ctm}$PrP to a post-ER compartment as a first step. In this model, PrP$^{Sc}$ can cause disease (via $^{Ctm}$PrP), but is not absolutely necessary, whereas $^{Ctm}$PrP production is necessary and sufficient for the development of disease.

Figure 13:
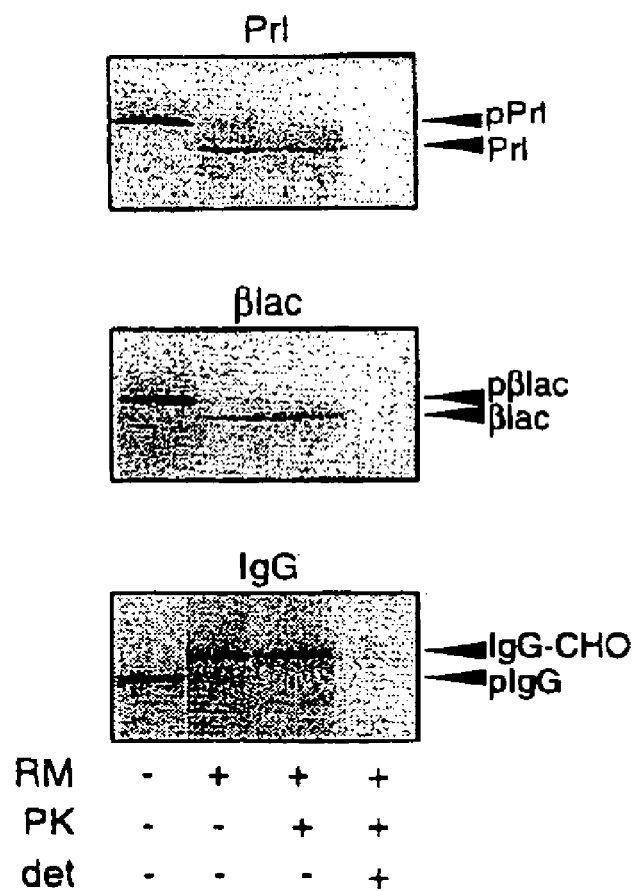

FIG. 13 shows efficiency of model secretory protein signal sequences. Full-length mRNAs for preprolactin (Prl), pre-beta-lactamase (βlac), and pre-IgG heavy chain (IgG) were translated in a rabbit reticulocyte lysate in the absence or presence of canine pancreatic microsomal membranes (RM), and equal aliquots of the translated material were left untreated or treated with Proteinase K (PK) in the presence or absence of 1% Triton X-100 (det). The positions of unprocessed material (pPrL, pβlac, pIgG) are indicated, as are the positions of signal-cleaved (Prl, βlac) and glycosylated (IgG-CHO) material.

Figure 14:
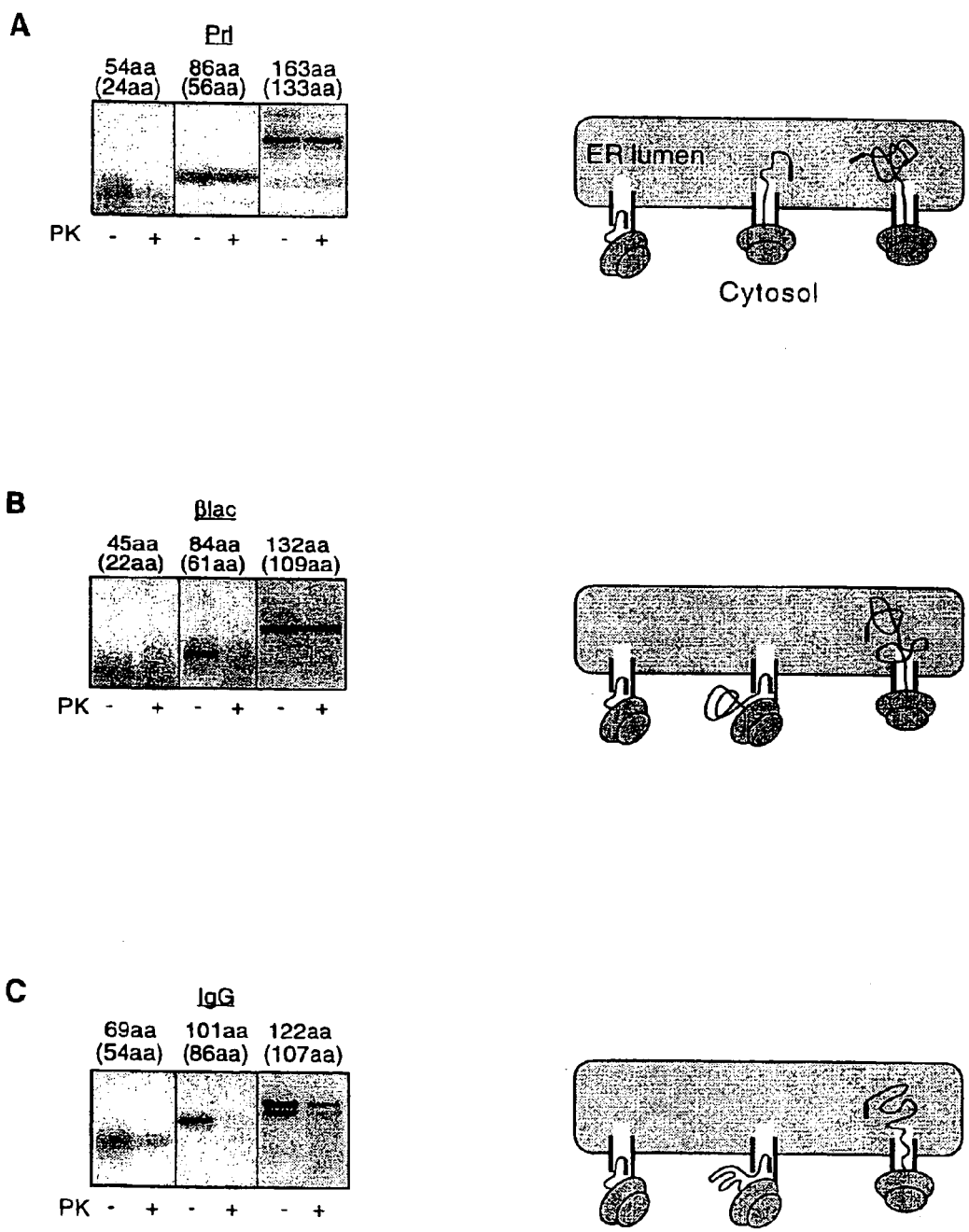

FIG. 14 shows that nascent secretory proteins act differentially on the ribosome-membrane junction. FIG. 14(A): Preprolactin mRNA was truncated at successive locations giving rise to nascent chains containing the noted number of N-terminal amino acids. The number of amino acids of the signal-cleaved protein is given in parentheses. The state of the ribosome-membrane junction was assessed by proteolysis exactly as in Rutkowski et al. ("A New Role for the Signal Sequence in Translocational Regulation", see priority applications 60/171,012 and 60/172,350) FIG. 14(B) and (C): βlac and IgG mRNAs were serially truncated at the indicated locations and analyzed by proteolysis as in (A). For each panel the cartoon to the right depicts the state of the ribosome-membrane junction at each of the three points during chain growth. Note that the left panel only of FIG. 14A and the left and center panels of B and C depict an "open" ribosome-membrane junction, while the center and right hand panels of FIG. 14A and the right hand panels of FIG. 14B and C depict a "closed" ribosome-membrane junction.

Figure 15:
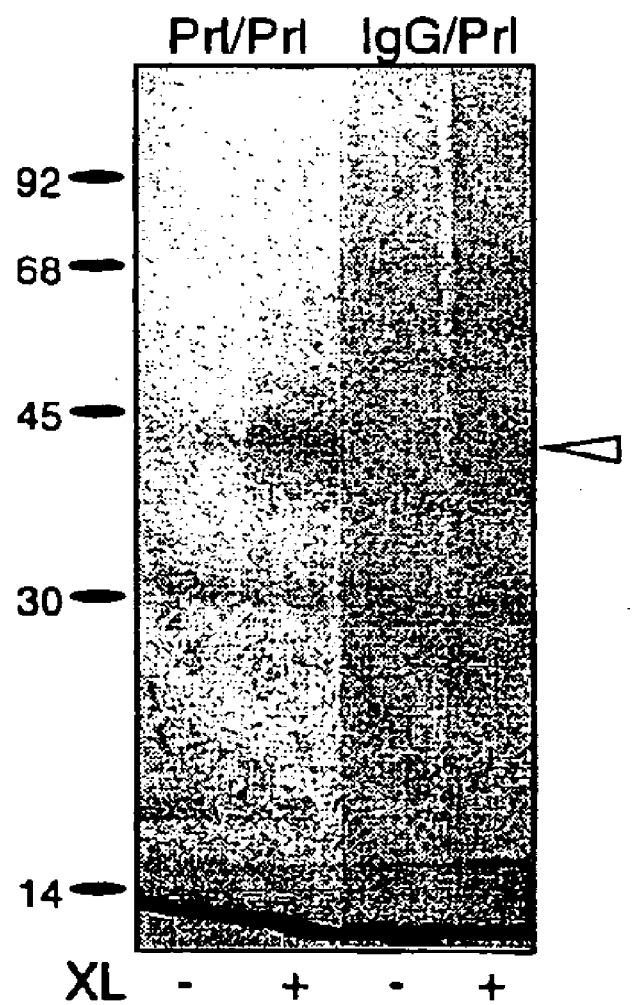

FIG. 15: Prolactin (Prl) and IgG/Prl were truncated at PvuII (encoding the signal sequence and 56 amino acids of the mature region of each protein) and translated in the presences of canine pancreatic rough microsomes. Targeted chains were isolated by sedimentation. One aliquot was set aside and the other was treated with 2 mM BM(PEO)3 [XL]. The arrowhead indicates a protein of approximately 35 kDa which cross-links preferentially to Prl. 10 kDa uncross-linked material is at the bottom of the panel. Migration of molecular weight markers is indicated to the left of the gel.

Figure 16:
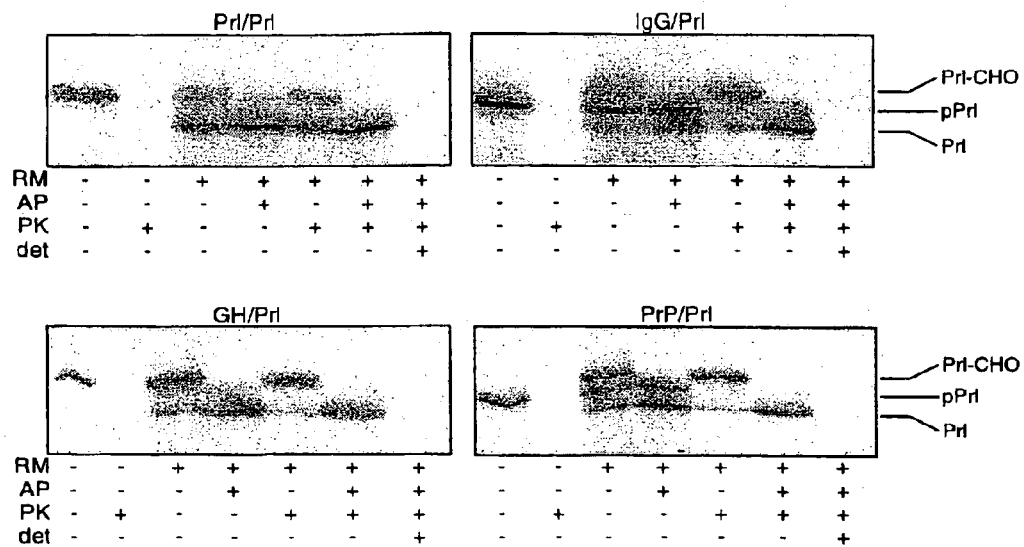
Figure 16:
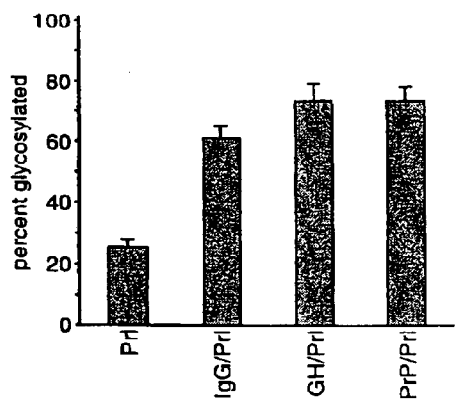
Figure 16:
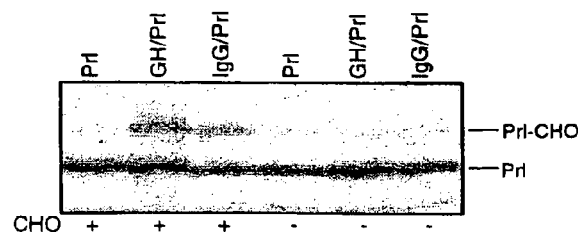

FIG. 16: Glycosylation as a reporter of signal sequence-dependent conformational change. FIG. 16(A): in vitro-transcribed mRNAs encoding native preprolactin (Prl) with an engineered N-terminal glycosylation site, or glycoprolactin fused to the signal sequences of mouse IgG heavy chain (IgG/Prl), rat growth hormone (GH/Prl), or hamster PrP (PrP/Prl), were translated in a rabbit reticulocyte lysate system, either in the presence or absence of canine rough microsomes (RM) as indicated. A competitive inhibitor of glycosylation was also added to some samples (AP). Following translation, samples were either set aside or incubated with 0.5 mg/ml proteinase K (PK) in the presence or absence of 1% Triton X-100 (det) at 0° for 30 minutes. The reactions were then run on SDS-PAGE and visualized by autoradiography. Three species of prolactin are indicated: signal-cleaved, translocated, glycosylated prolactin (Prl-CHO); signal-uncleaved untranslocated preprolactin (pPrl); and signal cleaved, translocated, nonglycosylated prolactin (Prl). FIG. 16(B): The percentage of prolactin chains achieving glycosylation for each construct was quantitated from three experiments by scanning and densitometric analysis of the autoradiographs such as those shown in (FIG. 16(A). FIG. 16(C): COS-1 cells were transiently transfected with expression plasmids encoding glycoprolactin with its own signal sequence or those of rat growth hormone or mouse IgG heavy chain. For comparison, the same constructs lacking glycosylation sites were also transfected (—CHO). Following a 45 minute preincubation of the cells in serum-free methionine-free medium, 100 μCi of a $^{35}$S-Methione/Cysteine mixture was added to the cell medium and the cells were labeled for 1 hour. An aliquot of the media from these cells was run directly on SDS-PAGE. Both glycosylated and unglycosylated forms of prolactin are indicated to the right of the panel. While glycosylated GH/Prl and IgG/Prl are clearly visible, no glycosylated native prolactin is observed.

Figure 17:
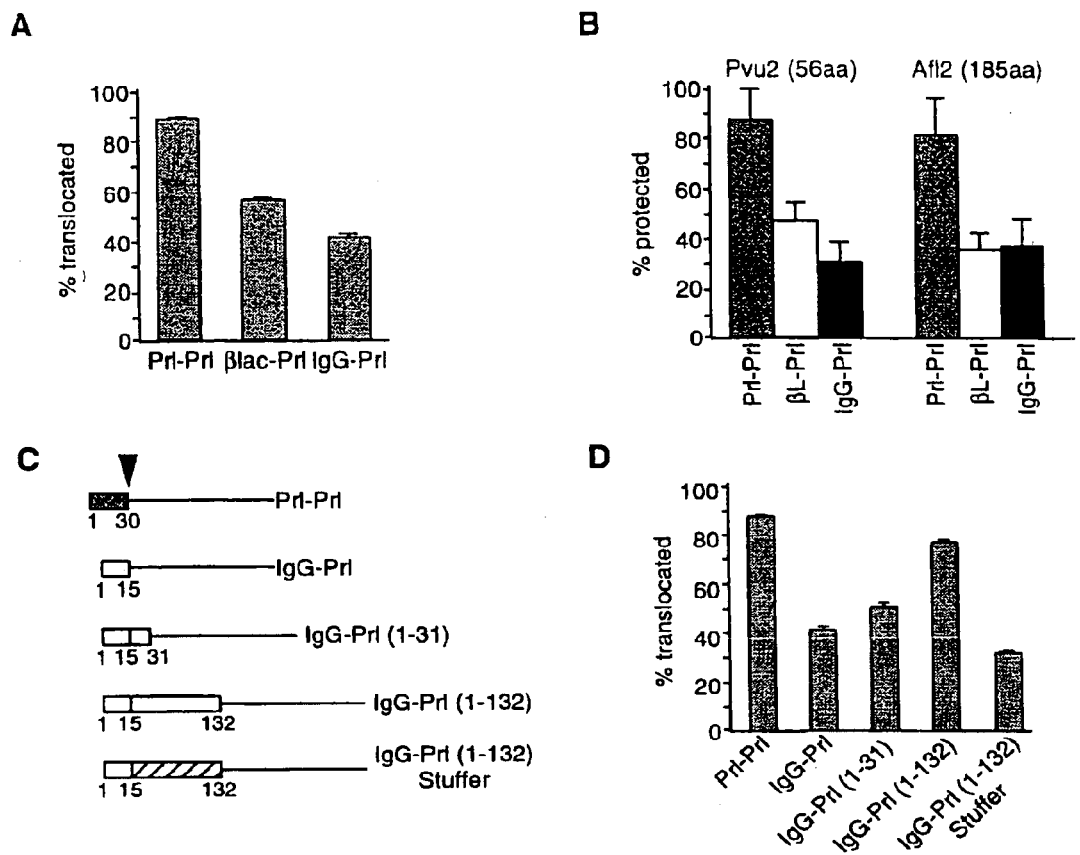

FIG. 17 shows requirement of junctional regulation for successful translocation. FIG. 17(A): The prolactin mature region was fused to either its own signal sequence (Prl-Prl) or those of pre-beta-lactamase (βL-Prl) or pre-IgG heavy chain (IgG-Prl) at the site of signal sequence cleavage. Full-length mRNAs for these substrates were translated in the presence of microsomal membranes and analyzed as in FIG. 17A. For each substrate, the efficiency of translocation was determined by quantitating the percentage of total chains which achieved a processed, translocated state. Each bar represents the mean percent translocation from three trials (+/–SEM). FIG. 17(B): mRNAs encoding Prl-Prl, βL-Prl, and IgG-Prl were truncated at either Pvull or AflII. The number of amino acids from mature prolactin is shown in parentheses. Translated, sedimented chains were analyzed by proteolysis as in FIG. 15B to assess the state of the ribosome-membrane junction. The y-axis plots the mean percent protection of each substrate from PK in three trials. FIG. 17(C): Schematic of IgG-Prl chimeras. Increasing lengths of pre-IgG heavy chain or a non-IgG stretch of amino acids were fused to the prolactin mature region. The site of signal sequence cleavage is shown by an arrowhead. Sequences from IgG are represented by open boxes, Prl mature region sequences by bars, and the non-IgG control sequence by a hatched box. The Prl signal sequence is indicated by a shaded box. Numbers below each construct represent amino acids from pre-IgG heavy chain, the preprolactin signal sequence (Prl-Prl), or the non-IgG sequence (numbers 15–132 of IgG-Prl(1–132)Stuffer) with the initiation methionine as number 1. FIG. 17(D): The substrates shown in FIG. 17(C) were translated in the presence of microsomal membranes and analyzed for the mean percent translocation from three trials as in FIG. 17(B).

Figure 18:
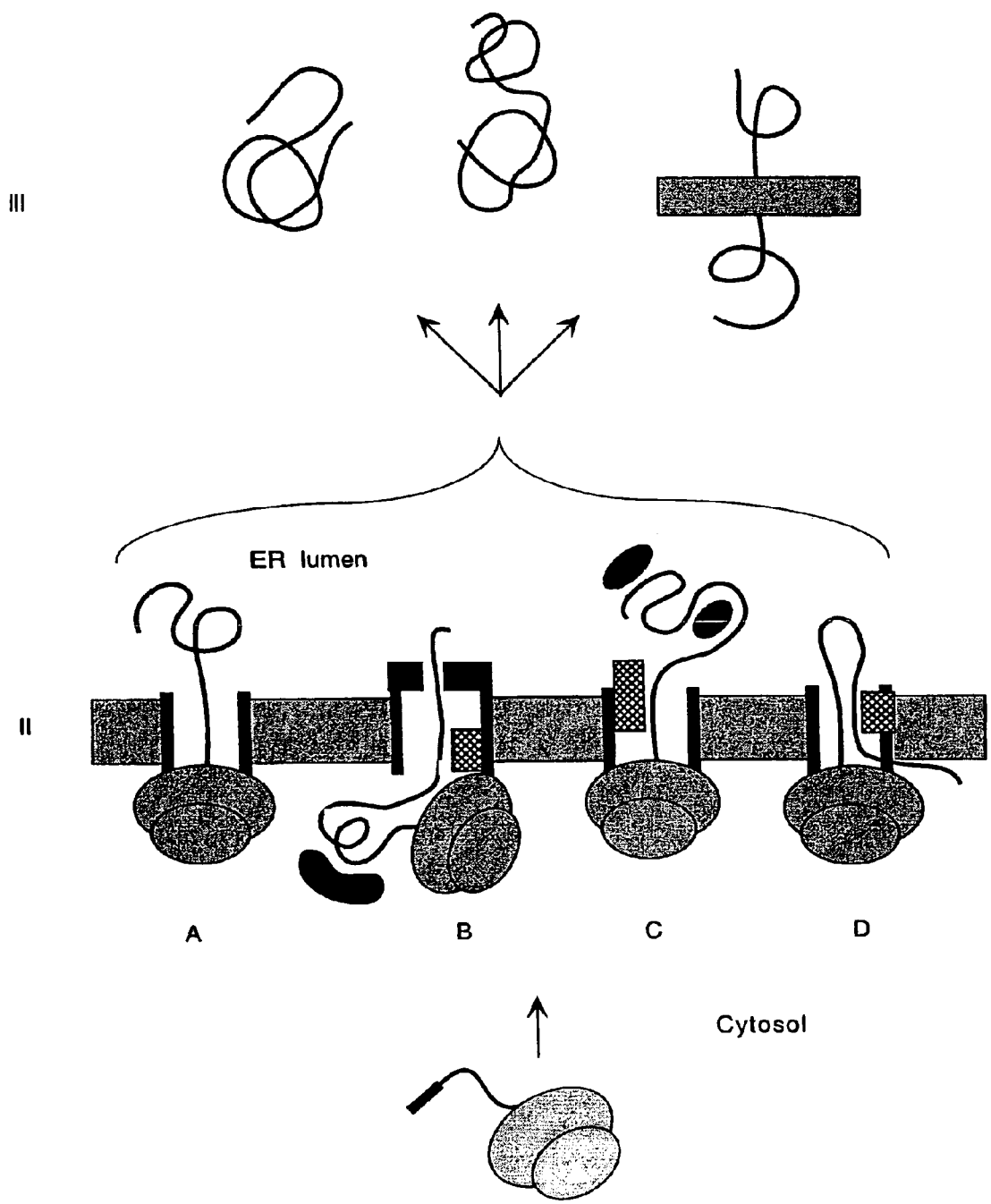

FIG. 18 shows a schematic of how translocational regulation can lead to conformational heterogeneity. Indicated in Roman numerals to the left are the endpoints of three stages of protein biogenesis at the ER: I, the earliest events including targeting; II, the events of translocation per se; and III, the final folded protein. Translocational regulation, of which four forms are indicated as FIG. 18(A–D) in stage II, provides the means by which heterogeneity is achieved among completed, folded proteins (see III), as hypothesized here. Molecular chaperones are indicated by solid ovals, while TrAFs are depicted as hatched rectangles. In FIG. 18(A), the translocon serves as a molecular chaperone. In FIG. 18(B), the translocon forces the nascent chain to initiate folding in a reducing environment, perhaps in association with molecular chaperones or machinery for post-translational modifications. Note that the lumenal gate of the translocon is closed, while that on the cytoplasmic side that makes up the ribosome-membrane junction, is open. In FIG. 18(C), the converse is achieved—a closed cytoplasmic gate and an open lumenal gate, again with the implicit participation of distinct molecular chaperones. Finally, FIG. 18(D) indicates that the action of TrAFs can result in a change in protein topology as well as conformation. First order protein folding is independent of these considerations. Second order protein folding manifests itself in different ways (note different molecular chaperones in FIG. 18B vs C) depending on TrAF action which constitutes the third order level of complexity of protein folding. The final order of complexity of protein folding is due to the regulation of TraAFs by signaling pathways that allow cells to choose between Figures (A–D), for example, in response to a change in environmental or other conditions.

Figure 19:
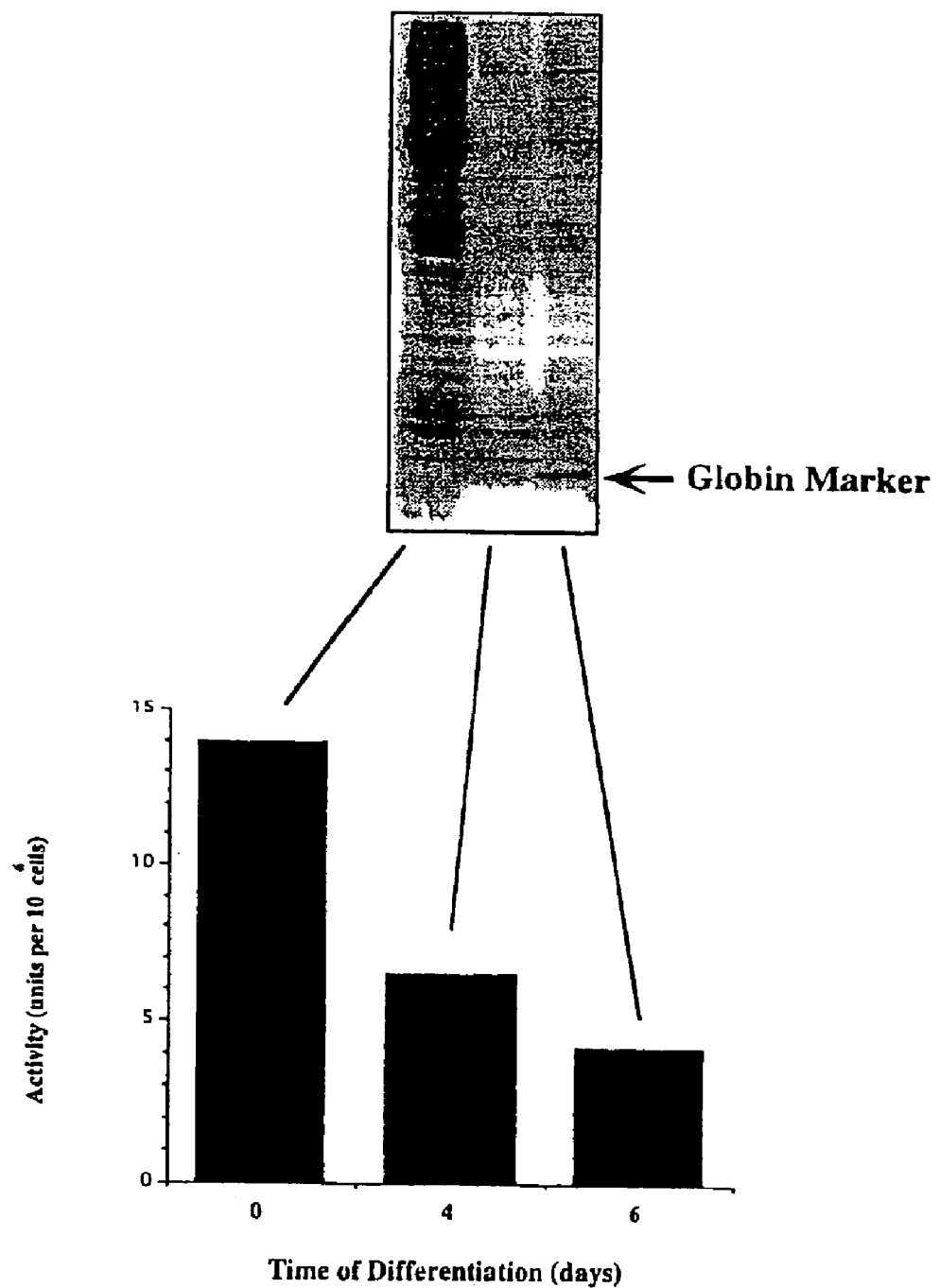

FIG. 19: PrP cDNA was transcribed and translated as described previously (Lopez et al, *Science* (1990 248:226–229) in the presence of cytosolic extract prepared from mouse erythroleukemia cells before and 4 of 6 days after induction of differentiation with dimethylsulfoxide. Thee presence of 35S methionine during the translation reactions allows radiolabelled newly synthesized proteins to be visualized by polyacrylamide gel electrophoresis in sodium dodecyl sulfate (SDS-PAGE) and autoradiography (AR). One unit of activity is the amount of extract needed to change the ratio of PrP topological forms in favor of sec PrP in a 10 µl translation reaction supplemented with dog pancreas microsomal membranes at a final concentration of 5 A280 u/ml. To prepare the cytosolic extracts, cells were dounce homogenized after swelling in 10 mM Hepes pH 7.5 and membranes removed by centrifugation at 100,000×g for 1 hr. As can be seen, cytosols from undifferentiated MEL cells are rich in an activity that promotes secPrP, and that activity is lost upon differentiation of the cells, over time. In this case PrP is serving as a reporter of cytosolic regulatory activities that are likely utilized by several proteins for different endpoints. Note the presence of a globin band in the gel from the 6 day point, indicating induction of globin, a differentiation marker in these cells.

Figure 20:
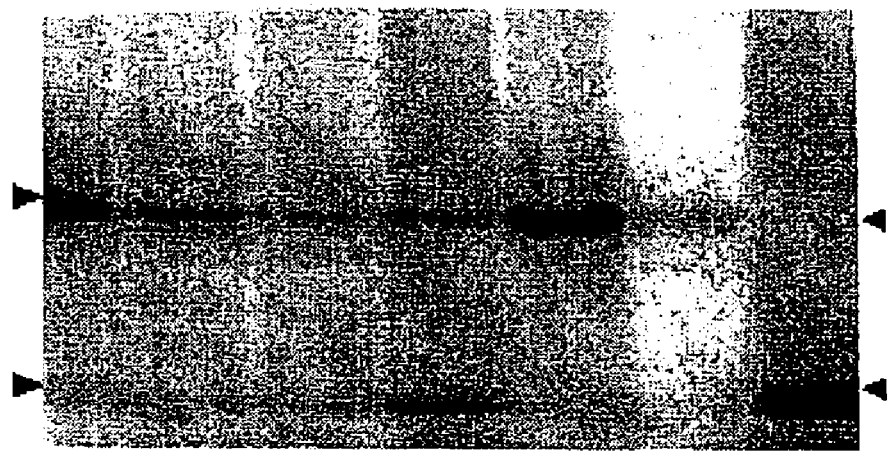
Figure 20:
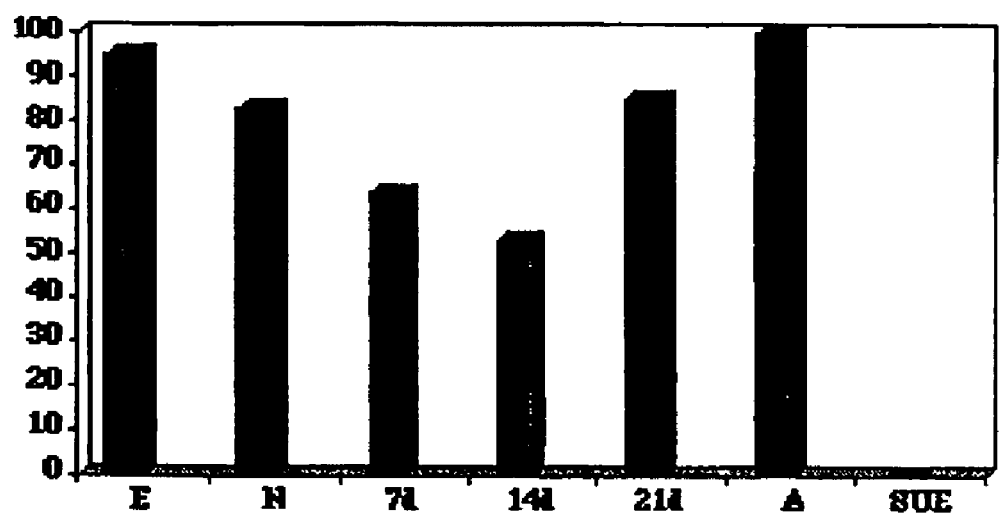

FIG. 20: Transcription and translation of PrP cDNA was performed as previously described in the presence of microsomal membranes from the indicated sources. The products were subjected to protease digestion in the absence or presence of detergent as previously described. Shown are the products of digestion with protease in the absence of detergent, allowing the ratio of Sec-PrP to Ctm-Prp to be readily assessed by SDS-PAGE and AR. E=microsomal membranes from hamster brain on embryonic day 13; N=neonatal hamster brain microsomal membranes; 7d=microsomal membranes from 7 day post natal hamster brain; 14d=microsomal membranes from 14 day post natal hamster brain; 21d=microsomal membranes from 21 day post natal hamster brain; A=microsomal membranes from adult hamster brain; SUE=sea urchin embryo microsomal membranes (which lack TrAF and therefore generate exclusively Ctm-PrP comparable to glycoprotein-depleted fractionated and reconstituted proteoliposomes (Hegde et al., (1998) *Mol Cell* 2:85–91). Upper arrow indicates the position of SecPrP; lower arrow of Ctm-PrP. Graph below is quantification of the ratio of secretory PrP to total PrP for each of the indicated lanes above. What is demonstrated is that membranes from different tissues and species, and from the same tissue and species at different times in development, can have radically different TrAF activities, consistent with the hypothesis that translocation is an important site of regulation of protein biogenesis, and that trans-acting factors contribute to translocational regulation. In this case, prion protein is being used solely as a reporter of TrAF activity. The same principle applies to all genes for which translocational regulation may be found.

SUMMARY OF THE INVENTION

Methods and compositions are provided for producing proteins of varying topography and/or topological species, providing chimeric proteins, identifying specific agents involved with the formation of topographical and/or topological species, model in vitro and in vivo systems, and methods for identifying topographical and/or topological distinct proteins. Proteins of varying conformation are produced by varying the signal sequence, replacing the wild-type signal sequence with sequences of known mechanism, selectively including translocon associated proteins in an in vitro translocation model system, employing modified lysates with microsomes for investigating and producing conformationally distinct proteins, for producing and employing knock-out and mutant small laboratory mammals resulting in modulation of the topographical production of target proteins and elucidating physiological mechanisms.

DESCRIPTION OF THE SPECIFIC EMBODIMENTS

Methods and compositions involving elements of the protein translocating system are employed in elucidating components of the system and their function, modulating folding of proteins using chimeric genes employing an unnatural signal sequence to provide "conformers," (proteins having at least substantially the same amino acid sequence, but different physical topology or topography). By topology is intended the different placement of the protein, e.g. C-cytosolic as compared to N-cytosolic, and topography intends change in external conformation or shape, identifying conformers, providing in vitro and in vivo systems for these purposes, and identifying compositions that modulate protein conformation during translocation. Topography as used herein refers to proteins of substantially the same or similar amino acid sequence but different three dimensional shapes due to differences in folding/conformation. As used herein, polypeptides of substantially the same amino acid sequence are those with conservative amino acid substitutions (i.e. a small or large side chain for a small or large side chain, respectively; or an acidic, basic, polar or hydrophobic side chain for an acidic, basic, polar or hydrophobic side chain, respectively), that do not alter the protein conformation or topology. Methods for identifying the multiple gene products that regulate signal sequence mediated selection of folding funnels during protein biogenesis also are provided, using a reticulocyte lysate fractionation scheme. The methodology for fractionation of translation extracts and fractionation of solubilized membranes with reconstitution of subfractions containing or missing particular trans-acting activities, offers several advantages over existing systems. The process can be readily expanded to a large scale; the materials required for the fractionation are either inexpensive (common chemicals) or reuseable (centrifuge tubes, ion exchange resin); and the final products have a long shelf life when stored appropriately.

This fractionated system offers several advantages over the currently available RRL, including: We have demonstrated that simply supplementing an S-100 fraction from Xenopus oocytes with RRL ribosomes results in translation efficiencies more than an order of magnitude greater than previous oocyte translation systems (2). Such an oocyte system can be used to study oocyte specific events such as translational repression of developmentally regulated factors; and also, it appears that the ribosomes contained in the rough microsome preparation from dog pancreas are highly active in restoring translation to the DEAE fraction. Thus, translocation events can be studied in an essentially homologous system in which dog pancreas ribosomes are translating and translocating proteins across dog pancreas membranes. Subtle and regulated interactions between ribosomes and translocon proteins may be more faithfully reproduced in a homologous system versus a heterologous system.

This system can be readily adapted to other translation systems such as the wheat germ translation system, or Xenopus oocyte translation system. In some cases, the fractionated system results in an enormous increase in the translation efficiency (see above). Furthermore, the ability to mix and match components from multiple such fractionated systems allows tissue specific events involved in the biogenesis of certain proteins to be studied. This is potentially useful for the identification of factors, by complementation, involved in such tissue specific events. Examples of such tissue specific differences have been documented (Wolin and Walter, *J. Cell Biol* (1989) 109:2617–2622; Lopez et al., *Science* (1990) 248:226–229).

The proteins of interest are proteins, which have a signal sequence and are subject to processing in the endoplasmic reticulum. Numerous signal sequences have been identified from different proteins and appear to be capable of operating conjugated to a broad range of unnatural proteins. The signal sequences are usually N-terminal, but may be internal to the protein or C-terminal. Signal sequences are selected from proteins that are known to have a specific mechanism for translocation affecting the conformation of the product or may be synthetic, where the translocational effect is known or determined. It is now known that the signal sequence affects the conformation of the protein that is translated in conjunction with the translocon. Without being bound by any theory, the signal sequence directs whether the ribosome forms a tight, loose or intermediate junction with the endoplasmic reticulum (ER) and the selection of the channel and accompanying processing proteins through which the translated protein is translocated and processed. For example, replacing a signal sequence of a protein with a signal sequence from preprolactin results in a tight junction., while the signal sequence from pre-β-lactamase provides a loose junction. Proteins which provide tight junctions include: growth hormone; and loose junctions include: immunological heavy chain and yeast alpha-factor; and intermediate junctions include ductin, calreticulin, PrP, angiotensinogen and MDR-1, where the division between the different conformers may be attributed to a variety of mechanisms. (See, for discussion, Hegde and Lingappa, (1996) *Cell* 85, 217–228 for a discussion of the effect of the ribosome-membrane junction.) For a general discussion of the mechanism of translocation, see, for example, Ellgaard, et al., (1999) *Science* 286, 1882-1888; Wickner, et al., (1999) *Science* 286, 1888–1893; and Ibba and Soll, (1999) *Science* 286, 1893–1897.

Signal sequences may be rated by using a lysate competent for expression, microsomes and proteinase K. The degree of proteolysis occurring with different signal sequences and a common gene is indicative of the nature of the junction of the ribosome with the ER. By using signal sequences having different degrees of junction tightness, the conformation of the resulting protein can be modified. These different conformers may be used in a number of ways. The conformers may be used for the production of antibodies, either antisera or preferably monoclonal antibodies. The antisera and antibodies are prepared in conventional ways using the different protein conformers to immunize a host, usually a mouse in the case of monoclonal antibodies, with or without an adjuvant, followed by additional injections of the protein at biweekly or longer intervals and monitoring the level of antisera. For monoclonal antibodies, splenocytes may be isolated, immortalized and screened. Those hybridomas which produce antisera which can distinguish between the conformers are expanded. A library is produced of antibodies that distinguish between the two conformers. The antibodies may then be used to isolate each of the conformers and assay for the different conformers in hosts, using physiological samples appropriate to the nature of the protein.

Signal sequences may also be rated by analysis of crosslinking patterns generated when truncated transcripts encoding those signal sequences at the 5' end of the authentic coding region of interest are expressed by cell-free translation and subject to chemical crosslinking including but not limited to lysine and cystiene specific cleavable and uncleavable crosslinkers, with analysis of the crosslink patterns by immunoprecipitation and polyacrylamide gel electrophoresis in sodium dodecyl sulfate and subsequent autoradiography.

Different conformers may be screened by employing matrices of different oligopeptides and/or oligonucleotides. See, for example, U.S. Pat. Nos. 5,631,734; 5,856,102 and 5,919,523. These matrices are available commercially and can be prepared in relation to a particular binding pattern. In this way, one can add a physiological sample and see which of the conformers are present and estimate the amount of each. One may also use the matrix to isolate particular conformers by their binding affinity to the matrix. The matrix and antibodies may be used in conjunction to confirm the other assay, isolate the conformer, used together in the same assay. In assays by themselves or in conjunction with other affinity binding assays, the antibodies may be labeled with a detectable label, e.g. fluorescer, luminescer, phosphorescer, enzyme, radioisotope, and the like. Numerous protocols are available for defining specific epitopes, by which the conformers may be distinguished. In some instances, it may be desirable to use two or more antibodies, where the conformer may be defined by steric inhibition of binding, different affinity constants, or the like.

By virtue of the fact that the conformers can be distinguished by oligomers, particularly of oligopeptides, these oligopeptides may serve for identifying the different conformers. The oligopeptides can be used in competitive assays for identifying other oligopeptides which compete for the site or other compounds, particularly small organic compounds, natural or synthetic, of less than 5 kDal, usually less than about 2.5 kDal, which bind to the conformer. These compounds may then be used in turn to identify other compounds having greater affinity for the site. In this way drugs may be identified that are specific for one conformer, as compared to other conformers. The various binding entities may be used in assays, where the entity may be labeled to identify binding to the conformer. The assays may be homogeneous or heterogeneous.

If desired, one may use random mutations of the wild-type and/or chimeric gene to express the resulting gene. The protein may be analyzed for similarities and differences with the parent gene. Where the effect of the mutation is to change the conformer from one conformation to another or to change an epitope, as determined by antibody binding. Or to generate differences in crosslinking pattern or conformation as scored by altered reactivity to chemical modifying agents under non-denaturing condtions, including but not limited to N-sulfobiotin, trinitrobenzenesulfonic acid (TNBS), N-ethyl maleimide (NEM). Genes and the proteins, which they express from human patients or animals, where a mutation is naturally occurring or a result of mutating a gene, may be compared with the randomly mutated gene and its expression product in a mammalian host. In this way, disease states resulting from mutations that lead to different conformers may be diagnosed and treatments developed.

The conformers can be used for biomedical purposes in aiding in the diagnosis and treatment of patients. The conformers serve to differentiate between individual hosts, who produce the conformers in different ratios, normally or under different environments. One of the environments is the presence of a compound, particularly a drug, and the binding affinity and/or modulation of activity of a target physiologically active compound, usually a protein, such as a membrane receptor, channel, enzyme, transcription factor, housekeeping protein, cytoskeletal protein, membrane protein, and the like. The conformers may be mobile or immobile proteins, being bound to membranes or free in solution. A compound would be mixed with the different conformers, in the same or different vessel, and the binding of the compound to the conformer determined. The determination may be made in a variety of ways, either competitive or non-competitive. The amount of compound remaining in the solution may be determined, where a reduction in amount would be indicative of the binding of the compound to the conformer. Alternatively, a labeled compound which binds to the conformer may be used, where interest in binding is as to a particular region of the protein, such as in the case of enzymes and receptors, as well as other proteins where particular sites are associated with biological activity, e.g. G-proteins, transcription factors, DNA binding proteins, etc.

The conformers are also useful in determining differences in activity in relation to their physiological activity. The binding affinity for their binding partners can be determined in assays, either homogeneous or non-homogeneous, which allows for evaluation of the level of activity of a mammalian host in relation to the proportion of the two conformers. Again, numerous protocols are available for detecting binding between a ligand and a receptor or two or more proteins involved in complex formation. The two proteins may be labeled with a fluorescer and an energy receptor, so that binding of the two proteins together would reduce the level of emission at the wavelength of the fluorescer and increase the emission at the level of the energy acceptor. Alternatively, one may bind one of the proteins to a surface and the level of binding of the other protein to the bound protein determined by having the second protein labeled. Alternatively, one may bind each of the proteins to different particles, where one particle produces a compound, which activates the other particle, such as LOCI. Where the labeled entity is small, such as an oligomer or small organic molecule, a fluorescer may be used as the label and fluorescence polarization employed for detection. Illustrative of assays are the assays described in U.S. Pat. Nos. 5,989,921; 4,806,488; 4,318,707; 4,255,329; 4,233,402; and 4,199,559.

In determining the presence of conformers when screening physiological samples, the samples may be blood, cells, csf, saliva, urine, hair, etc. The sample may be subject to pretreatment, such as adding citrate to blood, coagulating and separating erythrocytes, dilution, extraction, etc. Thus, the conformers may be identified as being associated with particular indications, which may relate to diseases, response to drugs, physical performance, cellular degeneration, apoptosis, etc.

Illustrative of the power of the subject invention is the investigation of prions. It is found that by varying the signal sequence one can obtain the natural conformation $^{sec}$PrP, and two other conformations, $^{Ntm}$Prp and the neurodegenerative $^{Ctm}$Prp, in varying amounts. This aids in the determination of the mechanism of the change in the proportion of formation of the neurodegenerative form as compared to the wild-type form. In an analogous manner, one may vary the signal sequences for other proteins having signal sequences, where the protein is suspected of being associated with a diseased state or lowered performance. One could then determine whether the protein can be produced in varying conformations. If different conformers are found, as described above the presence of the different conformers is established in healthy normal patients as compared to patients who have the disease or reduced performance. Drugs would then be screened as described above against the undesired conformer.

In addition, by using different signal sequences one can investigate the basis for the change in proportion between the desired conformer and the undesired conformer. In conjunction with, in addition to or in place of, one can use in vitro lysates for investigating the role of ER associated proteins with the formation of the conformers. Microsomes are prepared lacking all but the essential proteins for translocation. The individual proteins may then be replaced individually or in combination to determine the effect of the presence of the protein(s) on the formation of the conformers. Once the protein(s) involved in the formation of the conformers is determined, one can screen healthy and abnormal patients for the presence of the protein(s) involved in the formation of conformers and determine the presence of mutations or different conformers. In this manner, one not only elucidates the mechanism by which proteins fold in the translocon, but also establish new targets for therapies.

For the cell-free protein translation mixture, various systems may be employed (Erickson and Blobel, *Methods Enzymol.* 96:38–50 (1983); Merrick, *Methods Enzymol* 101:606–615 (1983)). Illustrative are wheat germ extract and rabbit reticulocyte extract, available from commercial suppliers, e.g. Promega (Madison, Wis.), as well as high-speed supernatants thereof. Other references include U.S. Pat. Nos. 5,998,163; 5,998,136 and 5,989,833. Such systems include, in addition to the cell-free extract containing translation machinery (tRNA, ribosomes, etc.), an energy source (ATP, GTP), and a full complement of amino acids. Methods known in the art are used to maintain energy levels sufficient to maintain protein synthesis, for example, by adding additional nucleotide energy sources during the reaction or by adding an alternative energy source, e.g., creatine phosphate/creatine phosphokinase. The ATP and GTP present in the standard translation mixture will generally be at a concentration in the range of about 0.1 to 10 mM, more usually 0.5 to 2 mM. Generally, the amount of the nucleotides will be sufficient to provide at least about 5 picomolar of product, preferably at least about 10 picomolar of product.

Lymphocytes also form PrP and may be used as a screen for the effect of agents, e.g. compounds as candidate drugs or as a screen for response of an individual to changes in the environment or physical insults. The lymphocytes would be subjected to a change in the environment, which could be a chemical change, e.g. addition of a compound, a physical change, e.g. change in pH, etc., where the sensitivity of the particular cells to the change would be determined as a measure of the propensity of the person to respond to the environmental change by changing the nature of the PrP. By determining the response to changes in the environment, which could include pollutants, pesticides, etc., one can determine whether the compounds are a general threat or only affect idiosyncratic people. The cells may also be used to determine whether a patient who is symptomatic for a neurodegenerative disease has a Ctm-PrP related disease by determining the presence and/or level of Ctm-PrP in the lymphocytes as compared to normal individuals. Numerous assays may be employed as described herein to determine the presence and level of Ctm-PrP. By detecting a propensity for neurodegenerative disease, the patient could be directed away from activities or exposure to compounds that might increase the probability of the neurodegenerative disease. In addition, the effect of compounds on Ctm-PrP may be used as a substitute in relating the activity to other diseases that respond in an analogous way. The cells may also be used for individual patients to evaluate the response of the individual to various drugs, determining the effect of the drug on the production of Ctm-PrP As described above, many proteins have-different translocational outcomes. Proteins known to have alternatives in the translocational pathway, such as existing in two different conformers, the presence of different methionines that may be selected as the f-Met, resulting in a different signal sequence, having hydrophobic regions of from about 15 to 20 amino acids in the chain, which can be putative transmembrane sequences, but are available as secreted proteins or are transmembrane that are secreted can be used as markers for the effect of compounds on translocational outcome. Illustrative proteins include ductin, calreticulin, MDR-1, and PrP.

Numerous proteins are associated with the ER in the process of translocation, frequently being part of the ER and associated with the channel through which the nascent protein is transported to the ER lumen. These proteins include the ribosome, proteins of the signal recognition particle (SRP), the heterotrimeric Sec61complex with α, β, and γ-subunits, translocating-chain-associated membrane protein (TRAM), signal peptidase (a complex of five proteins), oligosaccharyl transferase (a 3-protein complex), ER lumenal proteins, including BiP, GRP94, calnexin (CNX), ERGIC-53, protein disulfide isomerase (PDI), Erp57. Erp72, chaperones, such as Hsp 90, hsp 47, Hsp 60 or GroEL family, Hsp 70 or DnaK family, Hsp 100 or Clp family, and heat shock cognate 70, tapasin, microsomal triglyceride transfer protein, protective protein/cathespin A, β-catenin, egasyn, co-chaperones, such as proteins from the DnaJ family, enzymes, such as uridine 5'-diphosphate (UDP)—glucose:glycoprotein glucosyltransferase (GT), glucosidase II, prolyl-hydroxylase and carboxylesterase.

The ancillary proteins associated with the ER and translocation of the translocation product may be removed from the lysate by methods described in the literature. (Gorlich, et al., (1992) *Nature* 357, 47–52; Gorlich and Rapoport, (1993) *Cell* 75, 615–630; and Hanein, et al., (1996) *Cell* 87, 721–732.

By varying the signal sequence in proteins of interest, one can prepare genes for expression in mammalian hosts. Methods of replacing a DNA sequence to provide a chimeric gene are legion today. See, for example, Sambrook, et al. (1989), A Laboratory Manual, Second edition, Cold Spring Harbor Press. Briefly, the DNA for the gene is isolated knowing the amino acid sequence and using degenerate probes. The DNA sequences, which bind to the probes, are isolated and sequenced to see the presence of a sequence coding for the protein of interest. If one wishes to avoid the presence of introns, the mRNA may be isolated, reverse transcribed and amplified using PCR. The signal sequence in either situation may be replaced with a different signal sequence by amplification using one pair of primers, with one primer having a signal sequence at its 5'-terminus joined to a sequence complementary to the sequence of the gene contiguous with the native signal sequence the other primer complementary to the first primer. A second set of primers will provide the other terminus of the DNA sequence. Depending on the size of the gene, one may select a convenient restriction site for linking the modified 5'-terminus DNA with the remainder of the coding sequence. Various techniques are available and each gene will have an obvious selection of protocols to enhance the convenience of the particular synthesis.

Once the gene is produced it may be introduced into one of numerous commercially available vectors and cloned and/or an expression vector may be employed having a transcriptional regulatory region 5' of the sense strand to provide for expression. By using mammalian cells, the conformers from the different constructs can be produced and isolated and assayed as described above. In this way, significant amounts of the different conformers may be isolated.

In an initial stage, one may wish to concentrate the conformers using different separation techniques, such as HPLC, capillary electrophoresis, affinity chromatography, etc. The initial separation may solely serve to enhance the concentration of the conformers in a particular fraction or may provide for separation of the conformers. In the former case, one would need further separation of the conformers, using techniques, which have been described above. Various separation media may be employed, involving ion exchange, sieving media, affinity media, etc., using different eluents to establish procedures for separation and isolation of the different conformers. Various procedures have been developed and each set of conformers will use protocols that optimize the separation with minimum denaturation. These protocols may be readily identified by those of skill in the art of protein purification. The purified conformers may then be used for assays, for x-ray crystallography, to identify differences in structure, the amino acids associated with the different epitopes, the interactions with proteins with which the wild-type protein is associated, as well as other proteins to which the conformer may bind, and the like.

Once having the gene for the chimeric protein, the gene can be used in gene therapy, mutating laboratory animals, random mutation to determine the effect of mutations on folding, in expression constructs and single cell or organism host for large scale production of the protein, and the like. Laboratory animals include rodents, lagomorpha, birds, canine, feline, porcine, etc.

In some instances, one may create viral constructs, where the chimeric gene is introduced into a viral carrier for introduction into cells, either randomly or where the virus has a tropism, into cells for which the virus is tropic. Where the gene has a beneficial effect, even in the presence of the other conformer, the presence of the construct may serve to alleviate the symptom resulting from the native conformer. Alternatively, the introduction of the non-native conformer will allow an evaluation of the effect of the non-native conformer on the physiology of the cell, tissue, organ and host.

Of particular interest is the introduction, preferably replacement of the wild-type gene with the chimeric construct comprising the wild-type structure and a different signal sequence that is known to result in a different conformer. By using homologous recombination with germ cells or a nucleus that is subsequently transferred to a germ cell, one can provide for the expression of the desired conformer(s). Where heterozygosity is involved, the progeny having the chimeric gene may be mated to obtain homozygous progeny. In this way, one can investigate the role of the conformer(s), whether the location(s) to which the protein is transported changes, the effect of such variation in location, the effect of the different epitopes or topography on the function of the protein, and the like. In addition, the chimeric mammal may be used to screen compounds for their biological effect on the conformer, so that drugs which are directed to a particular indication, which involves the conformer, either directly or as a result of the conformer being in the pathway, can be evaluated. The animal models may be used to differentiate the effects on the wild-type conformer and other conformers that can be formed.

In situations where the non-native conformer is a dominant negative allele, the loss of activity can be monitored as to the effect on the physiology of the host. The effect on the host can be compared to disease states, where similar indications are observed. Treatments can then be evaluated by employing drugs having known function associated with the indication, compounds known to bind to the wild-type allele or other treatment to evaluate the effectiveness of the treatment. Cells having the unnatural conformer may be screened for the effect of the unnatural conformer on the expression of other proteins. By converting the mRNA to cDNA of such cells, one can by using various subtraction techniques known in the literature, between the cells without the unnatural gene and the cells with the unnatural gene, determine the effect of the unnatural gene on the expression of other proteins. Alternatively, one may express the various proteins and compare electrophoretic, mass spectrophotometric or HPLC patterns to determine if the different conformers affect the expression pattern of the host.

Following the procedures described in the above description and in the experimental section, or other functionally equivalent procedures, the subject invention allows for investigation of diseases associated with the prion protein and analogous diseases, particularly diseases associated with topological modifications as in Alzheimer's disease. As shown, by preparing expression constructs for expression of the native PrP, the Ntm-PrP and the Ctm-Prp, one can modify cells and animals to produce the different forms of the protein. In this way, one can study in culture and in vivo the effect of the addition of various candidate agents and determine the change in the formation of the different conformers in the presence of the agents in culture and in vivo. The subject proteins allow for the controlled presence of the different conformers and a study of the etiology of the disease, the other entities involved in the etiology of the disease, by doing expression analysis of the effect of the different conformers on expression in the same and different cells and on the physiology of the host. Mouse models may be developed with the construct in the presence or absence of the native PrP gene, since the host gene may be knocked-out and replaced with the chimeric gene. Alternatively, mutations may be introduced into the PrP gene that result in a modification of folding and a modification in the dependence on or interaction with proteins associated with translocation. Thus, the signal sequences, either native or chimeric to the gene, may be mutated and the effect on translocation-related proteins determined.

Uses of the Invention

The invention finds use at the molecular, cellular and organismal levels (i.e. in elucidating, diagnosing or treating a disease). Following are provided specific applications.

1. Using the described invention, it would be possible to manipulate antibodies to increase their functions and uses. By signal sequence replacements, alone and in conjunction with fractionated and reconstituted or variant membrane and cytosols in cell-free translation systems, the pathway of folding of an immunoglobulin could be altered in either subtle or profound ways, without actually changing the amino acid sequence of the final product itself. Thus, it would be possible to achieve variant immunoglobulins in which the binding constant were increased or decreased incrementally, and immunoglobulins with changes in their effector functions (e.g. the binding specificity of their Fc region). Current approaches to achieve these ends (e.g. by site-directed or random mutagenesis of the authentic immunoglobulin chains) have the disadvantage of changing not only the folding pathway but also the primary structure of the molecule itself. Our approach would, in effect, dissociate this two types of changes, allowing one without the other, with diagnostic and/or therapeutic utility. The signal sequence variations could also be applied to transfected mammalian cells, allowing medium to be harvested and screened for conformational and functional differences.

2. Most hormones, cytokines, and growth factors have been implicated in a wide range of functional behaviors, and in some cases, activation of multiple signaling pathways. For example, leptin, first discovered as a hormone that signals satiety, has been found to serve as an independent central regulator of bone density, and to be implicated in wound healing and control of blood pressure. Some of these functions clearly occur in the absence of the others, and most obese individuals are leptin resistant, without having disorders of bone density, suggesting that the leptin they make is not able to serve the satiety promoting function, but is able to function in maintenance of bone density. The conventional assumption has been that this sort of heterogeneous action is achieved through diversity in receptors or receptor function. However, diversity of ligand conformation, as demonstrated in the examples from PrP and prolactin shown here, could account for some or even most of the heterogeneity of outcomes, in the case of leptin.

By allowing individual conformers to be identified, and pharmaceuticals to be developed to increase or decrease the expression of individual conformers, or to block action of one conformer or another, it should be possible to affect gene expression in ways that promote some functions of hormones over others. It should also be possible to stratify patients into subsets based on the mix of conformers that is manifest with their particular genotype and phenotype. This would in turn, allow different treatments to be administered to different individuals taking into account the mix of conformers they are expressing at that particular point in time, using different pharmaceutical agents designed or shown to be most efficacious for a particular conformer mix or other conformer-related subset.

Thus, in the case of leptin, swapping of signal sequence, and synthesis in various combinations of translation systems containing fractionated cytosol and fractionated and reconstituted or variant membranes, and subsequent screening programs should make it possible to generate forms of leptin that would promote bone density without affects on satiety or wound healing, or vice versa. Likewise, forms of leptin that would be more active at appetite suppression and thereby overcome leptin resistance, the most commonly observed phenotype in obese humans, could be generated. Conversely, small molecule pharmaceuticals could be developed, by screening for their effect on individual subsets of leptin conformers, or for their affect in altering the mix of leptin conformers secreted. Thus it would be possible to develop drugs that have conformer-specific or selective effects, thereby blocking or enhancing the effects of conformers, or blocking or enhancing the body's ability to make a particular mix of conformers. Half-life, association with other molecules, secretion kinetics are parameters besides affinity for particular receptors that could be altered by signal sequence manipulations without altering in any way the sequence of the mature, authentic protein. This approach would apply also to secretory and integral membrane enzymes, where substrate turnover, rather than receptor affinity is the relevant functional parameter.

3. This approach can be combined with transgenic technology to introduce variant genes differing in their signal sequences, into wild-type and knock-out mice (lacking an endogenous gene). In this manner it will be possible to screen for functions of complex secretory and integral membrane proteins that currently are not known. Thus it is known that 95% of the wild-type Cystic Fibrosis Transmembrane Regulator (CFTR) is degraded immediately upon synthesis. The conventional assumption is that this represents "errors" in biogenesis. An alternative interpretation, for which the present invention has utility, is that these 95% represent the sum total of many alternative conformations that are not needed by the cell at one particular time, but may be rescued from degradation at particular times in development. Since the signal sequences of CFTR are not cleaved, the goal of altering folding without introducing mutations must proceed exclusively by regulation in trans rathe than in cis. Thus, expression of CFTR in translation systems complemented with fractionated and reconstituted or variant membranes and fractionated and reconstituted cytosol, as claimed, would enhance one versus another conformation, which would in turn be scored and catalogued by monoclonal antibody reactivity, chemical modifications, crosslinking and other properties, and then introduced into transgenic animals and screened for novel phenotypes and disorders. Similar approaches can be taken for each of the channel forming and receptor forming membrane proteins, including both single and multispanning with respect to the ER and/or other internal and/or plasma membranes.

4. The most difficult to currently treat diseases in humans are disorders of signaling as typically manifest by hormone, growth factor, cytokine and receptor resistance (also known as desensitization or down regulation). Many different mechanism of resistance have been identified, whether most cases of most diseases are due to the mechanisms identified or due to other as yet unknown mechanisms remains to be determined. Based on our studies with PrP as summarized in our published and unpublished work, we believe that conformational dysregulation (the wrong mix of conformers being made or being allowed to exit from the ER) is a central mechanism of disease pathogenesis. This can be demonstrated by raising monoclonal antibodies to secretory proteins and demonstrating that individual subsets of the secretory proteins are present (or absent) in a disproportionate manner in a disease state or in subsets of patients with a disease state. The major genes for the major diseases afflicting humans include a large number of secretory and membrane proteins, which could be screened for the involvement of conformational dysregulation in their pathophysiology. Diabetes, hypertension, hyperlipidemia, obesity, osteoporosis, degenerative joint disease, cancer, Alzheimer's disease, and psychiatric disorders are just a few examples already implicated in this fashion.

Application of the Invention to the Research and Treatment of Disease

As listed above, a number of important medical conditions involve genes for which conformational regulation is likely to be an important dimension of physiological and pathophysiological function. Here it is described how the invention is applied to better understanding specific diseases.

First, key disease-related genes that are secretory and integral membrane proteins would be analysed in cell-free systems and in transfected mammalian cells, to characterize the class in which their signal sequences fall. The conformational heterogeneity of the native proteins will be catalogued both in vitro and in vivo, including in samples from mice and humans (e.g. from blood), if available, using monoclonal antibodies, chemical modifications and co-association with other proteins inside the cell and in the medium, as the means of scoring conformation.

Second, attempts will be made to skew the conformational mix synthesized, allowing minor and transient conformers to be magnified and stabilized and therefore more readily detected and characterized, so that they can be distinguished from the normally dominant conformers. This can be done in two general ways, namely by swapping signal sequences that are cleaved or by expressing the proteins in fractionated and reconstituted systems that modify the native conformer mix through actions (or their absence) in trans.

Third, once the mix of conformers that define the key disease-related proteins has been characterized, samples from patients representing the diversity of the natural history and phenotypic classes of the disease in question, will be screened and categorized with respect to the heterogeneity of conformers of these proteins observed. From this analysis it will be possible to identify i) the conformers implicated in disease; ii) changes in conformer mix that precede actual development of disease, iii) changes in conformer mix that stratify individuals with respect to disease progression, complications and other aspects of natural history, including increased or decreased risk of drug efficacy, side effects and other reactions. Note that these are all goals of conventional proteomics programs which will be missed by those programs because they are not aware of the evidence, submitted in support of the subject invention, for conformational heterogeneity of proteins. Hence they are not looking for alternate conformers of the protein in question. Furthermore, without the subject invention, there are currently no means of systematically identifying, magnifying, and characterizing these changes in conformers, without which it is impossible to determine their distribution or significance in populations at risk of, or afflicted with, particular diseases.

Fourth, with a variety of valuable information on disease association of conformers in hand from 1–3 above, it is possible to develop assays as outlined previously to screen for agents that modify the conformer mix in a way that minimizes undesired conformers and maximizes those that are protective or not associated with disease progression, drug toxicity, etc. Likewise, agents that block undesired conformers selectively, or that enhance the action of desired conformers can be sought through high throughput screens of large compound libraries, as well as through conformer-specific rational drug design.

Specific Applications to Some Major Diseases are Outlined Below.

Diabetes mellitus: The key genes for insulin, the insulin receptor and the many members of the family of glucose transporters all have cleaved or uncleaved signal sequences that make them amenable to this analysis. Furthermore, a key pathophysiological process impacting on patient care is the syndrome termed insulin resistance. Usually this is attributed to disorders in receptor function, but in most cases, the basis for the disorder is unknown, and the possibility that the disorder could derive from the ligand rather than the receptor, cannot be ruled out. In this case, the ligand is insulin, and the aberrant conformation that impairs insulin-mediated signaling could be a property of either insulin or the insulin receptor or individual members of the family of glucose transporters, which could be identified in the manner described. Finally, the huge heterogeneity of individual phenotype at any given time, and in natural history over time, which has remained elusive despite massive research efforts directed at conventional genomic and proteomic analysis, is strongly suggestive of disordered conformatics, amenable to the subject invention.

Hypertension: A number of key genes in control of blood pressure encode secretory and integral membrane proteins including the epithelial sodium channel (EnaC), angiotensinogen, the angiotensin receptors, renin, the enzymes of steroid biosynthesis involved in synthesis of aldosterone and other steriods, and the alpha and beta adrenergic receptors, to name a few. The pathophysiology of hypertension remains largely mysterious, hence the possibility that conformer dysregulation plays a role in its etiology and pathogenesis cannot be excluded in any way. Clinical epidemiological and observational studies clearly indicate that patients are heterogeneous not only with respect to the nature of their hypertension-inducing state (e.g. salt sensitive vs salt insensitive; increased sympathetic activity, etc.) but also with respect to their sensitivity to individual classes of drugs, side effects of those drugs, and ability to tolerate the drugs.

Obesity: The key genes involved in the control of obesity, including leptin and its receptors, and the various obesity related genes identified to date including the melanocortin and mahogany receptors, the agouti protein, etc. all contain cleaved or uncleaved signal sequences. Furthermore, most obese individuals are leptin resistant, consistent with the hypothesis that conformer differences of leptin mediate its diverse physiological functions (e.g. in satiety, maintenance of bone density, promotion of wound healing, and regulation of blood pressure).

Cancer: Conceptually, cancer is a disorder of signaling pathways involved in cell growth and proliferation and the physiological controls over these processes, including a host of diverse apoptotic triggers and antiapoptotic factors. Many of these are secretory or membrane proteins with cleaved or uncleaved signal sequences. In many cases, cancer can be affected, both positively and negatively, by a host of secreted growth factors and cytokines, which also generally have signal sequences. A host of data supports the notion that many of these factors are multifunctional, or more precisely, are associated with both promoting and inhibiting particular signalling pathways. A present conundrum in the field is understanding how one factor can bring about one action at one point in time, and yet bring about a very different action at another time. A switch from one to another conformer resulting in altered receptor interaction, signal transduction, half life, associations etc., could be central to one or more pathways of carcinogenesis and phenotypic variation in the development, immune surveillance, presentation and progression of cancer, or in response to its treatment.

Osteoporosis: The hormones involved in the regulation of bone density, including leptin discussed earlier, and others such as parathyroid hormone, osteoprotegenin, and their receptors, all have signal sequences, some cleaved, some uncleaved, rendering them amenable to analysis by the subject invention. The physiology of bone density is complex, poorly understood and subject to a variety of confounding paradoxes—the same agent that promotes bone density in some circumstances can result in bone loss under others. Conformational heterogeneity in response to signaling changes is a potential basis for these observations, with broad potential for diagnostics and therapeutics.

Neurodegeneration: Including prion and alzheimer's diseases, spinal cord injury, and stroke, are areas of perhaps the greatest potential for diagnosis and therapy involving conformatics. Prion protein, the gene product responsible for prion diseases was the first protein for which conformational regulation was demonstrated. In this case, conformational regulation is manifest as topological regulation—the three detectable conformers differ in transmembrane topology, making them relatively easy to identify and distinguish. Amyloid Precursor Protein, the gene product whose aberrant metabolite has been implicated in Alzheimer's disease, is an integral membrane protein which has features in common with the prion protein, including a cleavable signal sequence. Netrins, semiphorins and other genes implicated in axonal guidance (and therefore central to recovery from spinal cord injury), have paradoxical activities consistent with the hypothesis of multiple conformers.

Coronary artery disease: Apolipoprotein B is a complex, multifunctional secretory protein involved in low density lipoprotein metabolism and a prime candidate for conformational heterogeneity. Essentially every integral membrane channel and receptor protein in the body have uncleaved signal sequences amenable to fractionation as described elsewhere.

Chronic obstructive pulmonary disease: The Cystic Fibrosis Transmembrane Regulator (CFTR) is a multispanning integral membrane protein discussed previously, whose biogenesis suggests a more complex fate that is generally accepted. One reason for the difficulty in acceptance of the hypothesis that degraded chains of CFTR represent alternate conformations not needed at that point by the cell, rather than true misfolded chains, is that our evidence in favor of conformatics remains largely unpublished. While those alternative functions remain unknown at the present time, it has been speculated that, the known function of CFTR as a chloride channel affects the salt environment needed for antimicrobial peptides such as the defensins, needed for innate immunity against pathogenic microbes. Thus, conformational dysregulation in which chloride channel function is lost may confer increased susceptibility to infection in the lung and other tissues, as is observed in a wide range of pulmonary and other disorders. By using fractionated cell-free translation and translocation systems, as described in this invention, in combination with available scoring systems including monoclonal antibodies, chemical modification fingerprints, crosslinking and association analysis including sucrose gradient studies, we can catalogue the alternative conformations of CFTR, MDR genes, and other relevant transporters and determine whether these alternatives are utilized to a greater or lesser extent in particular subsets of patients with infectious and other disorders.

Psychiatric disorders: As with neurodegeneration, functional disorders of the brain are likely to involve disturbances in signaling and/or signal transduction. Since receptors on the cell surface, including the family of G protein-coupled receptors, are generally responsible for cell to cell signaling and generally have signal sequences, cleaved or otherwise, these classes of proteins are highly likely to be candidates for conformational regulation.

Taken together, the examples cited above demonstrate the broad nature of this invention and its applicability to a wide range of disorders in which a signal sequence containing protein or receptor is involved.

Relevant manuscripts accompany this application, were submitted as part of priority applications Ser. Nos. 60/171,012 and 60/172,350, and are included by incorporation by reference, as if they were specifically set forth herein. These manuscripts are identified by their title and first author: Rutkowski, et al., "A New Role for the Signal Sequence in Translocational Regulation"; Hegde, et al., "Transmissible and Genetic Prion Diseases Share a Common Pathway of Neurodegeneration" (published in *Nature* (1999) 402:822–826); and Lingappa, et al., "Conformational Control Through Translocational Regulation: A New View of Secretory and Membrane Protein Folding."

The following examples are offered by way of illustration and not by way of limitation.

EXAMPLES

Materials

Rabbit reticulocyte lysate (RRL) and dog pancreatic rough microsomes were prepared and used as described (Hegde and Lingappa, *Cell* (1996) 85:217–228, and references therein). Mouse brain microsomes were prepared in the same manner as canine microsomes. PK was also prepared as described (Hegde et al, *Cell* (1998) 92:621–631. Anti-prolactin antibody was purchased from USB (Cleveland, Ohio) and 3F4 monoclonal anti-PrP antibody was a gift from the Prusiner laboratory. Anti-PDI was purchased from StressGen (Victoria, BC). Disuccinimidyl suberate (DSS) was from Pierce (Rockford, Ill.). Saponin was from Calbiochem (La Jolla, Calif.) and was dissolved as a 20% w/v stock in water, adjusted to 10 mM Hepes, pH 7.2, and the contaminants removed by passage over a 1.5 ml column (per 10 mls saponin) of SP-sepharose fast flow (Amersham Pharmacia; Piscataway, N.J.) and a 2 ml column of Q-sepharose fast flow. A clone encoding yeast prepro-alpha factor was provided by Tom Rapoport.

Fractionation of Reticulocyte Lysate.

The process described herein is for the preparation of a modified in vitro translation system derived from the presently available rabbit reticulocyte lysate (RRL) translation system. The RRL translation system, originally developed by Jackson and Hunt (*Methods Enzymol* (1983) 96:50–74), offers a mammalian based extract competent for translation of messanger RNA (either synthetic or native). Furthermore, when supplemented with microsomal membranes, the biogenesis of secretory and membrane proteins can be reconstituted. By fractionating the RRL into defined components, we have extended the flexibility and potential uses of the in vitro translation system. These advances have several advantages for addressing a variety of biological phenomena (see below). Briefly, RRL is separated into native ribosomes, and a soluble protein fraction (S-100). The S-100 is further fractionated by anion exchange chromatography on DEAE sepharose. The flow-thru (containing all of the globin) is discarded, and the column step-eluted with 300 mM KCl. The eluate (which contains the relevant translation factors) is concentrated by ammonium sulfate precipitation followed by dialysis. This DEAE fraction, along with the ribosomes can reconstitute translation with essentially equal efficiency as the starting RRL. The following is the detailed protocol for preparation of the fractions from 1 ml of RRL. It can easily be scaled up as necessary. Column buffer is 20 mM Tris-Acetate, pH 7.5, 20 mM KCl, 0.1 mM EDTA, 1 mM DTT (added fresh), 10% v/v Glycerol. Elution Buffer is same as Column Buffer, but with 300 mM KCl. Dialysis Buffer is 20 mM Hepes-KOH, pH 7.5, 100 mM KOAc, 0.5 mM MgOAc, 0.1 mM EDTA, 1 mM DTT (added fresh), 10% v/v Glycerol. Fractionation protocol: i) RRL is prepared according to previously published protocols (Jackson and Hunt, supra), except that it is not desalted. Briefly, blood cells from an anaemic rabbit are washed several times, and the cytosol released by hypotonic lysis. The unlysed cells and ghosts (cells which have lysed and released their cytosol) are removed by centrifugation. The supernatant is the RRL used in this fractionation. ii) RRL is adjusted to 1 mM $CaCl_2$, digested with 150 U/ml micrococcol nuclease for 10 minutes at 25° C., and the reaction terminated by the addition of EGTA to 2 mM. The RRL is chilled to 0° C. on ice, and all subsequent procedures done at 4° (in the cold room) or on ice. iii) The nucleased RRL is centrifuged for 20 minutes at 100,000 RPM in thick-walled polycarbonate tubes (1 ml capacity) in a TL-100.2 rotor at 4° C. The supernatant (S-100) is removed to a pre-chilled 2 ml eppendorf tube on ice. The pellet is rinsed once in Dialysis Buffer, and resuspended in 100 μl of dialysis buffer. The ribosomes are then frozen in aliquots and stored at –80° C. They are stable for at least one year without any loss of activity. Avoid excessive freeze-thaws, although it appears stable to at least 2–3 uses without any problems. iv) The S-100 is diluted with an equal volume (1 ml) of column buffer and applied to a 3 ml DEAE sepharose column. The column is washed with additional column buffer until the last traces of the bright red globin have flowed through. The column is then step eluted with 10 mls of Elution Buffer, and eluate collected. To the 10 mls of eluate, 5.6 grams of solid ammonium sulfate is added slowly with constant stirring (bringing it to ~80% saturation). Stir at 4° C. (or on ice) for an additional 20–30 minutes after the last of the ammonium sulfate is added. Sediment the precipitate by centrifugation (10,000×g for 15 minutes), remove and discard the supernatant, and dissolve the pellet in at most 1 ml of dialysis buffer, preferably 0.5 ml (it goes into solution readily with only gentle mixing). Dialyze against 500 ml dialysis buffer to remove the residual ammonium sulfate (with one change of buffer if desired) at 4° C. for 8–12 hrs. The sample is recovered from the dialysis tubing, frozen in aliquots, and stored at –80° C. It is stable for over 1 year with no noticeable loss of activity. Avoid excessive freeze-thaws, although it appears stable to at least 2–3 uses without any problems.

EXAMPLE 1

Prion Protein

A dramatic example of a substrate with complex and highly regulated translocation is the prion protein (PrP), a 35 kD brain glycoprotein involved in the pathogenesis of several neurodegenerative disorders (Prusiner (1997) Science 278, 241–251). PrP is simultaneously synthesized in three alternate topological forms at the ER (Hegde et al., (1998) Science 279, 827–834). One of these forms, termed $^{sec}$PrP, is fully translocated across the ER membrane, and is the predominant form observed in vivo. By contrast, the other two forms of PrP are made as singly-spanning membrane proteins in opposite orientations with either the N- or C-terminus in the ER lumen (termed $^{Ntm}$PrP and $^{Ctm}$PrP, respectively). PrP biogenesis appears to involve multiple steps leading to at least three distinct and assayable endpoints, it therefore was used as a sensitive probe for any potential substrate-specific effects of N-terminal signal sequences. In the following experiments, the native signal sequence of PrP was replaced with the well-studied signal sequences of the secretory proteins preprolactin and pre-beta-lactamase (FIG. 1A). The chimeric proteins (Prl-PrP and βL-PrP, respectively) were compared to native PrP for their ability to be targeted, translocated, and synthesized in each of the topological forms characteristic of PrP (FIG. 1B).

Plasmid Constructions

Standard techniques were used in the creation of all plasmid constructs (Sambrook et al 1989). All constructs were made in the pSP64 vector (Promega, Madison, Wiss.) containing the 5' UTR of Xenopus globin inserted at the HindIII site. Prl-PrP was constructed by PCR amplification of the region encoding amino acids 1–30 of preprolactin and amino acids 23–28 of PrP. The PCR product was ligated into a Bgl2-PflmI digested vector containing wild-type PrP (PrP SV12), so that the resulting clone contained a precise fusion of the preprolactiin signal sequence to the mature region of PrP. All other PrP, AV3, and G123P signal sequence replacements were constructed similarly, except that for Prl-PrP$_{(AV3)}$, the site of fusion was engineered three amino acids downstream of the βL signal cleavage site. This clone was identical in final topology to Prl-PrP$_{(AV3)}$ constructed as a perfect fusion. The μL signal sequence was found to contain an Asp at position 2 rather than Ser. This replacement had no significant effect on βL-PrP topology. PrP$_{(R2,3)}$(SEQ ID NO: 2); PrP$_{(R4,5)}$(SEQ ID NO: 4); PrP$_{(D2,3)}$(SEO ID NO: 3); and PrP$_{(D4,5)}$(SEQ ID NO: 5) were created by first introducing a silent NheI site at codon 8 of PrP SV12, and then ligating annealed oligos encoding these mutations as Bg12-NheI fragments. To fuse these signals sequences to the prolactin mature region, the latter (beginning at amino acid 34) was PCR-amplified and digested with NcoI. This fragment was ligated into the wild-type preprolactin vector (pSP BPI) digested at NcoI, effectively deleting the first 33 amino acids of prolactin. An XbaI site, encoding Thr-Arg, was engineered immediately upstream of amino acid 34, and PrP, preprolactin, pre-beta-lactamase, and prepro-aLpha factor signal sequences were amplified and inserted as HindIII-SpeI fragments. Prl-βL was constructed using an identical scheme. All clones were verified by dideoxy sequencing.

Cell-Free Translation and Proteolysis

In vitro transcription with SP6 RNA polymerase, translation with RRL, and translocation into canine rough microsomes have been described (Hegde et al, (1998) Cell 92, 621–631 and references therein). Translations were carried out at 32° (or 26° in FIG. 4C) for 20–45 minutes. Where indicated membranes were isolated by sedimentation and resuspended in physiological salt buffer (PBS) as described (Hegde and Lingappa, (1996) Cell 85, 217–228). Proteolysis with 0.5 mg/ml PK was for 45–90 minutes at 0°. Reactions were terminated with 12.5 mM PMSF and transferred into 10 volumes of 1% SDS at 100°.

Targeting Studies

Figure 2:
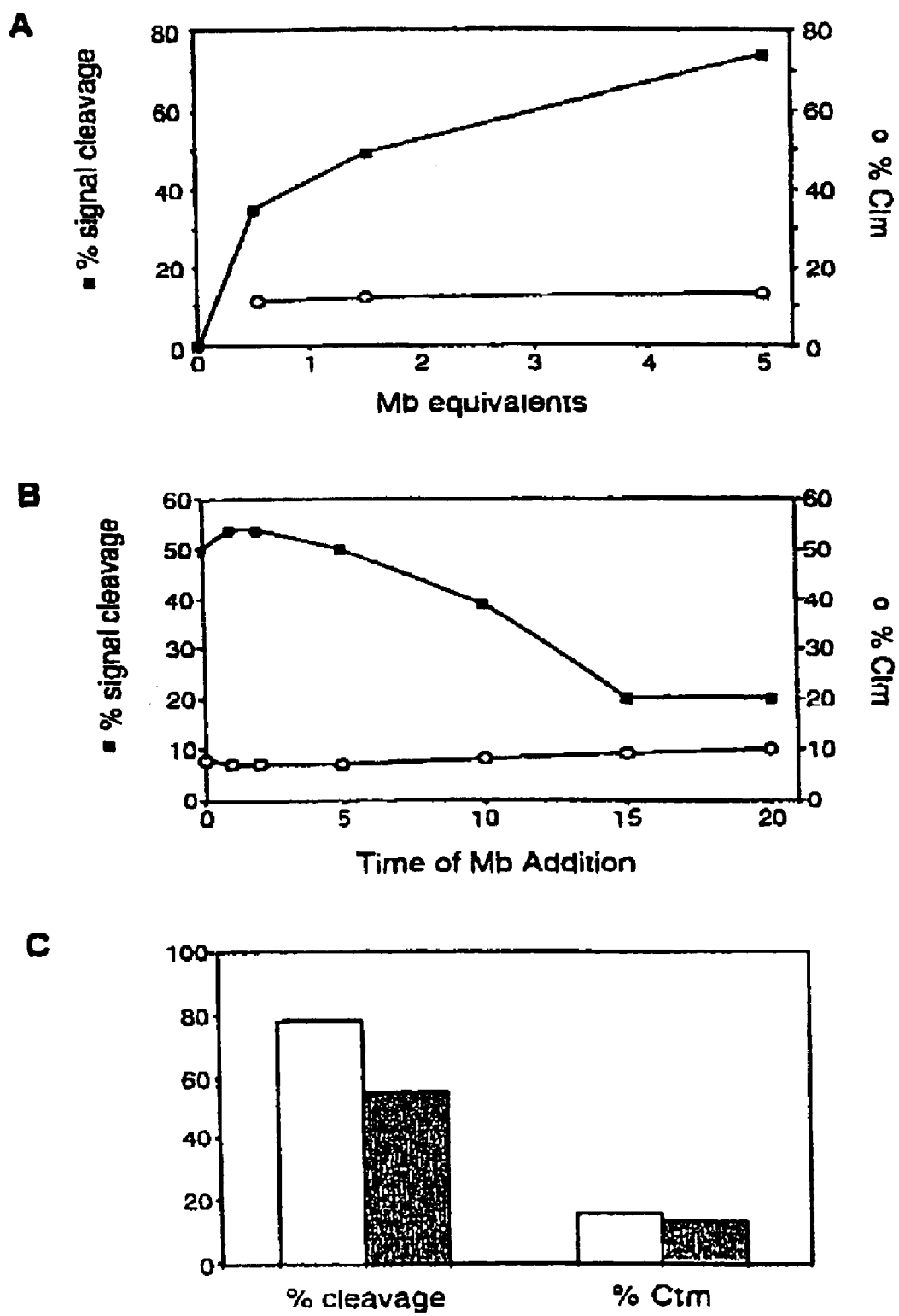

In FIG. 2B, translation in the absence of membranes was initiated at 32°, following a 30 second pre-incubation in the absence of transcript. Five minutes after transfer to 32°, aurintricarboxylic acid (ATA—Sigma) was added to 75 μM. Aliquots were removed to ice at staggered intervals. Upon collection of the last sample, membranes were added to all but one aliquot. The samples were then returned to 32° for 30 minutes, followed by proteolysis and immunoprecipitation with 3F4. In FIG. 2C, PrP truncated at StuI was translated at 32° in the presence or absence of microsomes. Five minutes into this incubation, ATA was added as above. After 30 minutes of translation, samples were removed to ice, membranes were added to the samples lacking them, and incubation at 32° was continued for 30 minutes. After translation was completed, chains were released with 10 mM EDTA at 26° for 10 minutes. Proteolysis and immunoprecipitation followed.

Cross-Linking

For samples to be cross-linked, translation products were sedimented and resuspended as above, and divided into equal aliquots. One aliquot was set aside, and to the other DSS was added to 1 mM and the sample was incubated at room temperature for 30 minutes. Reactions were terminated by the addition of 50 mM Tris (pH 8.0), 10 mM EDTA, and 10 μg/ml RNase A (Sigma, St. Louis, Mo.). Where the isolation of lumenal cross-links was desired, 0.5% saponin was included as well, followed by sedimentation for 10 minutes at 75,000 rpm, 4°, in a TLA100. For immunoprecipitation of cross-linked material, saponin was added as above, and antibody was added directly to the quenched cross-linking reaction.

Microsomal Membrane Fractionation.

Briefly, rough microsomal membranes (RMs) are prepared as previously described (Walter and Blobel Methods Enzymol (1983) 96:84–93). Following the extraction of lumenal and peripheral membrane proteins, a subset of the integral membrane proteins are solubilized using detergent and fractionated by a combination of lectin affinity and ion-exchange chromatography. Individual fractions are reconstituted by removal of detergent in the presence of lipids, and the proteoliposomes that form are collected and used to assay for substrate-specific activities. The following is the detailed protocol for the preparation and characterization of an initial set of fractions that demonstrate the principles involved. This initial procedure may be modified in several ways as detailed in section [d] below.

Fractionation protocol: i) RMs are prepared according to previously published protocols (Walter and Blobel (1983) supra), Briefly, pancreatic tissue from a recently deceased dog (or pig) is homogenized, and after a centrifugation step to remove debris, nuclei and large subcellular structures, the remaining material is subject to high-speed centrifugation. Sedimented material is resuspended and stored frozen at −80° C. All subsequent procedures are carried out either on ice or in a cold room at 4° C., unless otherwise noted. ii) The RMs (in 50 mM triethanolamine-acetate, pH 7.4, 250 mM sucrose, 1 mM DTT) are diluted to a final concentration of 0.5 equivalents per μl with a buffer containing 50 mM Hepes, pH 7.4, 250 mM sucrose. Saponin is added to a final concentration of 0.5% from a 20% stock solution. After the solution is mixed gently, but thoroughly, the microsomes are isolated by centrifugation at 100,000 rpm for 10 minutes in a TL100.3 rotor (Beckman instruments). The pellet is resuspended at a concentration of 0.5 equivalents per μl in buffer containing 500 mM K-acetate, 50 mM Hepes, 10 mM EDTA, 125 mM sucrose. The microsomes are again isolated by centrifugation (100,000 rpm for 20 min in TL100.3 rotor) and resuspended at 1 equivalent per μl in extraction buffer [350 mM K-acetate, 50 mM Hepes, pH 7.4, 5 mM MgCl$_2$, 15% w/v glycerol, 5 mM 2-mercaptoethanol, EDTA-free protease inhibitors (Roche Molecular Biochemicals) and 0.8% deoxy-BigCHAP (Calbiochem)]. Following extraction for 10 minutes on ice, insoluble material is sedimented at 100,000 rpm for 30 minutes in the TL100.3 rotor. The supernatant is termed the DBC extract, and used in subsequent steps. iii) The DBC extract is incubated with one-fifth to one-seventh volume of immobilized Con A (Pharmacia) with constant and gentle mixing for between 10 and 15 hours, at 4° C. The supernatant (Con A-depleted DBC extract) is removed to a separate tube and either saved on ice (for up to 12 hrs) or for extended storage, frozen in liquid nitrogen and kept at −80° C. The Con A beads are washed three times in five to seven volumes of wash buffer [500 mM K-acetate, 50 mM Hepes, pH 7.4, 5 mM MgCl2, 15% w/v glycerol, and 0.5% deoxy-BigCHAP], and the bound proteins eluted with 5 volumes of elution buffer [500 mM K-acetate, 50 mM Hepes, pH 7.4, 20 mM EDTA, 15% w/v glycerol, 250 mM methyl-alpha-D-mannopyrannoside, 2 mM 2-mercaptoethanol and 0.5% deoxy-BigCHAP] by incubation for 2 hours at 25° C. with constant mixing. The eluted material (Con A elutate) is chilled on ice for subsequent manipulations. iv) The Con A eluate is diluted with 1.5 volumes of dilution buffer [50 mM Hepes, pH 7.4, 15% w/v glycerol] and divided for incubation with ion-exchange resins. The diluted Con A eluate is added to one-twentieth volume of either Q-sepharose-Fast Flow or S-sepharose-Fast Flow (both from Pharmacia), and incubated for 1 hour with constant mixing. The unbound fraction of the Q-sepharose-Fast Flow and S-sepharose-Fast Flow incubations are added to one-twentieth volume of either S-sepharose-Fast Flow or Q-sepharose-Fast Flow, respectively, and incubated for one hour at 4° C. with constant mixing. The unbound material of this incubation is set aside (Q/S-flow thru and S/Q-flow thru). The resin from the second incubation (with S-sepharose and Q-sepharose) are washed in 10 volumes of buffer containing [200 mM K-acetate, 50 mM Hepes, pH 7.4, 15% w/v glycerol, 0.5% deoxy-BigCHAP], and subsequently eluted in 4 volumes of the same buffer containing 1000 mM K-acetate. These fractions are termed the Q-FT and S-FT, respectively. The resin from the first ion-exchange incubations (with Q-sepharose and S-sepharose) are washed in 10 volumes of buffer containing [200 mM K-acetate, 50 mM Hepes, pH 7.4, 15% w/v glycerol, 0.5% deoxy-BigCHAP], and subsequently eluted in four volumes of the same buffer containing 500 mM K-acetate. The resin is eluted a second time in four volumes of the same buffer containing 1000 mM K-acetate. These fractions are termed Q-500, S-500, Q-1000, and S-1000, respectively. v) The fractions are reconstituted as follows. First, lipids are prepared by mixing 8 mg phosphatidyl choline (PC, from a 10 mg/ml stock solution), 2 mg phosphatidyl ethanolamine (PE from a 10 mg/ml stock solution), 10 mg deoxy-BigCHAP (DBC, from a 100 mg/ml stock solution), and DTT added to 10 mM from a 1M stock. The sample is dried under vacuum (ne heat) and resuspended in 500 μl of buffer [50 mM Hepes, pH 7.4, 15% glycerol]. DBC is added from a 100 mg/ml stock solution to bring the final concentraion to approx. 20 mg/ml (~2% w/v). The lipid mixture is frozen in liquid nitrogen and stored at −80° C. until needed. For reconstitutions, 100 μl of the DBC extract or ConA depleted DBC extract is mixed with 100 μl of either Con A elution buffer, Con A eluate, S-FT, Q-FT, S-500, Q-500, S-1000, or Q-1000 fractions prepared as described above. In addition, 5 μl of the lipid mixture is added and the sample mixed thoroughly before adding the individual samples to 160 mg of BioBeads SM2 (Biorad). The mixtures are incubated for 12–18 hours at 4° C. with constant mixing. vi) To recover the proteoliposomes, the liquid phases from step (v) are separated from the biobeads and transferred to fresh tubes. These samples are diluted with five volumes of ice-cold distilled water, mixed, and transferred to 1.3 ml centrifuge tubes on ice. The samples are centrifuged for 20 min in TL100.3 rotor (with adaptors for the 1.3 ml tubes) at 70,000 rpm. The supernatant is discarded and the pelleted proteoliposomes are resuspended in 30 μl of a buffer containing 100 mM K-Acetate, 50 mM Hepes, pH 7.4, 250 mM sucrose. These are frozen in liquid nitrogen and stored at −80 until used in assays for translocation. vii) Translocation assays are performed as described previously (ref.) using 1 μl of the proteoliposomes from step (vi) per 10 μl of translation reaction.

Figure 4:
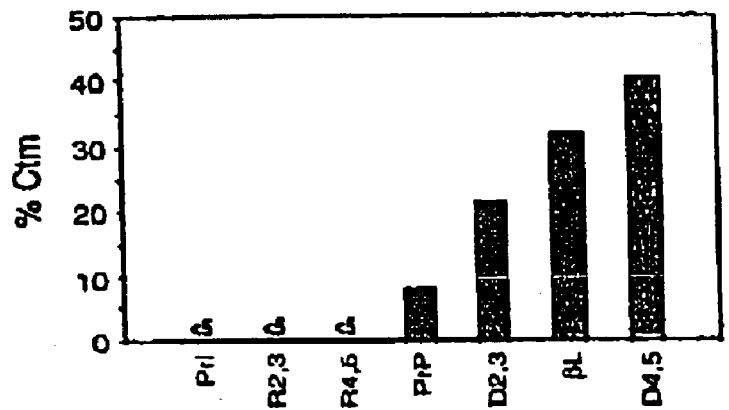
Figure 4:
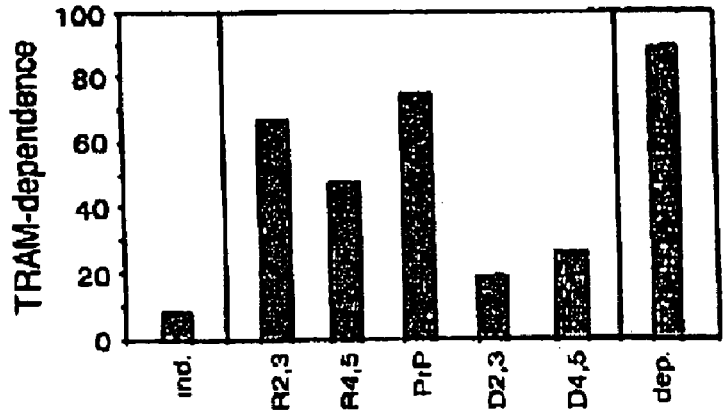

Purification of PDIp 20,000 equivalents (see Walter and Blobel, 1983, for definition) of canine pancreatic rough microsomal membranes were adjusted to 80 mls in 50 mM triethanolamine, 250 mM sucrose, 0.2 mM PMSF, 5 μg/ml aprotinin, 10 μg/ml chymostatin, 1 μg/ml E64, 5 μg/ml antipain, 1 mM DTT. With constant mixing, purified saponin was added slowly to 1% w/v final concentration, and after incubation at 4° C. for 15 minutes, membranes were sedimented by centrifugation for 2 h at 70,000 rpm in 70.1 Ti rotor (Beckman). The supernatants were pooled and applied to a 5 ml column of ConA sepharose at a flow rate of 6.2 mls/hr. The column was washed at 15 ml/hr with 25 mls of the above buffer containing 100 mM KAc, and an additional 25 mls with the above buffer without KAc. The column was eluted at 3 ml/hr at room temperature with 20 mls of the above buffer containing 1 M α-methyl-mannopyrannoside. The eluate was collected on ice and applied at 4° C. to a 1 ml Q-sepharose fast flow column. The column was washed with 4 ml of 50 mM Hepes, pH 7.5, 2 mM MgAc, 1 mM CaCl2, 1 mM DTT and eluted with 2 mls of this same buffer containing 1 M KAc. The eluate was further fractionated on a Superdex PG 16/16 column (Pharmacia) and 80 1.5 ml fractions collected. 15 μl each of fractions 31–56 were analyzed by SDS-PAGE and coomassie staining (FIG. 4$b$). Peak fractions containing gp65 were pooled and aliquots used for subsequent sequence analysis (by ProSeq, Salem, Mass.).

Preparation of TRAM-Reconstituted Membranes

Glycoprotein-depleted membranes were prepared as described (Hegde et al, 1998c). Purified TRAM, prepared as described (Gorlich and Rapoport, 1993), was added at 4× the level present in starting membranes (as judged by immunoblotting) to the glycoprotein-depleted extract.

Miscellaneous

SDS-PAGE was performed using either 15% gels or 12.5% or 15% Tris/Tricine gels. Bands were either visualized directly by autoradiography, or with the aid of a TranScreen LE intensifying screen (Kodak; Rochester, N.Y.). Quantitation was performed by scanning on an AGFA ArcusII flatbed scanner and densitometry using Adobe Photoshop software. Immunoprecipitations were as described (Chuck and Lingappa, 1992)

While all three proteins were efficiently targeted and translocated across the ER, they differed dramatically in their topological outcomes. Consistent with previous findings, PrP was synthesized predominantly in the $^{sec}$PrP and $^{Ntm}$PrP topological forms, with a small yet significant amount of $^{Ctm}$PrP (~7%; FIG. 1C). By contrast, Prl-PrP was synthesized predominantly in the $^{sec}$PrP form, followed by lesser amounts of $^{Ntm}$PrP, and essentially undetectable amounts of $^{Ctm}$PrP (<2%). Conversely, the topology of βL-PrP was dramatically shifted toward $^{Ctm}$Prp (~34%) largely at the expense of $^{sec}$PrP. These results suggest that different signal sequences encode information which dramatically affects subsequent topological events. This information appears to be in addition to and dependent on the basic targeting feature common to all three signal sequences. Thus, a chimeric protein consisting of the N-terminal twenty amino acids of the cytosolic protein globin fused to mature PrP fails to translocate in any of the topological forms (data not shown). Taken together, the experiments in FIG. 1 demonstrate that the signal sequence of PrP plays a role in topological regulation.

In principle, the influence of the signal sequence on topology described above could be ascribed to the well established role of signal sequences in targeting. If the different signal sequences were to target to the ER at different rates, then the N-terminus of the mature substrate would-be synthesized to varying lengths by the time the ribosome-nascent chain complex interacts with the translocon. One consequence of increasing amounts of synthesis during the targeting step may be to favor synthesis of one of the topological forms of PrP (most likely $^{Ctm}$Prp, the N-terminal domain of which is not translocated). This hypothesis implies that manipulation of the kinetics of PrP targeting should recapitulate the shifts in topology seen by replacements of the signal sequence. This possibility was tested in three ways.

First, the amount of ER-derived canine pancreatic microsomes present in the translation reactions was titrated and the effect on PrP topology was examined. As the total concentration of the translocation machinery decreases, the time between initiation of synthesis and interaction with the translocon should increase, allowing increasing amounts of the nascent chain to be synthesized prior to targeting. We found that varying the concentration of microsomes over a 10-fold range did not impact the relative ratios of the different topological forms of PrP (FIG. 2A). The decrease in translocation efficiency with decreasing microsome concentration, reflected by a decrease in efficiency of signal cleavage, is likely due to the loss of "translocational competence," the relatively brief period in nascent chain growth when the ribosome-nascent chain complex is able to interact productively with the translocation machinery (Perara et al. *Science* (1986) 232:348–352). A similar loss of translocation efficiency was observed with other substrates (data not shown).

In a second approach, translation reactions were synchronized by inhibiting initiation after 5 min, and microsomes were added at successively later times. We found that regardless of the duration for which translation was allowed to occur prior to the addition of microsomes, the percentage of ${}^{Ctm}$PrP synthesized remained constant (FIG. 2B). Again the efficiency of signal cleavage decreased at the later time points due to an increasing percentage of nascent chains that had presumably lost translocational competence.

Finally, the targeting step itself was synchronized. In these experiments, PrP mRNA was truncated at a defined length and translated in the absence of microsomal membranes. The resulting ribosome-associated nascent chains remain competent for translocation in the absence of further translation, and can be targeted synchronously by subsequent addition of microsomes (Perara et al., 1986, supra). Following targeting, the ribosomes were disassembled, and the topology achieved by the truncated PrP chain, which lacks only a small portion of the PrP C-terminus, was compared to the same truncated product that was targeted co-translationally. We found that synchronizing the targeting of this 223-mer of PrP did not affect the relative ratios of the topological forms observed (FIG. 2C). Similar results were obtained for a 180-mer as well (data not shown). Taken together, these experiments collectively argue that the manipulation of the kinetics of the targeting step of PrP is insufficient to alter the final topology that is achieved. We infer from these findings that the topology-specific information encoded within a signal sequence is likely to act at a step beyond targeting.

Since differences in the kinetics of targeting cannot account for the influence of the signal sequence on PrP topology, we turned to the other site of signal sequence action, the ER membrane. Signal sequence recognition events at the ER membrane appear to occur early during translocation and precede the establishment of a tight ribosome-membrane junction. If the preprolactin and prebata-lactamse signal sequences encode innate differences in the mechanism of their recognition by the translocation machinery, these differences might be manifested in the state of the junction.

Short translocation intermediates of preprolactin and pre-beta-lactamase were analyzed for their accessibility to proteinase K (PK), a probe for the state of the ribosome-membrane junction. Consistent with previous reports (Connolly et al., *J. Cell Biol* (1989) 108:299-307; Jungnickel and Rapoport, *Cell* (1995) 82:261–270), the tight seal of the junction shielded the preprolactin 86-mer from proteolytic attack. By contrast, the pre-beta-lactamase 84-mer was largely susceptible to digestion, indicative of an open ribosome-membrane junction (FIG. 3A). To determine if this difference was attributable to signal sequence function, we exchanged the signal sequences of preprolactin and pre-beta-lactamase (constructs βL-Prl and Prl-βL). We found that the βL-Prl 81-mer was accessible to protease digestion while the Prl-βL 93-mer was not (FIG. 3A). Similar results were obtained with translocation intermediates approximately 20 amino acids longer (data not shown). These data argue that signal sequences can differentially influence the state of the ribosome-membrane junction during the early biogenesis of secretory proteins.

Given the above results, modulation of the ribosome-membrane junction by the signal sequence seemed to be a plausible mechanism for the regulation of PrP topology. If so, the topological form of PrP with its N-terminus in the cytosol (${}^{Ctm}$PrP) may be expected to arise from chains that did not establish a tight ribosome-membrane junction early in translocation. To test this hypothesis, increasingly longer translocation intermediates of PrP, Prl-PrP, and βL-PrP were assembled at the ER and separated from non-targeted chains by sedimentation, and the state of the ribosome-membrane junction was analyzed by PK digestion (FIG. 3B).

When truncated at a point corresponding to a 61-mer of wild-type PrP, all three substrates are fully accessible to protease, and thus have failed to establish a tight junction. However, the three constructs show differential protease accessibility at a translocation intermediate only 52 amino acids longer, even before the synthesis of the transmembrane domain. Prl-PrP, which makes very little ${}^{Ctm}$PrP, is largely shielded from digestion at this point, while a greater percentage of βL-PrP chains are accessible to the protease. At this truncation point, all three constructs are resistant to extraction from the membrane with high salt (0.5 M potassium acetate; data not shown), suggesting that the ribosome is stably associated with the translocation channel.

Furthermore, βL-PrP nascent chains remain more accessible to PK than Prl-PrP chains throughout their biogenesis. Most of the unprotected chains retain their signal sequences, likely as a consequence of the open junction. The observed diminishment of protease protection in all three substrates with increasing chain length probably reflects junctional opening during the synthesis of $^{Ntm}$PrP. Collectively, these results argue that signal sequence-mediated regulation of the ribosome-membrane junction can have dramatic consequences for subsequent translocational events.

The putative role of the ribosome-membrane junction in governing final topology suggests that trans-acting factors which regulate the junction could influence PrP biogenesis. The TRAM glycoprotein is thought to interact with signal sequences to facilitate the initial association between the ribosome-nascent chain complex and the translocon (Voigt et al., *J. Cell Biol* (1996) 134:25–35). The signal sequences of some substrates (such as preprolactin) do not depend on TRAM for translocation, though most (including pre-beta-lactamase) are TRAM-dependent (Gorlich et al., *Nature* (1992) 357:47–52; Gorlich and Rapoport, *Cell* (1993) 75:615–630; Voigt et al., 1996, supra). Although TRAM has additionally been implicated in regulating the ribosome-membrane junction during the translocation of other substrates (Hegde et al., *Cell* (1998) 92:621–631), functional studies have thus far failed to demonstrate a direct or critical role for TRAM in PrP topology (Hegde et al., *Mol. Cell* (1998) 2:85–91). Thus, we reasoned that it should be possible to dissociate the TRAM-dependence feature of a signal sequence from its role in PrP topology.

We sought to identify mutations within the PrP signal sequence that differentially modify topology but not dependence on TRAM. By analogy to the effects of charge on the topology of signal-anchor proteins (e.g., Sipos and von Heijne, *Eur J. Biochem* (1993) 213:1333–1340; Spiess, *FEBS Lett* (1995) 369:76–79), we reasoned that non-conservative mutations in the PrP signal sequence may affect PrP biogenesis. Leaving the hydrophobic core of the signal sequence intact to allow efficient targeting, we replaced either codons 2 and 3 or codons 4 ard 5 with arginine or aspartic acid codons [PrP$_{(R2,3)}$(SEQ ID NO: 2), PrP$_{(D2,3)}$ (SEQ ID NO: 3), PrP$_{(R4,5)}$(SEQ ID NO: 4) and PrP$_{(D4,5)}$ (SEQ ID NO: 5), respectively; see FIG. 4A). Topological analysis of PrP$_{(R2,3)}$(SEQ ID NO: 2) and PrP$_{(R4,5)}$(SEQ ID NO: 4) revealed a decrease in $^{Ctm}$PrP synthesis while PrP$_{(D2,3)}$(SEQ ID NO: 3) and PrP$_{(D4,5)}$(SEQ ID NO: 5) both showed increased $^{Ctm}$PrP synthesis (FIG. 4B).

To assess the TRAM dependence of these mutant signal sequences we fuised each of them to preprolactin in place of the native preprolactin signal sequence. The ability of these constructs to translocate into glycoprotein-depleted proteoliposomes either containing or lacking purified TRAM was measured. TRAM-dependence was defined as the percentage of chains that require TRAM to translocate. We found that all four mutated signal sequences were less TRAM-dependent than the wild-type PrP signal sequence, despite their divergent effects on PrP topology (FIG. 4C). Thus, the TRAM-dependence of the PrP signal sequence can be dissociated from the role of the signal sequence in regulating topology, arguing for a previously unappreciated mechanism by which signal sequences influence topology.

Mutations in the membrane-spanning domain can influence the topology of PrP (Hegde et al., *Science* (1998) 279:827–834). Because transmembrane (TM) domains, like signal sequences, can elicit changes in the ribosome-membrane junction (Liao et al., *Cell* (1997) 90:31–41), it is plausible that the mechanisms by which these two domains regulate topology are related. Just as certain signal sequences open the ribosome-membrane junction, the TM domain of PrP may be capable of eliciting an opening of the junction. In this scenario, TM domain mutants that favor $^{Ctm}$PrP would elicit a greater opening of the junction than wild-type PrP, while mutants-that favor $^{sec}$PrP would act to maintain a closed junction. We tested this hypothesis by analyzing PrP constructs that contained various combinations of changes in both the signal sequence and TM domains.

Figure 5:
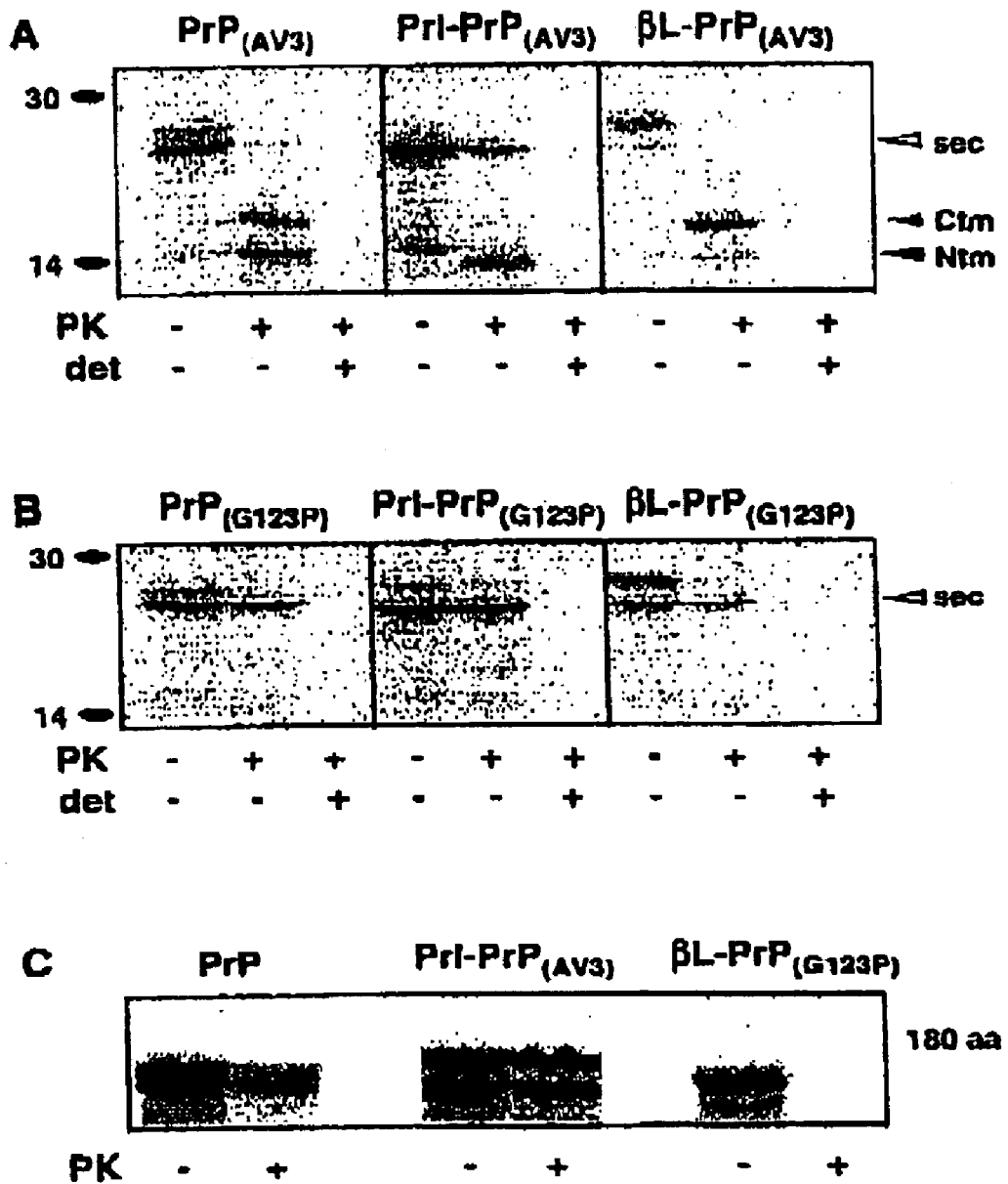

Replacement of conserved alanines in the TM domain with valines markedly increases the proportion of PrP made in the $^{Ctm}$PrP topology (Hegde et al., *Science* (1998) 279:827–834). One of these mutants [PrP$_{(Av3)}$] which generates approximately 40% of the molecules in the $^{Ctm}$PrP form] was engineered with either a preprolactin or pre-beta-lactamase signal sequence [Prl-PrP$_{(Av3)}$ and βL-PrP$_{(Av3)}$]. If the AV3 mutation causes the ribosome-membrane junction to open independently of the signal sequence, then the Prl-PrP$_{(AV3)}$ construct should synthesize roughly as much $^{Ctm}$PrP as PrP$_{(Av3)}$. Strikingly, we observed that Prl-PrP$_{(Av3)}$ reduces $^{Ctm}$PrP synthesis to barely detectable levels (FIG. 5A, middle panel). Conversely, βL-PrP$_{(Av3)}$ makes almost exclusively $^{Ctm}$PrP (FIG. 5A, right panel).

Similarly, according to the hypothesis stated above, a TM mutant which favors $^{sec}$PrP synthesis should cause the ribosome-membrane junction to close. When we replaced the signal sequence of the TM mutant PrP$_{(G123P)}$, which makes only $^{sec}$PrP with the preprolactin or pre-beta-lactamase signal sequence [Prl-PrP$_{(G123P)}$ and βL-PrP $_{(G123P)}$], we found that all three substrates were synthesized only as $^{sec}$PrP However, closure of the ribosome-membrane junction should stimulate overall translocation efficiency, since chains synthesized with a closed junction have the ER lumen as their only option for exit from the ribosome. Instead, we found that βL-PrP$_{(G123P)}$ translocates relatively poorly compared to PrP$_{(G123P)}$ and Prl-PrP$_{(G123P)}$. This result argues that the G123P mutation does not necessitate the production of $^{sec}$PrP by closing the ribosome-membrane junction, but rather by preventing the translocation of chains which would otherwise become $^{Ctm}$PrP.

The findings above suggested that rather than acting independently of the signal sequence, the TM domain is constrained by the preceding action of the signal sequence. To test directly whether the TM domain has any bearing on the state of the ribosome-membrane junction dictated by the signal sequence, we analyzed the state of the junction for Prl-PrP$_{(AV3)}$ and βL-PrP$_{(G123P)}$ at a point after the emergence of the TM domain. We found that the junction remains open for βL-PrP$_{(G123P)}$ and closed for Prl-PrP$_{(Av3)}$, irrespective of the identity of the TM domain (FIG. 5C). These results suggest that the initial action of the signal sequence on the ribosome-membrane junction, even before the synthesis of the TM domain, is critical to subsequent topological determination.

The observation that PrP chains are committed to a transmembrane topology prior to the synthesis of the TM domain was unexpected. Why might it be important to place the key regulatory steps at such an early point in biogenesis? One possible reason is that certain early events in the folding of PrP are not readily reversible at a later point in biogenesis when the TM domain has been synthesized. Thus, it may be important to initiate these early folding events in a temporally and spatially restricted manner (given that the N-terminus can ultimately reside in one of two environmentally different compartments). To examine this possibility, we sought to identify interactions between PrP and the machinery of protein folding that are initiated in a topology specific manner at a time before topology has been formalized.

In initial experiments, we used cross-linking to identify proteins that displayed preferential association with either $PrP_{(G123P)}$ or $PrP_{(AV3)}$. While several proteins interact comparably with both substrates, a 65 kDa protein (p65) cross-links more strongly to $PrP_{(G123P)}$ than to $PrP_{(AV3)}$ (FIG. 6A). We then similarly analyzed Prl-PrP and βL-PrP truncated at the same location and found that p65 preferentially cross-links to Prl-PrP, suggesting that nascent PrP chains in the process of being made in the $^{sec}PrP$ topology specifically associate with this factor (FIG. 6B). To determine when during PrP biogenesis this interaction is initiated, we examined early translocation intermediates of Prl-PrP and βL-PrP for the differential presence of this cross-link. Remarkably, we found that p65 and a slightly smaller protein cross-link preferentially to the Prl-PrP translocation intermediate truncated at codon 113 of wild-type PrP (FIG. 6C). Thus, association of p65 with nascent PrP chains very early in biogenesis correlates with the propensity of the substrate to ultimately be made in the $^{sec}PrP$ topology.

We took advantage of the biochemical properties of the p65 cross-linked adduct to purify and identify this protein. The adduct was extractable by saponin, implying a lumenal localization for p65; it migrated as a 4 S protein by sucrose gradient analysis, suggesting it was monomeric; it was retained on a ConA-sepharose column, indicating that p65 is glycosylated; and it was also retained on a Q-sepharose column, suggestive of a negative net charge imparted by p65 on an otherwise net-positive PrP molecule. When these properties were combined in a stepwise fractionation of canine rough microsomes, a single major 65 kDa protein was purified (FIG. 6D). Sequencing of peptide fragments generated by cyanogen bromide cleavage of this protein identified it as PDIp, a pancreas-specific member of the Protein Disulfide Isomerase (PDI) family of chaperones (Desilva et al., Cell Biol (1996) 15:9–16; Elliott et al., Eur J. Biochem (1998) 252:372–377).

The identity of p65 as PDIp was confirmed by immunoprecipitation with antibodies raised against PDIp (FIG. 6E). In addition, the slightly smaller cross-linking partner was immunoprecipitated by antibodies to ubiquitous PDI, further arguing for a specific interaction between PrP and this family of proteins. The immunoprecipitation studies confirmed that both PDI and PDIp cross-link more strongly to Prl-PrP than to βL-PrP (FIG. 6E). This differential crosslinking of $^{sec}PrP$ favoring constructs to PDI was also observed in microsomes isolated from brain, the tissue in which PrP is predominantly expressed. In this case, only cross-links to the ubiquitous PDI were observed, consistent with previous observations that PDIp is not expressed strongly in brain tissue (Desilva et al., 1996, supra).

We next sought to determine if $^{sec}PrP$ specifically interacts with any other lumenal proteins early during biogenesis. Examination of the saponin extractable cross-link revealed prominent interactions between the $^{sec}PrP$ favoring constructs [$PrP_{(R2,3)}$(SEQ ID NO: 2) and $PrP_{(R4,5)}$(SEQ ID NO: 4)] and proteins of approximately 30 kDa, 60 kDa, and 65 kDa (FIG. 6F). Similar cross-links to the $^{Ctm}PrP$ favoring mutants [$PrP_{(D2,3)}$(SEQ ID NO: 3) and $PrP_{(D4,5)}$(SEQ ID No: 5)] were markedly diminished. As expected, the 60 kDa and 65 kDa cross-links were identified by immunoprecipitation as PDI and PDIp (data not shown). The identity of the 30 kDa cross-linking partner remains unknown. These cross-links are not observed simply as a fortuitous consequence of the lumenal localization of $^{sec}PrP$ because prominent cross-links to lumenal proteins were not observed with early translocation intermediates of preprolactin (FIG. 6F and data not shown). The cross-linking data collectively argue that one consequence of signal. sequence-mediated events in early PrP biogenesis is to facilitate differential interactions between the nascent chain and factors which may subsequently participate in its biogenesis.

EXAMPLE 2

Pathogensis of Altered Topology of Prion Protein is Common to Genetic and Infections Prion Diseases Prion diseases can be infectious, sporadic and genetic (Prusiner, S. B. PNAS. (1998) 95:13363–13383; Weissmann, C J. Biol. Chem (1999) 274:3–6; Johnson New Eng J Med (1998) 339:1994–2004; Horwich Cell (1997) 89:499–510). The infectious forms of these diseases, including bovine spongiform encephalopathy and Creutzfeldt-Jakob disease, are usually characterized by the accumulation in brain of the transmissible pathogen, and abnormally folded insoform of the prion protein (PrP) termed $PrP^{Sc}$. However, certain inherited PrP mutations appear to cause neurodegeneration in the absence of $PrP^{Sc}$ (Brown, Ann Neur (1994) 35:513–529; Tateishi, J. et al., Neurology, 1990, 40:1578–1581; Tateishi, Neurology, (1996) 46:532–537, Tateishi, J., Brain Pathology, (1995) 5:53–59), instead working by favoured systhesis of $^{Ctm}PrP$, a transmembrane form of PrP (Hegde, et al. Science (1998) 279:827–834). Certain mutations in PrP (including the human prion disease-associated A117v mutation) alter its biogensis at the endoplasmic reticulum (ER), causing a higher percentage of PrP molecues to be synthesized in the transmembrane form $^{Ctm}PrP$. Expression of $^{Ctm}PrP$-favouring mutations in transgenic mice resulted in neurodegenerative changes similar to those observed in prion disease (Hegde, et al. Science (1998) 279:827–834) The detection of $^{Ctm}PrP$-favouring mutations suggested theat elevated $^{Ctm}Prp$ causes neurodegeneration (Hegde, et al. Science (1998) 279:827–834), but whether this mechanism of neurodegeneration is involved in the pathogenesis of transmissible prion disease has been unclear. To explore this question mice were generated with mutant PrP transgenes differing in their propensity to form $^{Ctm}PrP$, and subsequently their suceptibility to $PrP^{Sc}$ induced neurodegeneration was assessed.

Cell-free translation and translocation. Transcription of the relevant coding regions using SP6 polymerase, translation in rabbit reticulocyte lysate containing imcrosomal membranes from dog pancreas, and proteolysis were essentially as described previously (Hegde, et al. Science (1998) 279:827–834). Translation reactions were carried out at 32° C. for 40 minutes, and proteolysis reactions at 0° C. for 60 minutes using 0.5 mg/ml PK. Products were immunoprecipitated with the R073 antibody (Rogers, M. et al., J. Immun, 1991, 147:3568–3574), separated by SDS-PAGE on 15% acrylamide gels, and visualized by autoradiography.

TABLE 1

Transgenic mouse production and characterization.

| Transgenic Line Number | Transgenic Line Name | % Ctm in vitro | Level of PrP expr (rel to Sha) | Ctm-index | Age spont disease (days) | CtmPrP in vivo | Sc237 inc. time (days) |
|---|---|---|---|---|---|---|---|
| TgSHaPrp(STE)H | F1788 | 6 | 4 | 24 | – | – | 323 +/– 14(9/9) |
| TgSHaPrP(A117V)L | E15781 | 31 | 0.4 | 12 | – | – | 70 +/– 2 (6/6) |
| TgSHaPrP(A117V)H | E15727 | 31 | 4 | 124 | 572 +/– 35 (5/5) | + | 55 +/– (6/6) |
| TgSHaPrP(N1081)L | E15786 | 35 | 1 | 35 | – | – | 311 +/– (3-3) |
| TgShaPrp(N1081)H | E15790 | 35 | 5 | 175 | 312 +/– 24(7/7) | + | 233 +/– 2(9/9) |
| TgShaPrP(KH-II)L | E12485 | 48 | 0.4 | 19 | – | – | 257 +/– 2 (9/9) |
| TgSHaPrP(KH-II)M | F1220 | 48 | 1 | 48 | 472 +/– 13(6/6) | + | 181 +/– 5(10/10) |
| TgSHaPrP(KH-II) H | F1198 | 48 | 4 | 192 | 58 +/– 11 (24/24)[a] | ++ | ND[b] |

Table 1 Characteristics of transgenic mouse lines used in this study. The values for % Ctm in vitro were derived from quantitation of FIG. 8a. The levels of PrP expression were determined by quantitative western blotting with the 13A5 monoclonal antibody and re expressed relative to PrP expression in Syrian hamster *Sha; see FIG. 1B for a representative experiment). The Ctm-index for each transgenic line is derived by multiplying the values in the preceeding two columns. 'Age spont disease' indicates the age of onset of clinical symptons [average +/– SEM (n/n.)]. biochemical assay for determining the presence of $^{Ctm}$Prp in viro was as previously described[9,] and carried out on either clincially ill animals (in the case of transgenic lines developing illness) or mice over 600 days of age (in the case of transgenic lines that don't develop neurodegeneration). 'Sc237 inc. time' indicates the time from inoculation with Sc237 Sha prions to development of neurologic signs of dysfunction [average +/– SEM (n/n.)].
[a]Data from ref. 9.
[b]ND indicates not determined.

were generated as previously described (Manson, et al. Neurodegeneration (1994) 3:331–340 and references therein). PrP expression was assessed by immnunoblotting of brain tissue homogenate with 13A5 mAb (Kascsak, R. J. et al., J. Virology, 61:3688–3693), comparing to serial dilutions of normal Syrian hamster brain tissue (FIG. 8b and Table 1). Observation of these mice for development of spontaneous illness was as previously described (Prusiner Ann Neur (1982) 11:353–358). The double trangenic mice expressing both SHaPrP and MoPrP (see FIG. 11) were generated by crossing Tg[SHaPrP]/Prnp$^{0/0}$ (line A3922)[9] to Tg [MoPrP]/Prnp$^{0/0}$ (line B4053) (Telling Genes Dev (1996) 10:1736–1750). Transmissibility (see FIG. 10) was assessed by intracerebral inoculation of 1% brain homogenate (w/v) into mice (30 µl per animal) or hamsters (50 µl per animal) as previously described (Prusiner Ann Neur (1982) 11:353–358). the Sc237 strain of hamster prions (used in FIG. 9) and RML strain of mouse prions (used in FIG. 11) have been described previously (Marsh J Infect Dis (1975) 131:104–110; Chandler Lancet (1961) 1:1378–1379).

Assessment of brain for $^{Ctm}$Prp and PrP$^{Sc}$. Brain tissue (either freshly removed or stored frozen at –80° C. following flash-freezing in liquid nitrogen) was homogenized in PBS (at 5% w/v or 10% w/v) by successive passage through 16, 18 and 20 gauge needles. For $^{Ctm}$PrP detection ('mild' proteolysis conditions), 17 µl aliquots of the sample (at a concentration of 25 µg/µl) were adjusted (in a final volume of 20 µl) to 1% NP-40, 0.25 mg/mk PK and incubated for 60 min on ice. For PrP$^{Sc}$ detection ('harsh' proteolysis conditions), 17 µl samples (at a concentration of 25, µg/µl) were adjusted (in a final volume of 20 µl) to 0.5% NP-40, 0.5% deoxycholate, 0.1 mg/ml PK and incubated for 60 minutes at 37° C. It should be noted that the difference between mild versus harsh digestion conditions, while operational, is not subtle, as it involves a 37° change in temperature of incubation, and the presence of non-ionic detergent versus mixed micelles of non-ionic and ionic detergents. The proteolysis reactions were terminated by the addition of PMSF to 5 mM, incubating an additional 5 minutes, and transferring the sample to 5 volumes of boiling 1% SDS, 0.1M Tris, pH 8.9. Samples were then digested with PNGase as directed by the manufacturer, resolved by 10% tricine-SDS-PAGE, transferred to introcellulose, and probed with either the 3F4 or 13A5 monoclonal anitbody (Kascsak J Virol 61:3688–3693), or the RO73 polyclonal antibody (Rogers J Immunol (1991) 147:3568–3574).

Results

Shown in FIG. 8a are in vitro translocation products of four mutants of Syrian hamster (Sha) PrP that alter the amount of $^{Ctm}$PrP synthesized at the ER. Transgenic mice expressing each of these mutant PrPs in the FVB/Prnp$^{0/0}$ background were generated and characterized (see Table 1 and FIG. 8b). The Tg[SHaPrP(KH→II)$_H$], Tg[SHaPrP(KH→II$_m$], Tg[SHaPrP(A117V)$_H$] and Tg{SHaPrP(N108I)$_H$] mice were observed to develop signs and symptoms of neurodegenerative disease at approximately 60, 472, 572 and 312 days, respectively (FIG. 8c and Table 1). By contrast, neither the Tg[SHaPrP(ΔSTE)] mice nor mice expressing lower levels of the disease-associated transgenes {Tg[SHaPrP(KH→II)$_L$], Tg[SHaPrP(A117V)$_L$] and Tg[SHaPrP(N108I)$_L$]} developed spontaneous disease (Table 1 and data not shown). biochemical analyses of brain tissue from each of these lines of transgenic mice revealed elevated $^{Ctm}$PrP, but not PrP$^{Sc}$, in the lines which developed disease (FIG. 8d). Together, the data in FIG. 8 recapitulate the point that increased synthesis of the $^{Ctm}$PrP form of PrP is associated with the development of neurodegenerative disease.

More remarkable is the apparent dose response, seen in two ways, between $^{Ctm}$PrP and severity of disease. First, the more strongly that $^{Ctm}$PrP systhesis is favoured at the ER (KH→II>N108I>A117V), the earlier the onset of spontaneous disease (Table 1). Second, lowering the level of expression of each of these mutations below an apparent threshold abrogates both the generation of $^{Ctm}$PrP (FIG. 8d and ref. 9) and development of disease (Table 1). Furthermore, the three transgenic lines expressing the KH→II mutation develop disease at times inversely correlated with their respective levels of expression (Table 1). These observations demonstrate that bot the $^{Ctm}$PrP-favouring quality of a mutation and its level of expression contribute to the development of neuodegeneration.

This panel of transgenic mice with differing propensities to make $^{Ctm}$PrP was used to dissect the relationship between $^{Ctm}$PrP and PrP$^{Sc}$. We first examined the susceptibility to PrP$^{Sc}$ of transgenic mice with identical levels of transgene expression but differing propensities to make $^{Ctm}$PrP: Tg[SHaPrP(□STE)] and Tg[SHaPrP(A117V)$_H$]. Upon inoculation with Sc237 hamster prions, we found that the Tg[SHaPrP(□STE)] and Tg[SHaPrP(A117V)$_H$] mice developed illness at aproximately 323 and 54 days, respectively (FIG. 9a, Table 1). Biochemical analysis of representative mice at the time of disease onset revealed that the Tg[SHaPrP(□STE)] mice contained substantially more PrP$^{Sc}$ than the Tg[SHaPrP(A117V)$_H$] mice (FIG. 9b). Thus, the transgenic line that generates higher CtmPrP is more susceptible to PrP$^{Sc}$, developing disease at a lower level of overall PrP$^{Sc}$ accumulation.

We next compared the susceptibility to Sc237 of Tg[SHaPrP(KH→II)$_L$] versus Tg[SHaPrP(A117V)$_H$] (FIG. 9e). By keeping the mutation constant, issues regarding a potential barrier to propagation are avoided, while still changing the propensity to generate CtmPrP by modulating level of expression. As expected, lowering the level of expression increased the incubation time to disease following 5c237 inoculation. More remarkably however, we found that with both the KH→II and A117V mutants, the lower level expressor contained the higher level of PrPSC at the time of disease onset (FIG. 9*d,f*). A similar inverse relationship between level of expression and amount of PrPSC at disease has been observed with mice expressing different levels of wild type PrP (ref.10). Thus, as above, the mice with a diminished propensity to form OtmPrP had accumulated higher levels of PrPSC at onset of disease. To integrate the above inoculation data into a single plot, we ranked the different lines of transgenic mice by their relative propensities to generate CtmPrP using a measure we term the Ctm-index (see Table 1). This index is derived by multiplying the percent of chains synthesized in the CtmPrP topology by the level of transgene expression, thus incorporating the two parameters known to influence CtmPrP generation. FIG. 9*g* shows that a clear relationship exists between the Ctm-index and the amount of PrPSC that had accumulated at disease onset. This relationship suggests that the ability of PrPSC to cause disease is a function of the propensity of the host to generate CtmPrP.

The data in FIG. 9 demonstrate two important points. First, very different levels of PrP$^{SC}$ accumulation are observed at the time of onset of clinical disease upon inoculation of the various lines of transgenic mice. Given that the strain of mice is identical in each case, with the only differences being in the nature and level of expression of the PrP transgene, this observation underscores the conclusion that accumulation of protease-resistant PrP$^{Sc}$ is not likely to be the most proximate cause of disease; subsequent events (apparently involving $^{Ctm}$PrP) are likely to be involved. Second, there is a relationship between the amount of accumulated PrP$^{SC}$ and the factors that modulate $^{Ctm}$PrP generation. Such a relationship argues that $^{Ctm}$PrP and PrP$^{SC}$ are part of a pathway in which they potentially can influence, either directly or indirectly, each other's metabolism.

One way to reconcile the data in FIG. 9*g* is if accumulation of PrP$^{SC}$ caused increased generation of $^{Ctm}$PrP which then elicited neurodegeneration. Thus, transgenic mice that have an elevated propensity to generate $^{Ctm}$PrP (i.e., a high Ctm-index) would require less PrP$^{SC}$ accumulation before $^{Ctm}$PrP generation is increased beyond the threshold needed to cause disease. This model would explain the inverse relationship observed in FIG. 9*g*, and makes two additional predictions. First, since transgenic mice that substantially favour synthesis of PrP in the $^{Ctm}$PrP form can entirely circumvent the requirement for PrP$^{SC}$ in the developement of neurodegenerative disease, tissue from such mice should not be infectious. Second, $^{Ctm}$PrP levels should increase during the course of PrP$^{SC}$ accumulation in infectious prion disease. These predictions were tested.

To assess the transmissiblity of $^{Ctm}$PrP-associated disease, brain homogenate from clinically ill Tg[SHaPrP(KH→II)$_H$] mice were inoculated intracerebrally into four hosts: i) Tg[SHaPrP(KH→II)$_L$] mice expressing the KH→II mutation at low levels, ii) Tg[SHaPrP] mice overexpressing wild type SHaPrP, iii) FVB/Prnp$^{0/0}$ mice with a homozygous disruption of the PrP gene, and iv) Syrian hamsters. As shown in FIG. 10, homogenate from terminally sick Tg[SHaPrP(KH→II)$_H$] mice did not induce neurological illness at rates different than control Tg[SHaPrP] homogenate when directly compared in three independent hosts. Furthermore, biochemical and pathological examination of representative brain tissue from FIG. 10 at up to 625 days after inoculation did not show any evidence of PrP$^{Sc}$ or neurologic disease in either experimental or control animals (data not shown). Yet, inoculation of Tg[SHaPrP(KH→II)$_L$] mice with Sc237 prions readily generated PrP$_{SC}$ in brain (FIG. 2*d*), which re-transmitted disease to Tg[SHaPrP(KH→II)$_L$] and Tg[SHaPrP] mice (data not shown). Thus, although PrP(KH→II) is capable of being formed into PrP$^{SC}$, the $^{Ctm}$PrP. associated disease in Tg[SHaPrP(KH→II)$_H$] mice does not generate detectable PrP$^{SC}$ and therefore is not infectious. Lack of transmission provides further support for the hypothesis that neurodegeneration in these genetic prion diseases is caused by $^{Ctm}$PrP directly. The second prediction made on the basis of the data in FIG. 9*g* was that accumulation of PrP$^{SC}$ in infectious prion disease should induce the increased generation of $^{Ctm}$PrP, which would subsequently lead to neurodegeneration. Unfortunately, testing this prediction directly is hampered by the biochemical properties of the accumulating PrP$^{SC}$ (Meyer *PNAS* (1986) 83:2310–2314). Being highly protease-resistant and heterogeneous in its fractionation, it tends to contaminate substantially all subcellular fractions. Additionally, it interferes with the assays for $^{Ctm}$PrP. detection, which is also based on protection from proteases. Because PrP$^{SC}$ is not readily degraded by the cell and accumulates to very high levels[12], even very small amounts of contamination of suboellular fractions are sufficient to make detection of subtle increases in $^{Ctm}$PrP difficult. Thus, an alternate method is required to monitor the effect of accumulating PrP$^{SC}$ on the topology of newly synthesized PrP (see FIG. 11*a*).

In order to design such an experiment, we took advantage of three observations. First, a species barrier to PrP$^{SC}$ conversion exists between mouse and Syrian hamster (Prusiner *Cell* (1990) 63:673–686; Pattison *Res Vet Sci* (1968) 9:408–410). Second, in contrast to the species barrier for PrP$^{SC}$ formation, no species specific differences in the synthesis, translocation or topology are observed between mouse PrP (MoPrP) and SHaPrP (Hegde Science (1998) 279:827–834). And finally, monoclonal antibodies highly specific to SHaPrP (which do not cross react with MoPrP) are available to distinguish between expression of these two PrP transgenes[15]. Thus, in such double transgenic animals we can use hamster $^{Ctm}$PrP formation as a 'reporter' during the course of accumulation of mouse PrP$^{SC}$. For this experiment, the double transgenic mice which synthesize both MoPrP and SHaPrP are inoculated with mouse prions (of the RML strain). Then, at various intervals during the time course of accumulation of PrP$^{SC}$ and development of disease, individual mice are sacrificed and examined for total PrP$^{Sc}$ accumulation and for the presence of hamster $^{Ctm}$PrP$^{Sc}$ (see FIG. 4a). The principle is that following inoculation, only MoPrP will be a substrate for prion replication and PrP$^{SC}$ formation[13]. The effect of this PrP$^{Sc}$ accumulation on the ability of cells to generate (or not generate) $^{Ctm}$mPrP can be assessed by examining SHaPrP.

Clinical disease was noted to develop in these animals approximately 9 weeks after inoculation (data not shown). We found that PrP$^{SC}$ accumulated in these mice during this 9 week time course, with the earliest detectable times being approximately 5–6 weeks (FIG. 11b). As expected, the SHaPrP was not noted to have formed any PrP$^{SC}$ by both biochemical criteria in this study (FIG. 11b) and infectivity criteria in prior studies[13]. Remarkably however, a significant increase in the amount of $^{Ctm}$PrP was noted upon examination of the SHaPrP (FIG. 11c). Such an increase was not observed in a parallel set of mice that did not receive the inoculum (data not shown). These findings, coupled with the observation that $^{Ctm}$PrP is capable of causing neurodegeneration in the absence of an transmissible forms of PrP (ref. 9, FIGS. 8 and. 10), suggest that PrP$^{Sc}$ accumulation may cause disease by inducing the synthesis of $^{Ctm}$PrP de novo.

The findings described herein suggest causal relationships between PrP$^{SC}$ accumulation, the events of $^{Ctm}$PrP formation and metabolism, and the development of neurodegenerative disease. Three complementary and independent lines of evidence argue for this conclusion. First, increasing the generation of $^{Ctm}$PrP beyond a certain threshold (by modulating a combination of PrP mutation and level of expression) results in neurodegeneration in the absence of PrP$^{SC}$ formation (FIG. 8, FIG. 10 and ref. 9). Second, the amount of accumulated PrP$^{SC}$ needed to cause neurodegenerative disease is influenced by the propensity of the host to generate $^{Ctm}$PrP (FIG. 9). And third, the brain appears to contain increasing levels of $^{Ctm}$PrP during the course of accumulation of PrP$^{SC}$ (FIG. 11). Taken together, the data are suggestive of three successive stages in the pathogenesis of prion diseases (FIG. 12).

Infectious prion diseases are proposed to work by initiating the steps of Stage I, the accumulation of PrP$^{SC}$. Genetic prion diseases could in principle work at either Stage I or II. If the PrP mutation in question results in the spontaneous formation of PrP$^{SC}$, Stage I would be initiated, PrP$^{SC}$ would replicate and accumulate, and subsequently cause increased elevation of $^{Ctm}$PrP (stage II). Such a mechanism seems plausible for the E200K mutation thought to cause certain genetic variants of Creutzfeldt-Jakob disease[16]. Thus, PrP$^{Sc}$ is seen in these patients' 17, and the disease is readily transmissible to experimental animals[7]. Alternatively, certain other PrP mutations could bypass stage I altogether by directly causing an increase in $^{Ctm}$PrP generation. The A117V mutation resulting in human Gerstmann-Straussler-Scheinker[18] disease is likely to work by such a mechanism. This would explain why this disease has not been transmissible[6-8], and why PrP$^{SC}$ has not been detected in these patients' brain tissue[6,9].

The final stage in prion disease pathogenesis includes the mechanisms by which $^{Ctm}$PrP, once generated, leads to neurodegenerative disease. The mechanism by which this occurs and the intracellular pathways that are involved remain entirely unclear. However, it does not appear to be the case that $^{Ctm}$PrP is simply misfolded, retained or accumulated in the ER, or eliciting an unfolded protein response. This is suggested by the observation that essentially all of the $^{Ctm}$PrP has been trafficked beyond the ER[9], the site of the presently known quality control machinery for protein folding in the secretory pathway[19,20]. Additionally, disease can be elicited by transgenes expressed at close to physiologic levels, as is the case with Tg[SHaPrP(KH→II)$_M$] animals or human cases of GSS containing the A117V mutation. Thus, a more selective means by which $^{Ctm}$PrP induces neurodegeneration is suggested by the available data.

The framework described in FIG. 12 suggests several new avenues for future studies. First, the regulated events in $^{Ct}$$_m$PrP biogenesis and trafficking remain to be elucidated. The reconstitution of the early events of PrP translocation and topology determination in a cell-free system amenable to fractionation appears to be a promising avenue for the identification of trans-acting factors regulating $^{Ctm}$PrP synthesis[21,22]. Additionally, the availability of several mutants influencing topology should facilitate studies aimed at defining later events in the trafficking of $^{Ctm}$PrP. Second, insights gained from studying the metabolism of $^{Ctm}$PrP will undoubtedly allow for a better understanding of how these events are modulated in trans by PrP$^{SC}$ accumulation. Such studies are likely to better delineate the relationship between the events of PrP$^{SC}$ accumulation and $^{Ctm}$PrP mediated neurodegeneration. Given that PrP$^{SC}$ accumulation may impact upon several metabolic functions of the cell[23,24,25], it is plausible that one or more of these influence $^{Ctm}$PrP generation to elicit disease. The availability of PrP mutants that act at a step beyond PrP$^{SC}$ accumulation to directly cause $^{Ctm}$PrP mediated neurodegeneration (ref. 9 and FIG. 8) should facilitate the dissection of the downstream events in prion disease pathogenesis.

EXAMPLE 3

Effect of Prolactin, Beta Lactamase, and Immunoglobulin G Heavy Chain Signal Sequences on Protein Conformation In general, a dichotomy has been accepted between a protein being properly folded versus misfolded (Ellgaard et al. (1999) Science 286; 1882–1888). In other words, the possibility that proteins might have more than one properly folded state and might even be able to select one versus another folded state at different times or circumstances has not been considered. Because a linear polypeptide sequence folding in different ways could have substantially different shapes, physical properties and biological activities, this new level of regulation greatly increases the information content of the genome and the potential for regulation of gene expression available to the cell. To test this hypothesis we first selected three unrelated, simple secretory proteins, namely, prolactin (prl), beta lactamase (βlac), and Immunoglobulin G heavy chain (IgG), to determine whether the individual signal sequences would be equally efficient at translocation of their own passenger sequences across the ER membrane (see FIG. 13) as those of different nascent chains.

We truncated aliquots of these cDNAs at each of three unique restriction endonuclease recognition sites, so that when transcribed the truncated cDNAs generated RNA transcripts encoding longer and longer C-terminally-extended lengths of these secretory proteins, and finally expressed these transcripts in cell-free translation systems supplemented with microsomal membranes. As can be seen in FIG. 14, despite the fact that these three signal sequences are equally highly efficient at translocating their own nascent chains, radically different ribosome-membrane junctions are established for translocation of different nascent chains, as determined by accessibility of the nascent truncated chain to digestion with proteinase K (see cartoon to right of each panel of FIG. 14).

Initially upon targeting to the ER membrane, all three chains remain accessible to protease (left hand panels of FIG. 14A–C). Shortly thereafter, in the case of prolactin, a tight seal is established as the nascent chains is translocated directly to the ER lumen (see middle panel of FIG. 14A). However, in the case of both beta lactamase and IgG heavy chain, the ribosome-membrane junction remains open at a substantially later point (see middle panel of FIGS. 14B and C), and only much later does it efficiently close (right hand panel of FIGS. 14B and C). This suggests that different proteins translocate to the ER lumen via strikingly different ribosome-membrane junctions. If, as suggested by the studies on prion protein (PrP) biogenesis, signal sequences are involved in regulation of protein folding, this could occur in part through establishing different environments in which the nascent chain starts to fold. When the ribosome-membrane junction remains open, as in the middle panel of FIGS. 14B and 14C, the chain starts to fold in the reducing environment of the cytosol; when the ribosome-membrane junction is closed, as in the middle pane of FIG. 14A and the right hand panels of FIGS. 14B and 14C, the unfolded or partly folded chain proceeds to the oxidizing environment of the ER lumen to initiate or continue the process of folding funnel selection.

As shown above (Example 1) in the case of the biogenesis of prion protein (PrP), the open and closed states of the ribosome membrane junction correlate to the synthesis of secretory versus Ctm forms of PrP, identical polypeptide sequences that are folded differently and in different transmembrane topological forms. The data in FIG. 14 extends this correlation of the state of the ribosome-membrane junction with the folding of the protein, to simple secretory proteins such as prolactin and immunoglobulin heavy chain.

If signal sequences play the hypothesized regulatory role in protein folding, in part through the nature of the ribosome-membrane junction they establish, then swapping the signal sequence of two different secretory proteins should have a dramatic consequence, in the form of three predictions:

First, swapping of the signal sequence should change the environment in which the nascent chain resides (e.g.as assessed either by a change in the ribosome-membrane junction as probed with proteinase K, or by a change in the proteins with which the nascent chain is associated as determined by chemical crosslinking). An example of a chemical crosslink difference between nascent chains of prolactin behind the prolactin signal sequence and prolactin behind the IgG signal sequence is shown in FIG. 15. Substantailly the same conclusion was reached for PrP.

Second, the folding of the two proteins, directed down two different folding funnels by virtue of interaction with different accessory proteins in different environments, is likely to be different. One way to score this would be by engineering in glycosylation sites as reporters of protein conformation and demonstrating that the same chain is glycosylated when it is behind one signal sequence but not another, even though both signal sequences are ultimately cleaved from the protein. This is demonstrated in FIG. 16 for prolactin with an engineered glycosylation reporter, behind either its own signal sequence (Prl) or the signal sequence of immunoglobulin heavy chain (IgG/Prl), growth hormone (GH/Prl). As can be seen from the $5^{th}$ lane of each panel in FIG. 16A, the resulting mature prolactin chain made behind different signal sequences is conformationally different as assessed by the ability of oligosaccharyl transferase to add core N-linked sugars to the nascent chains. FIG. 16B quantitates this difference. Expression of truncations of these constructs reveal that the difference in glycosylation of one prolactin compared to another, is not a kinetic phenomenon because prolonged incubation of the truncated and therefore non-growing but nascent chains, did not result in any further degree of glycosylation. FIG. 16C shows that this difference in conformation, as scored by glycosylation, is readily apparent from material secreted into the medium of cos cells transfected with the corresponding constructs encoding prolactin behind the various signal sequences. Thus the conformation of prolactin is changed simply by virtue of its synthesis behind a different signal sequence. That difference cannot be accounted for by the known roles of the signal sequence, because all signal sequences utilized are equally competent for targeting and translocation of both their native substates (see FIG. 13) and that encoded by the modified prolactin coding region. Furthermore, all conformations of prolactin synthesized in FIG. 16 are judged as properly folded by the quality control machinery, as assessed by their secretion into the medium.

A third prediction is that, in some cases of swapped signal sequences, the "mis-match" between the signal and the subsequent passenger may be sufficiently severe that even fully targeted chains are incapable of finding a folding funnel compatible with translocation into the ER lumen and may instead "fall back" into the cytosol, unable to be translocated. Precisely this form of defect was observed for a PrP mutant that could only be expressed in the secretory form with intact ER membranes, and whose expression in glycoprotein-depleted reconstituted microsomal membranes resulted in an inability of the chain to be translocated (Hegde et al, (1998) Mol Cel 2:85–91).

In FIG. 13 we demonstrate that behind the βlac and IgG signal sequences, prolactin displays a substantial translocation defect (FIG. 13A), which which can be remedied by introduction of sequences from the region of IgG subsequent to the signal sequence (FIGS. 13B and 13C). Furthermore the defect in mutant PrP translocation across glycoprotein-depleted reconstituted membranes can be corrected by swapping the PrP signal sequence for that of prolactin (data not shown), suggesting that the defect was neither intrinsic to the membranes nor the chain, but rather, reflected an incompatibility of a particular signal sequence-chain combination, consistent with the hypothesized role of the signal sequence in folding funnel selection.

EXAMPLE 4

From the above, it can be seen that, the signal sequence can determine the final folded state of the protein, as demonstrated by accessibility of a glycosylation site engineered into the protein behind some signal sequences but not others. As the growing chain proceeds down different folding funnels, depending on the nature of the ribosome-membrane junction and protein-protein interactions between the nascent chain and the translocation machinery, different conformations are achieved. As a result of those differences in conformation, even while the chain is growing, the differently folded forms of a protein are differentially accessible to modification enzymes. Hence, an engineered glycosylation site serving as a reporter of protein conformation is glycosylated when engineered behind one signal sequence but not another. Furthermore, in the extreme case where the nature of the ribosome-membrane junction is such as to allow substantial chain folding to be initiated prior to translocation, additional information in the authentic chain must emerge to close the ribosome-membrane junction. Without such additional information, the chain may fail to translocate, as demonstrated for prolactin behind the IgG signal sequence.

Thus, a model secretory protein recapitulates the observations made previously for the prion protein (Example 1), indicating that those results were not a special case. Indeed, what appears to be special about the prion protein is not the pathway of its biogenesis and folding, but that the alternative folding pathways manifest as topological differences, making them far more easy to detect.

EXAMPLE 5

Modulation of Protein Folding by Trans Acting Factors

As shown in Example 1, above, the time course of $PrP^{Sc}$ accrual in transmissible prion disease is followed closely by increased generation of $^{Ctm}PrP$. Thus, the accumulation of $PrP^{Sc}$ appears to modulate in Trans the events involved in generating or metabolising $^{Ctm}PrP$. $^{Ctm}PrP$, which has its C terminal domain translocated to the ER lumen, triggers spontaneous neurodegeneration when overexpressed (Hegde, *Science* (1998) 279:827–834). As shown in Example 2, $^{Ctm}$PrP appears to be induced just prior to onset of clinical signs, suggesting that it initiates a final common pathway to neurodegeneration. An as yet unknown glycoportein of the ER membrane is implicated as a translocation accessory factor (TrAF) that “protects” the normal brain from expression of $^{Ctm}$PrP by directing nascent PrP chains to the pathway leading to $^{sec}$PrP (Hegde *Mol Cell* (1998) 2:85–89).

The mechanism by which nascent PrP chains are allocated among the topological forms is complex (Rutkowski, submitted). The PrP signal sequence itself may play a role by establishing at least two populations of nascent chains: some with an open ribosome-membrane junction; others with a closed ribosome-membrane junction. Thus, the signal sequence can determine the environment faced by the emerging N-terminal domain of PrP. Only the chains exposed to the cytosolic environment have the potential to become $^{Ctm}$PrP. While necessary, an open ribosome-membrane junction is not sufficient to make $^{Ctm}$PrP, as additional protein-protein interactions determine the final outcome. Mutations that prevent the transmembrane domain from directing. $^{Ctm}$PrP formation result in these chains being redirected to the cytosol, where they most likely are degraded.

The distinction between $^{sec}$PrP and $^{Ctm}$PrP usually are made on topological grounds. However, these two polypeptides of identical sequence also differ in their conformation, as determined by their differential sensitivity to limited protease digestion in non-denaturing detergent solutions. Thus, translocational regulation appears to be a means of generating multiple forms of PrP that differ in both confomation and function. The machinery (i.e. a TrAF) that directs nascent PrP chains to make $^{sec}$PrP rather than $^{Ctm}$PrP, may itself be regulated, based on the ability of scrapie infection to increase the amount of $^{Ctm}$PrP detectable in brain. Together, these observations lead to a new principle: a protein’s conformation is determined not just by its primary amino acid sequence, but also by proteins such as TrAF, that influence which of two or more different functional conformational outcomes actually occur or predominate.

Complex secretory or integral membrane proteins therefore can have many potential functional folded states. The different folded states become manifest by a combinatorial series of interactions between ligands within the nascent chain and receptors at the translocon, in an array of possible environments (e.g. cytosol, membrane, lumen). The rates of generation versus degradation of the various conformations determine which, and how many, of the possible final outcomes for a particular substrate are expressed at any given time. These processes are integrated by signaling pathways from the cell surface and elsewhere, which coordinate protein biogenesis with both the specific immediate needs (Chapman *Annu Rev Cell and Dev Biol* (1998) 14:459–485) and the global program of the cell (Bonafacino *Nature* (1990) 334:247–251)

This view necessitates that secretory and integral membrane nascent chains proceed down more than one folding funnel (or take different paths to different ends within a single, complex folding funnel). This is accomplished through the interaction of discrete sequences in the nascent chain with TrAFs or the environments that TrAFs make accessible. Different TrAFs, localized to different compartments (cytosol, membrane, ER lumen), that can act on different chains or different subsets of folding states of a given chain also contributes to the selection of one functional folded form versus another. This can be thought of as “third-order” complexity in protein folding. It differs from the concept of molecular chaperones in that each of the possible structural outcomes are functional—just different in some aspect of function or regulation. Thus secretory and integral membrane proteins could exist in multiple confomations, each with a distinctive functional signature.

Finally, the translocon and its components including TrAFs, that dictate the choice among possible alternative folding funnels could themselves be subject to regulation by intracellular signaling, providing a “fourth order” of complexity to protein folding. FIG. 18 summarizes a working model of translocational regulation and relates it to the four orders of protein folding.

In order to explore translocational regulation in trans we have developed fractionated and reconstituted systems in which, as a result of manipulation of either the cytosol or the membranes, the conformational mix of PrP can be altered. Since the findings with PrP have been shown (Rutkowski and Lingappa) to be reproduced by studies in other unrelated proteins (Rutkowski and Lingappa; Lingappa, Buhman, and Farese) it is clear that these systems will be amenable to manipulation in order to achieve the goals of detecting and studying the conformers of any signal sequence containing gene product of interest.

Results

Previously, the evidence for trans-acting influences affecting translocation and conformation have been relatively indirect (Hegde et al. (1998) Mol Cell 2:85–91; Hegde et al. (1999) Nat. 402:822–826). We have now found two new lines of evidence that support this notion more directly. First we have observed that cytosolic extracts prepared from mouse erythroleukemia (MEL) cells before and after differenciation are able to affect translocation of PrP, shifting the distribution of forms in favor of Sec-PrP (see FIG. 19). Second, when microsomal membranes were prepared from hamster brain at various times in early post-natal development, TrAF activity was found to vary, going from high in day 13 embryonic brain, to a nadir at post-natal day 14, in a manner consistent with the hypothesis that TrAF activity, which suppresses Ctm-PrP, is decreased in selected brain regions to promote Ctm-PrP and trigger neuronal apoptosis as part of the program of early rodent brain development (see FIG. 20).

In view of the results described above, we set about to fractionate the rabbit reticulocyte lysate in a manner that would be amenable to complementation with trans-acting factors from other sources. We found that a combination of ribosome pellet and DEAE eluate fraction were sufficient to restore full translational activity (see FIGS. 21–23). The fractionation methodology is described above.

Similarly, we modified previously published protocols (Gorlich and Rapoport (1994) Cell 75:615–630; Hegde et al. (1998) Mol Cell 2:85–91) to generate fractionated and reconstituted proteoliposomes that were functionally equivalent to previous preparations, but which had advantages in terms of cost, speed, and amenability to further fractionation. This protocol is described above.

It is evident from the above results that the subject invention provides a new platform and paradigm for detecting, magnifying, understanding and manipulating the participation of the translocation system in physiological processes and the effect of different conformers of any secretory or integral membrane protein, or other protein with a signal sequence for translocation across the ER membrane, on the physiology of a host. By virtue of being able to control the folding of a protein, where different conformers may lead to different physiological outcomes, the opportunity to investigate the effect of the conformers on cellular pathways, the identification of agents involved with the formation of the different conformers, treatment for adverse results from a particular conformation and understanding of the cellular processes resulting from the formation of the different conformers, can be achieved. New drugs can be developed and diseases can be considered from different viewpoints than have been heretofore employed.

The above results also demonstrate that microsomal membranes prepared from different species with different genetic composition provide a powerful tool for the expressing normally minor conformers. In this case, sea urchin microsomal membranes were found to be highly translocation competent, but to generate only one conformer of PrP, Ctm-PrP, a form that is normally a minor species in the presence of mammalian microsomal membranes. The potential advantage of this approach over the biochemical approach is that labile components are less likely to have been inactivated by the procedure, and multiple components can be distinguished by the presence of distinctive partial activities in different membranes. Also the preparation of membranes from tissues of primitive organisms may be more cost-effective, at least for an initial screen, with positive results confirmed with the more expensive, biochemically pure reagents.

The novel protocol provided for the preparation of fractionated and reconstituted proteoliposomes makes use of relatively inexpensive detergents compatible with ion exchange chromatograpy, allowing for further fractionation of activities initially identified in the con A-depleted reconstitution, as well as activities whose initial identification requires further fractionation of Con A flow-through. A further novel advantage of the procedure provided here is that it makes the initial screen for novel TrAFs prior to commitment of a major effort, quite non-labor intensive. This is especially important given the possibility that some TrAF activities may involve more than one component and that, in some cases, one component in excess may be able to partially compensate for lack of another component.

Although the foregoing invention has been described in some detail by way of illustration and example for purposes of clarity of understanding, it will be obvious that certain changes and modifications may be practiced within the scope of the appended claims. All references cited herein are incorporated herein by reference, as if set forth in their entirety.

What is claimed is:

1. A method for detecting a conformational difference between proteins, said method comprising:

analyzing a non-denatured protein by high pressure liquid chromatography, wherein said protein is obtained by expression of a chimeric gene having a DNA sequence encoding at least substantially the same amino acid sequence as an open reading frame encoding a native protein, wherein said native protein is encoded by a gene having a native signal sequence and said chimeric gene has a signal sequence other than said native signal sequence so that a chimeric gene product is produced, wherein an alteration in the chromatographic profile of said chimeric gene product as compared to a native protein is indicative of a conformational difference between said chimeric gene product and said native protein.

2. The method according to claim 1, wherein said high pressure liquid chromatography is performed using hydrophobic adsorption columns.

* * * * *

SEQUENCE LISTING

<160> NUMBER OF SEQ ID NOS: 5

<210> SEQ ID NO 1
<211> LENGTH: 27
<212> TYPE: PRT
<213> ORGANISM: prion

<400> SEQUENCE: 1

Met Ala Asn Leu Ser Tyr Trp Leu Leu Ala Leu Pro Val Ala Met Trp
1               5                   10                  15

Thr Asp Val Gly Leu Cys Lys Lys Arg Pro Lys
            20                  25

<210> SEQ ID NO 2
<211> LENGTH: 27
<212> TYPE: PRT
<213> ORGANISM: prion

<400> SEQUENCE: 2

Met Arg Arg Leu Ser Tyr Trp Leu Leu Ala Leu Pro Val Ala Met Trp
1               5                   10                  15

```
Thr Asp Val Gly Leu Cys Lys Lys Arg Pro Lys
            20                  25

<210> SEQ ID NO 3
<211> LENGTH: 27
<212> TYPE: PRT
<213> ORGANISM: prion

<400> SEQUENCE: 3

Met Asp Asp Leu Ser Tyr Trp Leu Leu Ala Leu Pro Val Ala Met Trp
1               5                   10                  15

Thr Asp Val Gly Leu Cys Lys Lys Arg Pro Lys
            20                  25

<210> SEQ ID NO 4
<211> LENGTH: 27
<212> TYPE: PRT
<213> ORGANISM: prion

<400> SEQUENCE: 4

Met Ala Asn Arg Arg Tyr Trp Leu Leu Ala Leu Pro Val Ala Met Trp
1               5                   10                  15

Thr Asp Val Gly Leu Cys Lys Lys Arg Pro Lys
            20                  25

<210> SEQ ID NO 5
<211> LENGTH: 27
<212> TYPE: PRT
<213> ORGANISM: prion

<400> SEQUENCE: 5

Met Ala Asn Asp Asp Tyr Trp Leu Leu Ala Leu Pro Val Ala Met Trp
1               5                   10                  15

Thr Asp Val Gly Leu Cys Lys Lys Arg Pro Lys
            20                  25
```